(12) United States Patent
Ryan et al.

(10) Patent No.: US 9,616,139 B2
(45) Date of Patent: Apr. 11, 2017

(54) CONJUGATING AMINES

(75) Inventors: Edward T. Ryan, Wellesley, MA (US);
Pavol Kovac, Silver Spring, MD (US);
Firdausi Qadri, Dhaka (BD); Peng Xu,
Rockville Pike, MD (US); Stephen B. Calderwood, Wellesley, MA (US);
Willie Frank Vann, Gaithersburg, MD (US); Dwight Christopher Peterson,
Chevy Chase, MD (US)

(73) Assignees: The General Hospital Corporation,
Boston, MA (US); The United States, as represented by the secretary, Department of Health and Human Services, Washington, DC (US);
International Centre for Diarrhoeal Disease Research, Bangladesh, Dhaka (BD)

( * ) Notice: Subject to any disclaimer, the term of this patent is extended or adjusted under 35 U.S.C. 154(b) by 0 days.

(21) Appl. No.: 14/128,958

(22) PCT Filed: Jul. 11, 2012

(86) PCT No.: PCT/US2012/046196
§ 371 (c)(1),
(2), (4) Date: Sep. 8, 2014

(87) PCT Pub. No.: WO2013/009826
PCT Pub. Date: Jan. 17, 2013

(65) Prior Publication Data
US 2015/0031863 A1 Jan. 29, 2015

Related U.S. Application Data

(60) Provisional application No. 61/507,054, filed on Jul. 12, 2011, provisional application No. 61/569,632, filed on Dec. 12, 2011.

(51) Int. Cl.
| | | |
|---|---|---|
| *A61K 38/02* | (2006.01) | |
| *A61K 47/48* | (2006.01) | |
| *A61K 39/02* | (2006.01) | |
| *C08B 37/00* | (2006.01) | |
| *C08H 1/00* | (2006.01) | |
| *C08L 89/00* | (2006.01) | |
| *A61K 9/00* | (2006.01) | |
| *A61K 39/08* | (2006.01) | |
| *A61K 39/00* | (2006.01) | |

(52) U.S. Cl.
CPC ........ *A61K 47/4833* (2013.01); *A61K 9/0019* (2013.01); *A61K 39/08* (2013.01); *A61K 39/107* (2013.01); *C08B 37/00* (2013.01); *C08H 1/00* (2013.01); *C08L 89/00* (2013.01); *A61K 2039/55544* (2013.01); *A61K 2039/6037* (2013.01); *A61K 2039/6081* (2013.01); *A61K 2039/627* (2013.01)

(58) Field of Classification Search
None
See application file for complete search history.

(56) References Cited

U.S. PATENT DOCUMENTS

2003/0068324 A1 4/2003 Fournier et al.

FOREIGN PATENT DOCUMENTS

RU 2412944 2/2011

OTHER PUBLICATIONS

Oberli et al ('A possible oligosaccharide-conjugate vaccine candidate for Clostridium difficile is antigenic and immunogenic' Chemistry and Biology v18 May 27, 2011 pp. 580-588).*
Grandjean et al ('Investigation towards bivalent chemically defined glycoconjugate immunogens prepared from acid-detoxified lipopolysaccharide of Vibrio cholera O1, serotype Inaba' Glycoconj J v26 2009 pp. 41-55).*
Bongat A.F. et al. "Multimeric bivalent immunogens from recombinant tetanus toxin HC fragment, synthetic hexasaccharides, and a glycopeptide adjuvant". Glycoconj. J., Jan. 2010; 27(1):69-77, (abstract).
Xu P. et al. Simple, direct conjugation of bacterial 0-SP-core antigens to proteins: development of cholera conjugate vaccines. Bioconjug Chem., Oct. 19, 2011, 22(10):2179-85.
International Search Report and Written Opinion mailed Nov. 9, 2012 in international application No. PCT/US2012/046196, 7 pgs.
Fairweather et al., "Cloning, Nucleotide Sequencing, and Expression of Tetanus Toxin Fragment C in *Escherichia coli*," Journal of Bacteriology 165(1):21-27 (1986).
Figueiredo et al., "Characterization of Recombinant Tetanus Toxin Derivatives Suitable for Vaccine Development," Infection and Immunity 63(8):3218-3221 (1995).
Louch et al., "Identification of a binding site for ganglioside on the receptor binding domain of tetanus toxin," Biochemistry 41:13644-13652 (2002).

* cited by examiner

*Primary Examiner* — Karlheinz R Skowronek
*Assistant Examiner* — Ronald Niebauer
(74) *Attorney, Agent, or Firm* — Fish & Richardson P.C.

(57) ABSTRACT

The disclosure provides directly conjugated polysaccharide vaccine molecules and methods related thereto.

18 Claims, 35 Drawing Sheets

Repeating Unit

→ 3)-α-D-Galp (1→

→ 2)-α-D-Manp (1→3)-α-D-Manp (1→3)-α-D-Manp (1→2)-α-D-Manp (1→2)-α-D
-Manp (1→

→ 4)-α-D-Galp (1→2)-β-D-Rlbf (1→

→ 3)-α-D-Manp (1→2)-α-D-Manp (1→3)-α-D-Manp (1→2)-α-D-Manp (1→2)-α-D
-Manp (1→

→ 2)-α-L-Rhap (1→2)-β-D-Ribf (1→3)-α-L-Rhap (1→3)-α-L-Rhap (1→
       OAc        OAc       OAc
       ⋮2/4      ⋮2       ⋮2/6

→ 3)-α-D-Galp (1→3)-α-D-Galf (1→3)-α-D-Galp (1→
                                       OAc
                                       ⋮6
                                   α-D-Galp
                                       |
                                       ↓
                                       3

→ 3)-α-D-Galf (1→3)-α-D-Galp (1→3)-α-D-Galf (1→2)-α-D-Galp (1→
                                       ⋮6
                                     OAc → 3)-α-L-Rhap (1→3)-β-D-Ribf (1→3)-α-L-Rhap (1→3)-β-D-Ribf (1→4)-α-L-
Rhap (1→

FIG. 12

Repeating Unit

→4)-α-D-GalNAcp-(1→4)-α-D-QuiNAcp-(1→3)-α-L-Rhap-(1→

→4)-β-D-ManImUp-(1→4)-β-D-Man(NAc)₃U-(1→3)-β-D-FucNAcp-(1→

→4)-β-D-ManImUp-(1→4)-β-D-Man(NAc)₃Up-(1→3)-α-D-FucNAcp-(1→

→4)-α-D-GalNAcp-(1→4)-β-D-Glc(NAc)₃Ap-(1→3)-α-D-FucNAcp-(1→
→3)-α-D-QuiNAcp-(1→

→3)-α-L-FucNAcp-(1→3)-β-D-FucNAcp-(1→2)-β-D-Glcp-(1→

ATGGGATCCTCAAAAATCTGGATTGTTGGGTTGATAATGAAGAAGATATAGATGTTATATTAAA
AAAGAGTACAATTTTAAATTTAGATATTAATAATGATATTATCAGATATATCTGGGTTTAATT
CATCTGTAATAACATATCCAGAGATGCTCAATTGGTGCCCGGAATAAATGGCAAAGCAATACATTTA
GTAAACAATGAATCTTCTGAAGTTATAGTGCATAAAGCTATGGATATTGAATATAATGATATGTT
TAATAATTTTACCGTTAGCTTTTTGGTTGAGGGTTCCTAAAGTATCCTGCTAGTCATTTAGAACAAT
ATGGCACACAAATGAGTATTCAATAATTAGCTCTATGAAAAAAACATAGTCTATCAATAGGATCTGGT
TGGAGTGTATCACTTAAAGGTATTTACCTGATAATAAATTTAAATGCTTATTTAGCAAATAAATGGGTTTTA
ACAAATAACTTTTAGGGATTTACCTGATAATAAATTTAAATGCTTATTTAGCAAATAAATGGGTTTTA
TAACTATTACTAATGATAGATTATCTTCTGCTAATTTGTATATATAAATGGAGTACTTATGGAAGT
GCAGAAATTACTGGTTTAGGAGCTATTAGAGAGGATAATAATAACATTAAAACTAGATAGATG
TAATAATAATAATCAATACGTTTCTATTGATAAATTTAGGATATATTTGCAAAGCATTAAATCCAA
AAGAGATTGAAAAATTATACACAAGTTATTTATCTATAACCTTTTTAAGAGACTTCTGGGAAAC
CCTTTACGATATGATACAGATTATATGTATTTGACAAATGCGCCATCGTATACTAACGGAAAATTGAATA
GAAAAATATAACAGATTATATGTATTTGACAAATGCGCCATCGTATACTAACGGAAAATTGAATA
TATATTATAGAAGGTTATATATAATGGACTAAAATTTATTATAAAAGATATACACCTAATAATGAA
ATAGATTCTTTGTTAAATCAGGTGATTTTAAAATATGTATCATATAACAATAATGAGCA
CATTGTAGGTTATCCGAAAGATGGAAAATGCCTTTAATAAAAATGGAAGCAGTAGAATTCTAAGAGTAGGTT
ATAATGCCCCAGGTATCCCCTCTTTATAAAAATGATGATAAAAATGCATCTTTAGGACTAGTAGGTACCCATAA
TATTCTAGTCAACTTAAATTATATGATGATAAAAATGCATCTTTAGGACTAGTAGGTACCCATAA
TGGTCAAATAGGCAACGATCCAAATATTAATTGCAAGCAACTGGTACTTTAATCATT
TAAAAGATAAAATTTTAGGATGTGATTGGTACTTTGTACCTACAGAGATGAAGGATGGACAAATGAT
TAA

FIG. 22

MGSSKNLDCWVDNEEDIDVILKKSTILNLDINNDIISDISGFNSSVITYPDAQLVPGING
KAIHLVNNESSEVIVHKAMDIEYNDMFNNFTVSFWLRVPKVSASHLEQYGTNEYSISSM
KKHSLSIGSGWSVSLKGNNLIWTLKDSAGEVRQITFRDLPDKFNAYLANKWVFITTNDR
LSSANLYINGVLMGSAEITGLGAIREDNNITLKLDRCNNNNQYVSIDKFRIFCKALNPKE
IEKLYTSYLSITFLRDFWGNPLRYDTEYYLIPVASSKDVQLKNITDYMYLTNAPSYTNG
KLNIYYRRLYNGLKFIIKRYTPNNEIDSFVKSGDFIKLYVSYNNNEHIVGYPKDGNAFNN
LDRILRVGYNAPGIPLYKKMEAVKLRDLKTYSVQLKLYDDKNASLGLVGTHNGQIGNDPN
RDILIASNWYFNHLKDKILGCDWYFVPTDEGWTND*

FIG. 23

CONJUGATING AMINES

CROSS-REFERENCE TO RELATED APPLICATIONS

This application is a U.S. National Phase Application under 35 U.S.C. §371 of International Patent Application No. PCT/US2012/046196, filed on Jul. 11, 2012, which claims the benefit of U.S. Ser. No. 61/507,054, filed Jul. 12, 2011, and 61/569,632, filed Dec. 12, 2011, which are incorporated by reference herein in their entirety.

FEDERALLY SPONSORED RESEARCH OR DEVELOPMENT

The inventions disclosed herein were made with Government support under Grant Nos. U01 A1077883, U01 A1058935, U01 A1089721, and TW05572. awarded by the National Institutes of Health. The Government has certain rights in the invention.

TECHNICAL FIELD

This disclosure relates to novel chemical processes for directly conjugating amine-containing species and compositions related thereto.

BACKGROUND

Infection with *Vibrio cholerae* elicits protection against subsequent disease for three to ten years. Immunity against *V. cholerae* is serogroup specific. A major protective antigen of this organism and many other bacterial pathogens is the 0-specific polysaccharide (OSP) of lipopolysaccharide (LPS) (Passwell et al., Infection Immunity 2001; 69(3): 1351-7; Robbins et al., Pure Appl Chem. 1999; 71:745-54). Unfortunately, polysaccharides are poor immunogens, likely due to the lack of T cell help, especially in young children. Conjugation of polysaccharides to proteins can markedly improve their immunogenicity, including magnitude, type, and duration (Goldblatt, Clinical and Experimental Immunology 2000; 119(1):1-3); examples include pneumococcal, meningococcal, and *Haemophilus influenzae* b conjugate vaccines (Claesson et al., Ped Inf Dis J 1991; 10(8):560-4). Current oral cholera vaccines provide lower level and shorter term protection than that afforded by wild type infection. The oral killed-cholera vaccine, WC-rBS (Dukoral), does not elicit memory B-cell responses to LPS (Alam et al., Clin Vaccine Immunol; 18(5):844-50). In addition, children had a lessened response to LPS after wild type disease and vaccination (Chowdhury et al., Pediatric Infectious Disease Journal 2008; 27(11):986-92).

Conventional conjugation techniques, such as conjugate vaccine production techniques, are limited in that they can be slow, costly, inefficient, require use of exogenous or added chemical linkers, and/or can lack reproducibility. Improved techniques are required.

SUMMARY

The present disclosure provides chemical methods for conjugating amine-containing species (e.g., polysaccharides) directly to amine-containing carriers (e.g., proteins). More specifically, the disclosure provides chemical methods using squaric acid chemistry for conjugating free amine-containing species (e.g., polysaccharides) directly to amine-containing carriers (e.g., proteins), for example, without prior modification of the amine containing species or the carrier.

In some embodiments, the disclosure provides conjugate molecules that include:

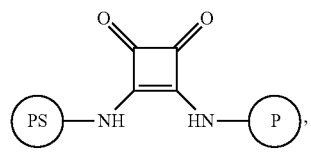

in which 'PS' is one or at least one polysaccharide (e.g., 1, 2, 3, 4, 5, 6, 7, 8, 9, 10, 10-20, 20-30, or more polysaccharides) with one or at least one accessible amine group and in which P is an amine group containing protein. In some aspects, the one or at least one polysaccharide can be or can include bacterial polysaccharides, or antigenic fragments of bacterial polysaccharides, including, for example, detoxified bacterial polysaccharides, or fragments of detoxified bacterial polysaccharides. In some aspects, the one or at least one polysaccharide can be or can include O-PS-core polysaccharides (e.g., the polysaccharide component of lipopolysaccharide (LPS) that includes an O-polysaccharide (O-PS) and a core or core-like polysaccharide (core)). In such instances, the one or at least one accessible amine group can be present in the core polysaccharide part of O-PS-core. For example, the O-PS-core polysaccharide can include one or at least one (e.g., 1, 2, 3, 4, 5, 6, 7, 8, 9, 10, 10-20, 20-30, or more) of *Escherichia coli* O-PS-Core, *Shigella* O-PS-Core, *Enterobacteriaceae* O-PS-Core, *Pseudomonas* sp. O-PS-Core, *P. aeruginosa* O-PS-Core, *Moraxella* sp. O-PS-Core, *Helicobacter* O-PS-Core, *Stenotrophomonas* O-PS-Core, *Bdellovibrio* O-PS-Core, acetic acid bacteria O-PS-Core, *Legionella* O-PS-Core, *Wolbachia* O-PS-Core, cyanobacteria O-PS-Core, *Spirochaetes* O-PS-Core, green sulfur bacteria O-PS-Core, green non-sulfur bacteria O-PS-Core, *Neisseria* sp. O-PS-Core, *N. gonorrhoeae* O-PS-Core, *Meningitis* sp. O-PS-Core, *N. meningitides* O-PS-Core, *Moraxella* O-PS-Core, *M. catarrhalis* O-PS-Core, *Hemophilus* sp. O-PS-Core, *H. influenza* O-PS-Core, *Klebsiella* sp. O-PS-Core, *K. pneumonia* O-PS-Core, *Legionella* sp. O-PS-Core, *L. pneumophila* O-PS-Core, *Proteus mirabilis* O-PS-Core, *Enterobacter cloacae* O-PS-Core, *Serratia marcescens* O-PS-Core, *Helicobacter* sp. O-PS-Core, *H. pylori* O-PS-Core, *Salmonella* sp. O-PS-Core, *S. enteritidis* O-PS-Core, *Salmonella typhi* O-PS-Core), *Acinetobacter baumannii* O-PS-Core, *V. cholera* O-PS-Core, *V. cholerae* Inaba O-PS-Core, or *V. cholerae* Ogawa O-PS-Core, or antigenic fragments of the one or more O-PS-core polysaccharides, or any combination thereof. In some aspects, the one or more O-PS-core polysaccharides can be *V. cholerae* O-PS-Core, or antigenic fragments of *V. cholerae* O-PS-Core. In other aspects, the one or more O-PS-core polysaccharides can be *V. cholerae* Inaba O-PS-Core, or antigenic fragments of *V. cholerae* Inaba O-PS-Core. In further aspects, the one or more O-PS-core polysaccharides can be *V. cholerae* Ogawa O-PS-Core, or antigenic fragments of *V. cholerae* Ogawa O-PS-Core.

As noted above, in the conjugate molecules P is an amine group containing protein. In some aspects, such proteins can include carrier (e.g., carrier-like) proteins or peptides. Such proteins can include, for example, Keyhole Limpet Hemocyanin; serum proteins such as transferrin, bovine serum albumin, human serum albumin, chicken serum albumin, thyroglobulin or ovalbumin, immunoglobulins, or hormones, such as insulin or palmitic acid; dextrans like sepharose; the outer membrane protein complex of *Neisseria meningitides* (OMPC); tetanus, diphtheria, or LPF toxoid; hepatitis B surface antigen or core antigen; rotavirus capsid protein; or the L1 protein of bovine or human papillomavirus VLP, or fragments of any one of the aforementioned proteins. In other aspects, proteins can include recombinant tetanus Toxin Hc fragment, or fragments of recombinant tetanus Toxin Hc fragment. In further aspects, proteins can include CRM197 (e.g., recombinant Diphtheria CRM197), or fragments of CRM197.

In some embodiments, the disclosure provides conjugate molecules including an O-PS-Core polysaccharide coupled directly to a carrier protein, wherein the O-PS-Core polysaccharide is coupled directly to a carrier protein via the following bond:

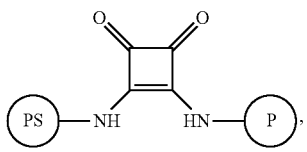

where: PS refers to the O-PS-core polysaccharide and P refers to the carrier protein; where the amine shown bonded to PS is an amine present (e.g., inherently or naturally present) in the core polysaccharide of O-PS-core; and where the amine shown bonded to P is part of P.

In some embodiments, the disclosure provides processes or methods of manufacturing conjugate molecules (e.g., vaccines). Such methods can include, for example: treating one or at least one (e.g., 1, 2, 3, 4, 5, 6, 7, 8, 9, 10, 10-20, 20-30, or more polysaccharides) polysaccharide, having (e.g., inherently or naturally containing) one or at least one accessible amine group, with an alkyl squarate in the presence of a first buffer to manufacture a polysaccharide squarate monoester; and treating the polysaccharide squarate monoester with a protein in the presence of a second buffer to manufacture a conjugate molecule. In some instances, the one or at least one polysaccharide can include a bacterial O-PS-core polysaccharide in which the amine is present (e.g., inherently or naturally present) in the core polysaccharide of the O-PS-core. In some aspects, the methods can result in conjugate molecules that include:

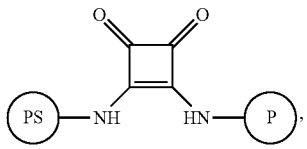

where: PS refers to the O-PS-core polysaccharide and P refers to the carrier protein; where the amine shown bonded to PS is an amine present (e.g., inherently or naturally present) in the core polysaccharide of O-PS-core; and where the amine shown bonded to P is part of P.

In some aspects, the methods include a first buffer with a pH of or of about pH 7.0. Such first buffers can include or can be phosphate buffers. In other aspects, the methods include a second buffer with a pH of or of about pH 9.0. Such buffers can include or can be borate buffers. In some aspects, the alkyl squarate of the conjugation process can be dimethyl squarate, diethyl squarate, dipropyl squarate, dibutyl squarate, and/or didecyl squarate.

In some aspects, the molar ratio of polysaccharides to alkyl squarate can be between about 1:1 to about 50:1, including any range there between (e.g., about 1:1 to 40:1, 30:1, 20:1, 10:1, 5:1, 2:1; 2:1 to about 50:1, 40:1, 30:1, 20:1, 10:1; 5:1 to about 25:1), or a ratio of about 1:1; 2:1, 5:1, 10:1, 15:1, 20:1, 21:1, 25:1, 30:1, 40:1, 50:1, or More than about 50:1.

In other aspects, the molar ratio of polysaccharide squarate monoester to protein is between about 1:1 to about 50:1 or any range there between (e.g., about 1:1 to 40:1, 30:1, 20:1, 10:1, 5:1, 2:1; 2:1 to about 50:1, 40:1, 30:1, 20:1, 10:1; 5:1 to about 25:1), or a ratio of about 1:1; 2:1, 5:1, 10:1, 15:1, 20:1, 21:1, 25:1, 30:1, 40:1, 50:1, or more than about 50:1.

In some embodiments, the disclosure provides compositions containing one or more glycoconjugate antigens prepared by the conjugation process.

In another aspect, the invention features methods of inducing an immune response in a subject, the method comprising administering to the subject a conjugate vaccine described herein in an amount effective to induce an immune response in the subject.

In a further aspect, the invention provides methods for inducing an immune response in a subject, e.g., an anti-cholera immune response. The methods include administering to a subject a conjugate vaccine in which an O-PS-core antigen of *V. cholerae* O1 is directly conjugated to a Tetanus Toxin heavy chain (TThc), e.g., SEQ ID NO:3, in an amount effective to induce an immune response in the subject.

Also provided herein is the use of a conjugate vaccine described herein for inducing an immune response in a subject. In some embodiments, the invention provides the use of a conjugate vaccine in which the O-PS-core antigen of *V. cholerae* O1 is directly conjugated to a Tetanus Toxin heavy chain (TThc), e.g., SEQ ID NO:3, for inducing an immune response in a subject, e.g., an anti-cholera immune response. Furthermore, the invention provides the use of a conjugate vaccine described herein, e.g., a conjugate vaccine in which the O-PS-core antigen of *V. cholerae* O1 is directly conjugated to a Tetanus Toxin heavy chain (TThc), e.g., SEQ ID NO:3, in the manufacture of a medicament for the induction of an immune response, e.g., an anti-cholera immune response, e.g., for the treatment or prevention of cholera.

As used herein, an "anti-cholera immune response" refers to the induction of cholera-specific antibodies (i.e., antibodies that specifically recognize *V. cholerae*) in a subject, e.g., antibodies that treat or provide protection against the development of cholera.

In some embodiments, the subject has been, may be, or is likely to be exposed to cholera, e.g., to *V. cholerae*. In some embodiments, the subject lives in or will be traveling to a region in which cholera is common or endemic.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 12 shows structures of the O-Specific Polysaccharides of *Klebsiella*.

FIG. 14 shows structures of the O-Specific Polysaccharides of *Pseudomonas aeruginosa*. D-ManImu=2,3-(1-acetyl-2-methyl-2-imidazolino-5,4)-2,3-dideoxy-D-mannuronic acid; D-Man(NAc)$_2$U=2,3-diacetamido-2,3-dideoxy-D-mannuronic acid; D-QuinAc=N-acetal-D-quinovosamine.

FIG. 21 provides an exemplary sequence of *Clostridium tetani* tetanus toxin gene (SEQ ID NO:1). Underlining represents a fragment of the heavy chain used in Examples 6 and 7.

FIG. 22 provides an exemplary sequence of a nucleotide sequence encoding a *C. tetani* tetanus toxin heavy chain C terminal fragment (SEQ ID NO:2). Underlined sequences are derived from primers described in Example 6.

FIG. 23 provides an exemplary sequence of a *C. tetani* tetanus toxin heavy chain C terminal fragment (SEQ ID NO:3). Underlined sequences are derived from/encoded by sequence added by primers described in Example 6.

FIGS. 24A-F is a series of six bar graphs showing mean normalized IgG, IgM, and IgA responses in plasma of patients infected with *V. cholerae* O1 Ogawa or Inaba to Inaba OSPc:BSA (OSP) and lipopolysaccharide (LPS). Plasma IgG, IgM, and IgA response to Inaba OSP and LPS in Inaba (A, C, E) and Ogawa (B, D, F) infected patients. Asterisks indicate a statistically significant difference ($P\leq0.05$) from baseline (day 2) levels within a particular antigen group.

FIGS. 25A-F is a series of six bar graphs depicting mean normalized IgG, IgM, and IgA responses in plasma of patients infected with *V. cholerae* O1 Ogawa or Inaba to Ogawa OSPc:BSA (OSP) and lipopolysaccharide (LPS). Plasma IgG, IgM, and IgA response to Ogawa OSP and LPS in Inaba (A, C, E) and Ogawa (B, D, F) infected patients. Asterisks indicate a statistically significant difference ($P\leq0.05$) from baseline (day 2) levels within a particular antigen group.

FIGS. 26A-D is a series of four line graphs showing correlation between vibriocidal antibody responses and plasma IgG or IgM antibody responses to OSPc:BSA (OSP) and lipopolysaccharde (LPS). The lines indicate the correlations between the different responses to OSP and LPS, and the vibriocidal antibody response.

Figure 27:
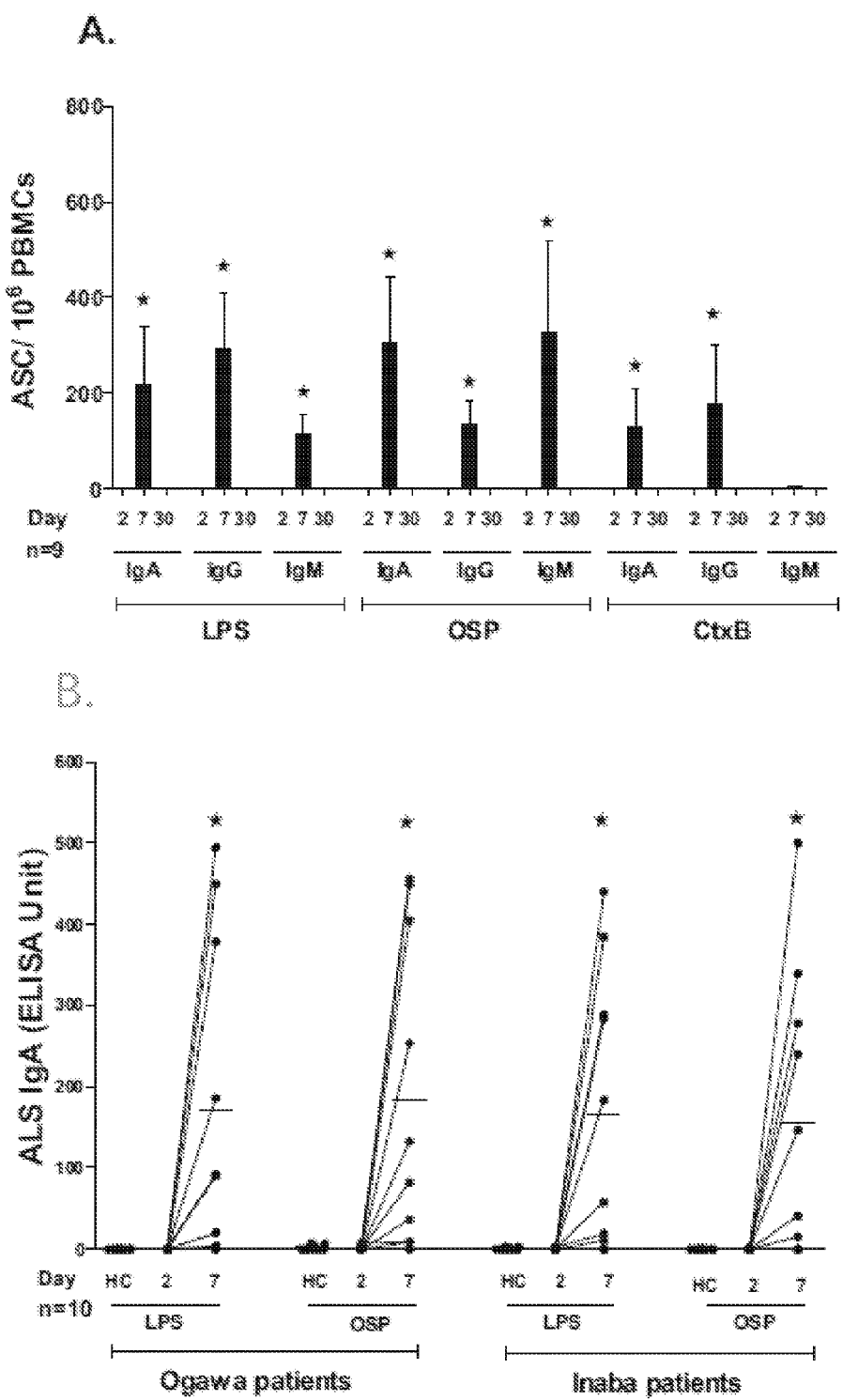

FIGS. 27A-B is a series of bar graphs and line graphs depicting mucosal immune responses to Ogawa OSPc:BSA (OSP) and lipopolysaccharide (LPS). Asterisks indicate a statistically significant difference (P≤0.05) from baseline (day 2). (A) Mean circulating antigen-specific IgG, IgM, and IgA ASC responses to Ogawa OSP, LPS and CTB with standard error bars. (B) ALS IgA responses to Ogawa OSP and LPS in healthy controls, and Ogawa and Inaba patients.

FIGS. 28A-B is a series of bar graphs showing antigen-specific inhibition of vibriocidal antibody assays using OSP-c:BSA (OSP) and lipopolysaccharde (LPS). Ag-represents patient plasma not incubated with antigen. BSA and rCTB antigens were also assayed at concentrations of 1, 10, and 100 μg/mL and no inhibition was detected. The *V. cholerae* O1 Ogawa OSPc:BSA and Ogawa LPS were used for these experiments.

DETAILED DESCRIPTION

Due to their T cell independent nature, polysaccharides are often poorly immunogenic. Therefore, efforts have been made to couple polysaccharides to protein carriers to increases T cell activation. This markedly improves the magnitude and duration of immune responses following immunization. A number of anti-bacterial conjugate vaccines are now in wide use in humans, including the pneumococcal, meningococcal and *Haemophilus influenzae* b conjugate vaccines (Claesson et al., Ped Inf Dis J 1991; 10(8):560-4). Most of the methods to make conjugate vaccine require chemical modification of the carbohydrate antigen to make it amenable to conjugation. Described herein are methods using squaric acid chemistry to produce a conjugate vaccine attaching directly to core antigen, without an intervening linker. Using this strategy the present inventors have developed an OSP-TT conjugate vaccine and have showed its immunogenicity in mice.

Conventional techniques for conjugating polysaccharides, synthetic or otherwise, to carriers, such as proteins, generally include multiple steps in which one or both of the polysaccharide and/or the carrier are first modified (e.g., chemically), for example, by addition of one or more linkers and/or deacylation. Such modified species are subsequently conjugated using additional chemistry. (For examples of conventional polysaccharide to protein conjugation techniques see U.S. Pat. No. 7,588,765, Grandjean et al., Glycoconj. J., 26:41-55, 2009; Gupta et al., Infect. Immun. 60:3201-3208, 1992; Hermanson, Bioconjugate Techniques, Academic Press, New York, 1996; Bundle, Caister Academic Press, 2011). Previous reports suggested that steric hindrance precluded direct conjugation, e.g., without the addition of linkers of polysaccharides to proteins (Grandjean et al., Glycoconj. J., 26:41-55, 2009).

The present disclosure is based, inter alia, on the surprising discovery that squaric acid chemistry can be used to conjugate free amine inherently present and accessible in the core oligosaccharide of the bacterial polysaccharide, lipopolysaccharide (LPS), directly to amine groups present in protein without the addition of chemical linkers to the polysaccharide or the protein and/or without otherwise modifying either the polysaccharide or the protein, e.g., to promote conjugation; and/or the discovery that conjugate compositions resulting from this method are immunogens.

While the disclosure exemplifies such methods using conjugation of bacterial polysaccharides to proteins, e.g., to produce conjugate vaccines, one skilled in the art will appreciate that the disclosure relates to and can be used for methods for directly conjugating any polysaccharide (as used herein, polysaccharide refers to polysaccharides and oligosaccharides, including bacterial lipopolysaccharide (LPS)), that include one or at least one accessible amine group (e.g., present within LPS core polysaccharide or core-like polysaccharide) to a second amine containing species (e.g., a protein) without addition of chemical linkers and/or without otherwise modifying either species, e.g., to promote conjugation. Advantages of the present disclosure, e.g., relative to conjugation methods known in the art, include, inter alia, reduced cost, reduced complexity, and increased reproducibility. For example, the methods offer reduced complexity as once a polysaccharide that includes inherent free amine has been identified or selected, the polysaccharide can be easily conjugated to any other amine containing molecule (e.g., a carrier protein) without the need to modify either component (as described below, current conjugation methods generally require at least one modification (e.g., addition of a chemical linker) be made to at least the polysaccharide). Increased reproducibility is afforded by not having to modify the polysaccharide or the protein, which modification can result in unintended or undesirable changes in the polysaccharide and/or the protein, e.g., during a manufacturing process and/or between different batches or lots.

The methods herein have application, for example, in the production or manufacture of conjugate compositions. For example, the methods can be used in the production or manufacture of conjugate vaccines (e.g., anti-bacterial, anti-viral, anti-AIDS, and/or anti-cancer vaccines) and/or conjugate ligands.

Conjugation Methods

In general, methods herein include: (i) selection of a polysaccharide that includes one or at least one accessible amine group (e.g., present within LPS core polysaccharide or core-like polysaccharide) and an amine containing carrier (e.g., a protein) for conjugation; (ii) squaric acid diester treatment of at least the polysaccharide to generate a squaric acid monoester derivative of the polysaccharide; and (iii) reaction of the monoester with the carrier to thereby conjugate the polysaccharide directly to the carrier. Each of (i)-(iii) can include additional treatments. For example, (ii) can include purification of the monoester (e.g., to remove untreated species or excess of squaric acid diester), e.g., using methods known in the art, such as ultrafiltration and/or chromatography. (iii) can include monitoring conjugation of the monoester with the carrier (e.g., using SELDI-TOF mass spectrometry) and controlling the rate of conjugation (e.g., by varying the ratios or proportions of monoester to carrier, and/or concentration of the monoester and/or the carrier). Such methods also facilitate termination of the conjugation reaction when a desired polysaccharide to protein ratio has been achieved. Such techniques can be useful, for example, in the production of monovalent and multivalent conjugate vaccines. Recitation of (i)-(iii) does not imply that each of (i)-(iii) must be performed and does not indicate order. Rather, methods can include (i)-(iii) or (ii), or (ii)-(iii) and each such embodiment can be performed sequentially or together. For example, where methods include (ii) and (iii), (ii) and (iii) can be performed sequentially as (ii) then (iii) or together. Furthermore, steps (i), (ii), and/or (iii) can be performed by a single entity or multiple entities. The following description relates to (ii) and (iii) above.

The following techniques can be used for the conjugation of species (e.g., polysaccharides) containing one or at least one accessible amine group to an amine containing carrier.

A protein can be conjugate directly to polysaccharides containing one or at least one amino group (e.g., present within LPS core polysaccharide or core-like polysaccharide) 1, by treatment (e.g., sequential) of the polysaccharide 1 with dialkyl squarate 2, to generate a squaric acid monoester derivative of the polysaccharide, followed by exposure of the monoester to the protein of interest 3. The resulting conjugate 4 has no linker moiety other than the squaramide unit depicted in 4. The different dialkyl squarates would vary in their reactivity towards the amine group of the polysaccharide and also towards the protein of interest.

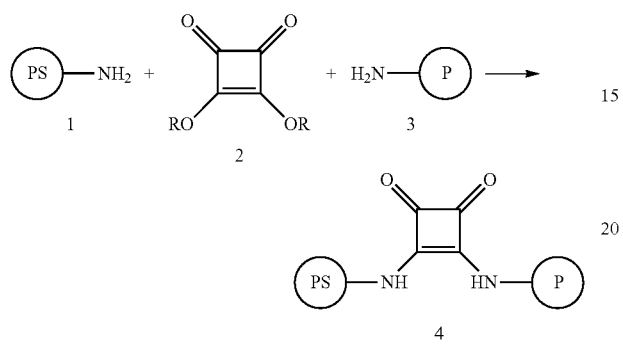

In some embodiments, the dialkyl squarate is dimethyl squarate, diethyl squarate, dipropyl squarate, dibutyl squarate, or didecyl squarate. The dialkyl squarates can be replaced with similar molecules which could lead to squaramide 4. Such molecules could be similar to the squarates 2, but replacing the di-alkoxy groups with leaving groups known to one of skill in the art. In some embodiments, the leaving group can be selected from alkylsulfonyl (e.g., methanesulfonyl), haloalkylsulfonyl (e.g., trifluoromethanesulfonyl), arylsulfonyl (e.g., toluenesulfonyl), and the like. In other embodiments the leaving group can be chloride or bromide.

The squaric acid monoester can be reacted with carrier protein 3 in aqueous media under appropriate pH conditions, e.g., from pHs ranging from about 3 to about 8, about 3 to about 7, or about 4 to about 6.5. In some embodiments, the above reaction could be carried at a pH of about 5, e.g., about 6, about 7, about 8, about 9, or even about 10. The squarate monoalkyl ester can couple to a target carrier protein at a pH of from about 4 to about 12, e.g., from about 6 to about 10, from about 7 to about 11, from about 8 to about 10, or from about 9 to about 10. In some embodiments, the above reaction could be carried at a pH of about 5, e.g., about 6, about 7, about 8, about 9, about 10, about 11, or even about 12. Typically, lower pHs can be used, e.g., from 4 to about 5.75, for preferential covalent attachment to the N-terminus. Thus, different reaction conditions (e.g., different pHs or different temperatures) can result in the attachment of a polysaccharide to different locations on the carrier protein (e.g., internal lysines versus the N-terminus). Coupling reactions can often be carried out at room temperature, although lower temperatures may be required for particularly labile carrier protein moieties. Reaction times are typically on the order of hours, e.g., about 1 hour, about 2 hours, about 4 hours, about 8 hours, about 12 hours, about 16 hours, about 20 hours, about 24 hours, about 36 hours, about 48 hours, about 72 hours, about 96 hours, or even about 240 hours, depending upon the pH and temperature of the reaction. Varying ratios of polysaccharide to carrier protein may be employed, e.g., from an equimolar ratio up to a 40-fold molar excess of polysaccharide. Typically, up to a 10-20 fold molar excess of polysaccharide would suffice. In some embodiments, the polysaccharide is used in a molar excess of e.g., about 2-fold, about 4-fold, about 6-fold, about 8-fold, about 10-fold, about 12-fold, about 14-fold, about 16-fold, about 18-fold, about 20-fold, about 25-fold, or about 30-fold.

As used herein, the phrase 'conjugate directly to' means that the one or at least one amine in the polysaccharide (e.g., an amine present within LPS core polysaccharide or core-like polysaccharide when the polysaccharide is LPS) is connected (e.g., covalently) to an amine in the carrier via the following bond:

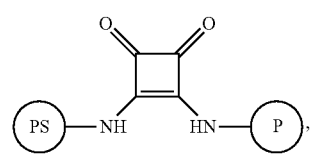

where PS refers to polysaccharide and P refers to protein and where the amine shown bonded to PS and P are part of PS and P. The phrase can also exclude the presence of the following chemical linkers:

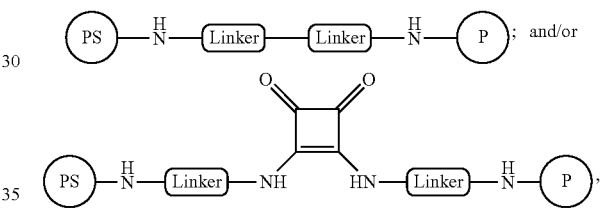

again where PS refers to polysaccharide and P refers to protein.

Polysaccharides for use in the methods herein, e.g., polysaccharides that include one or at least one inherent and/or accessible amine group (e.g., an amine present within LPS core polysaccharide or core-like polysaccharide), can include naturally occurring and synthetically generated polysaccharides. An accessible amine group can be naturally or inherently present and/or accessible in the macromolecule (e.g., an amine present within LPS core polysaccharide or core-like polysaccharide), artificially or synthetically incorporated in the macromolecule (e.g., an amine that is artificially or synthetically present within LPS core polysaccharide or core-like polysaccharide), and/or artificially exposed (e.g., via deacylation) (e.g., an amine that is artificially exposed within LPS core polysaccharide or core-like polysaccharide).

Polysaccharides can be immunogenic or non-immunogenic (e.g., mildly or weakly immunogenic) and can be derived from pathogenic or non-pathogenic sources. For example, polysaccharides can be bacterial, viral, fungal, parasitic, and/or mammalian. In some instances, amine-containing species can be synthetic or recombinant.

As noted above, the methods disclosed herein can be used to conjugate polysaccharides that include one or at least one accessible amine group (e.g., an amine present within LPS core polysaccharide or core-like polysaccharide) directly to a carrier that includes amine (e.g., a protein). Accordingly, the disclosure includes methods for producing or manufacturing conjugate vaccines.

Carbohydrates and/or polysaccharides present certain properties that can limit their standalone use as vaccines. These properties can include no overt requirement for the presence of T cells to induce an immune response, dominance of IgM, failure to induce memory post-immunization, an absence of affinity maturation post-immunization, poor immunogenicity in infants, the elderly, and the immunocompromised (see, e.g., Goldblatt, Clin Exp Immunol., 119:1-3, 1990; Goldblatt, J. Med. Microbiol., 47:563-567, 1998). Conjugation of polysaccharides to a protein carrier, resolves these issues. Numerous conjugate vaccines, containing a carbohydrate or polysaccharide antigen and a carrier protein are currently approved by the U.S. Federal Drug Administration (FDA). See, below.

The methods herein include conjugating a polysaccharide or candidate polysaccharide that has one or at least one accessible amine group directly to a carrier comprising an amine group. If the polysaccharide is a candidate polysaccharide, methods can further include assessing the immunogenicity of the polysaccharide to identify the polysaccharide as an immunogenic polysaccharide. Such methods can include assessment of whether the polysaccharide promotes antibody production. See, methods described below.

As used herein, polysaccharides can be native (or mimetics thereof), synthetic, and/or recombinant polysaccharides, including fragments of polysaccharides. In some instances, the polysaccharides can be immunogenic or antigenic (e.g., including mildly immunogenic or antigenic in certain subjects, e.g., adults, and/or immunogenic when coupled to a carrier) against the organism or cell from which they were obtained or derived. For example, an immunogenic polysaccharide obtained from a particular bacterial strain can be immunogenic or antigenic against the bacterial strain from which it was obtained or derived. Immunogenic polysaccharides can be polysaccharides, or fragments (e.g., antigenic fragments) thereof, that promote an immune (e.g., antibody) response in a subject or host. Such an immune response can be transient or long term. The immune response can include production of antibodies by the subject or host, which antibodies immunoreact (e.g., that specifically immunoreact or bind specifically) to the immunogenic polysaccharide and/or the organism or cell from which they were obtained or derived.

In some instances, polysaccharides can be bacterial polysaccharides, or antigenic fragments thereof, that have one or at least one accessible amine group. Such polysaccharides can include, for example, polysaccharides, or fragments thereof, from capsular and/or non-capsular bacteria, including, Gram-negative, Gram-positive, and Gram-indeterminate bacteria. Bacterial polysaccharides, or antigenic fragments thereof, can be or can be obtained, purified, and/or isolated from, for example, bacterial lipopolysaccharides (LPS), bacterial capsular polysaccharides (CP), bacterial peptidoglycan, and bacterial exopolysaccharides. In certain instances, the polysaccharide can be a bacterial polysaccharide or a fragment thereof from a non-capsular bacterial organism.

Bacterial polysaccharides, or fragments thereof, can be obtained, purified, and/or isolated from Gram-negative bacteria, including, but not limited to, e.g., proteobacteria (*Escherichia coli, Salmonella* sp., *Shigella*, and other *Enterobacteriaceae, Pseudomonas* sp. (e.g., *P. aeruginosa*), *Moraxella* sp., *Helicobacter, Stenotrophomonas, Bdellovibrio*, acetic acid bacteria, *Legionella, Wolbachia*), cyanobacteria, *Spirochaetes*, green sulfur and green non-sulfur bacteria, Gram-negative cocci (e.g., *Neisseria* sp. (e.g., *N. gonorrhoeae*), *Meningitis* sp. (e.g., *N. meningitidis*), and *Moraxella* (e.g., *M. catarrhalis*)), bacilli (e.g., *Hemophilus* sp. (e.g., *H. influenza*), *Klebsiella* sp. (e.g., *K. pneumonia*), *Legionella* sp. (e.g., *L. pneumophila*), *Proteus mirabilis, Enterobacter cloacae, Serratia marcescens, Helicobacter* sp. (e.g., *H. pylori*), and *Salmonella* sp. (e.g., *S. enteritidis, Salmonella typhi*), and *Acinetobacter baumannii*).

LPS, also known as lipoglycans, are macromolecules commonly found on the surface of Gram-negative bacteria that include a lipid (i.e., Lipid A) joined to a polysaccharide by a covalent bond. The LPS polysaccharide includes an O-polysaccharide (O-PS), also referred to as the O-specific polysaccharide (O-SP) and O-antigen, and a core oligosaccharide, which includes inner core and outer core domains. Structurally, Lipid A, the toxic component of LPS and the innermost domain of LPS, anchors LPS to the bacterial cell wall and connects to O-PS, the outermost domain of LPS, via the intermediate core oligosaccharide. The LPS polysaccharide (e.g., core and O-PS) extends into the bacterial environment and is a virulence factor and the major protective antigen of *Vibrio cholerae* and many other bacterial pathogens. O-PS is a repetitive glycan polymer whose composition varies between bacterial strains. Thus, O-PS is strain specific and can serve as a target for immune recognition. Complete LPS molecules are normally not used as components of vaccines because the Lipid A component of the molecule exhibits toxicity. In some instances, an immunogenic polysaccharide can be polysaccharide obtained from LPS, which polysaccharide includes O-PS and core (e.g., O-PS-core). In such cases, the amine present within LPS core polysaccharide is conjugate to an amine present in a carrier. Methods for obtaining LPS from bacterial organisms and for obtaining O-PS-Core from LPS are known in the art.

Methods for obtaining, purifying, and/or isolating LPS from bacteria are exemplified herein and are known in the art (see, e.g., Westfal et al., Methods Carbohydr. Chem., 5:83-91, 1965). Such methods can include obtaining a capsular or non-capsular bacterial cell (e.g., an isolated bacterial cell) and/or a bacterial cell culture, pelleting the cell or cells, and processing the cell or cells using hot phenol/water extraction followed by enzymatic treatment and centrifugation, and obtaining isolated LPS.

Methods for detoxifying LPS and/or for removing Lipid A from LPS are known in the art and are exemplified herein (see, e.g., Raziuddin, Inf. and Immunol., 27:275-280, 1980; Gustafsson, Infect. Immunol., 49:275-280, 1985). For example, Lipid A removal can include enzymatic and/or chemical removal of Lipid A Gom the LPS and subsequent isolation of liberated polysaccharide. For example, LPS can be hydrolyzed using aqueous acetic acid. Hydrolysates can be separated into chloroform soluble (Lipid A containing) and water soluble (polysaccharide containing) fractions by centrifugation. Further fractionation of LPS polysaccharide can be performed chromatographically, e.g., to obtain O-PS-Core. O-PS-Core can be further purified, e.g., to remove low molecular weight contaminants, using ultrafiltration and/or dialysis.

In some instances, the bacterial polysaccharide, or fragment thereof, can be O-PS-Core, or a fragment thereof, obtained from LPS of *E. coli, Shigella, Campylobacter* sp., *Pseudomonas* sp., and/or *Vibrio Cholerae* (e.g., *V. cholerae* O1, serotypes Inaba or Ogawa. For example, the bacterial polysaccharide can be O-PS-Core of FIG. 1A, e.g., a chain of (1→2)-α-linked moieties of 4-amino-4,6-dideoxy-α-D-mannopyranose (perosamine), wherein the amino group of which is acylated with 3-deoxy-L-glycero-tetronic acid, and/or wherein the terminal upstream perosamine moiety can include a methoxy group at 2. Alternatively or in addition, the bacterial polysaccharide can be O-PS-Core, or a fragment of O-PS-Core, disclosed in N. A. Komandrova, R. P. Gorshkova, and Yu. S. Ovodov, "Specific Polysaccharides of the Lipopolysaccharides of Gram-Negative Bacteria." Chem Nat Compd 22(5): 497-511, 1986. DOI: 10.1007/BF00599250. Alternatively or in addition, the bacterial polysaccharide can be O-PS-Core, or a fragment of O-PS-Core, shown in FIGS. 8-17.

Carrier proteins can include any protein that includes one or more amines that can be conjugate to a polysaccharide disclosed herein. If the protein is for use in a conjugate vaccine, then the protein can be a protein that increases or enhances the immunogenicity of polysaccharide. Carriers that fulfill these criteria are described in the art (see, e.g., Fattom et al., Infect. Immun., 58:2309-2312, 1990; Devi et al., Proc. Natl. Acad. Sci. USA 88:7175-7179, 1991; Li et al., Infect. Immun. 57:3823-3827, 1989; Szu et al., Infect. Immun. 59:4555-4561, 1991; Szu et al., J. Exp. Med. 166:1510-1524, 1987; and Szu et al., Infect. Immun. 62:4440-4444, 1994). Polymeric carriers can be a natural or a synthetic material containing one or more primary and/or secondary amino groups, azido groups, or carboxyl groups. The carrier can be water soluble.

Examples of water soluble peptide carriers include, but are not limited to, natural or synthetic peptides or proteins from bacteria or virus, e.g., tetanus toxin/toxoid, diphtheria toxin/toxoid, *Pseudomonas aeruginosa* exotoxin/toxoid/protein, pertussis toxin/toxoid, *Clostridium perfringens* exotoxins/toxoid, and hepatitis B surface antigen and core antigen. Variants or mutants of these peptides, derived for example by amino acid substitution or deletion, may also be employed as carriers. Example of water insoluble carriers can include, but are not limited to, aminoalkyl-SEPHAROSE™ (cross-linked agarose), e.g., aminopropyl or aminohexyl SEPHAROSE™ (cross-linked agarose), and aminopropyl glass and the like. Other carriers may be used when an amino or carboxyl group is added through covalent linkage with a linker molecule. In some embodiments, the carrier protein is from the same organism as the polysaccharide (e.g., the O-PS-Core).

In some instances, the carrier can include any protein carrier that meets the requirements set forth by, or that is approved for use by, the FDA or the World Health Organization (WHO) (see, e.g., Document WHO/BS/06.2041—Final, which includes guidelines adopted by WHO at the 57$^{th}$ meeting of the WHO Expert Committee on Biological Standardization, Oct. 23-27, 2006). For example, amine containing carriers can include: chicken serum albumin, Keyhole Limpet Hemocyanin; serum proteins such as transferrin, bovine serum albumin, human serum albumin, thyroglobulin, or ovalbumin, immunoglobulins, or hormones, such as insulin or palmitic acid; dextrans like SEPHAROSE™; the outer membrane protein complex of *Neisseria meningitides* (OMPC); tetanus, diphtheria, or LPF toxoid; hepatitis B surface antigen or core antigen; rotavirus capsid protein; or the L1 protein of bovine or human papillomavirus VLP, or fragments of any of the aforementioned proteins.

Figure 21:
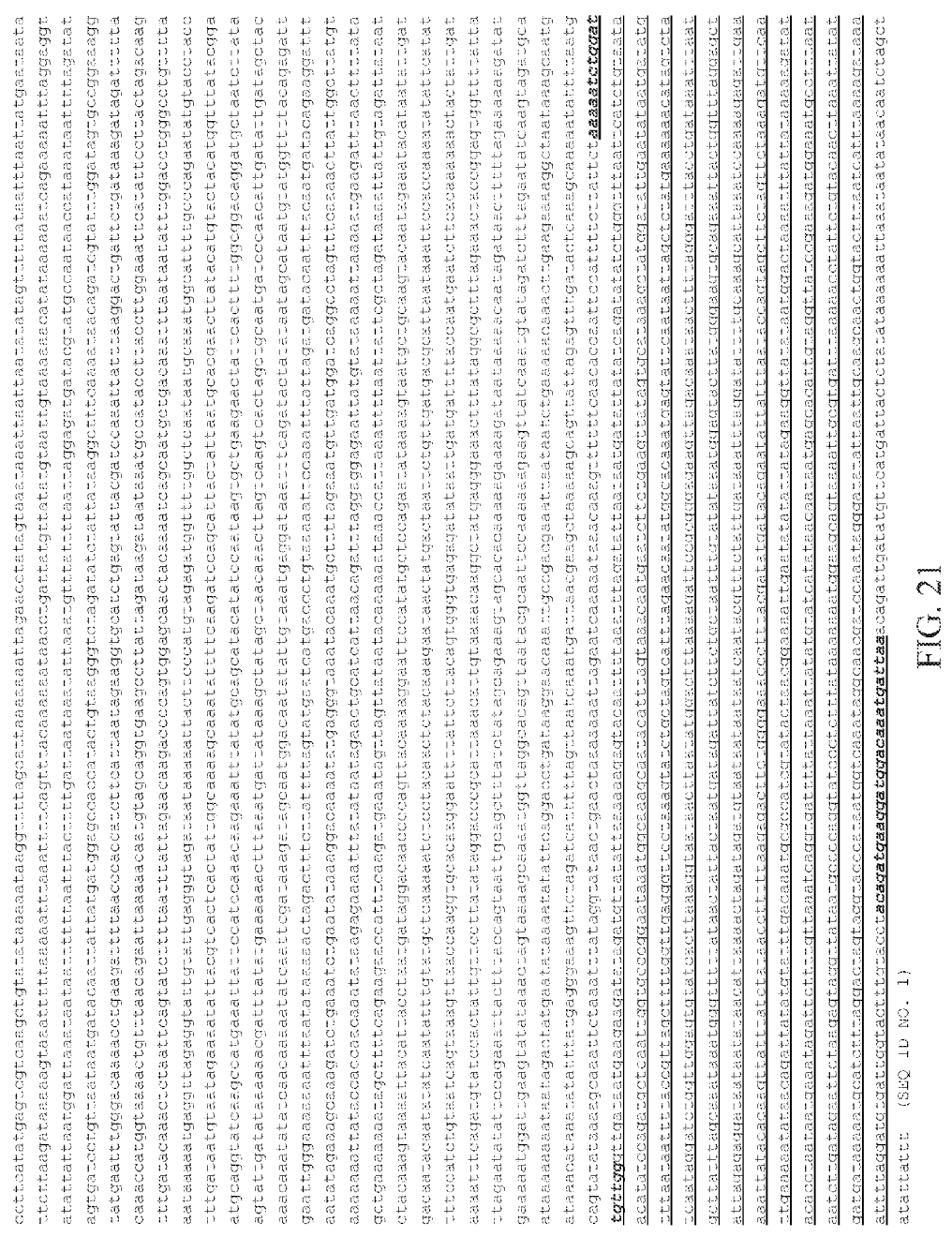

In a preferred embodiment, the carrier is tetanus toxin or an antigenic fragment thereof. The sequence of tetanus toxin is set forth in Fairweather and Lyness. Nucl. Acids Res. 14(19):7809-7812 (1986) and in GenBank at Accession No. X06214.1, and is also shown in FIG. 21. See, e.g., Bongat et al., Glycoconjugate J., 27: 69-77, 2010; and Figueiredo et al., Infection and Immunity, 63(8):3218-3221 (1985). In some instances, the carrier can be tetanus toxin C-fragment (TETC, S2Kd fragment, obtained by papain treatment of tetanus toxin). In some instances, the carrier can comprise the receptor binding domain of tetanus toxin, e.g., a fragment comprising a sequence encoded by nucleotides 2914-4269 of SEQ ID NO:1; see, e.g., Bongat et al., Glycoconjugate J., 27: 69-77, 2010, e.g., SEQ ID NO:3. In some instances, the amine containing carrier protein can be recombinant tetanus Toxin Hc fragment (see, e.g., Louch et al., Biochem., 41:13644-13652, 2002). In some instances, the amine containing carrier protein can be recombinant Diphtheria $CRM_{197}$.

Thus, in some instances, (i) selection of a polysaccharide that includes one or at least one inherent free or accessible amine group and an amine containing carrier (e.g., a protein) for conjugation, disclosed above, can include: selecting or obtaining a bacterial organism (e.g., an isolated bacterial organism); obtaining a polysaccharide or LPS from the organism; and obtaining O-PS-Core from the LPS. For example, methods can include: (i) obtaining O-PS-Core polysaccharide from one or more of *Escherichia coli, Salmonella* sp., *Shigella*, and other *Enterobacteriaceae, Pseudomonas* sp. (e.g., *P. aeruginosa*), *Moraxella* sp., *Helicobacter, Stenotrophomonas, Bdellovibrio*, acetic acid bacteria, *Legionella, Wolbachia*), cyanobacteria, *Spirochaetes*, green sulfur and green non-sulfur bacteria, *Neisseria* sp. (e.g., *N. gonorrhoeae*), *Meningitis* sp. (e.g., *N. meningitidis*), and *Moraxella* (e.g., *M. catarrhalis*), *Hemophilus* sp. (e.g., *H. influenza*), *Klebsiella* sp. (e.g., *K. pneumonia*), *Legionella* sp. (e.g., *L. pneumophila*), *Proteus mirabilis, Enterobacter cloacae, Serratia marcescens, Helicobacter* sp. (e.g., *H. pylori*), and *Salmonella* sp. (e.g., *S. enteritidis, Salmonella typhi*), and *Acinetobacter baumannii*), and obtaining an amine containing carrier (e.g., a protein) for conjugation; (ii) squaric acid chemistry treatment of at least one or more of the O-PS-Core obtained in (i) to generate one or more squaric acid monoester derivatives of the O-PS-Core; and (iii) reaction of the monoesters with the carrier to thereby conjugate the monoesters directly to the carrier. In some embodiments, O-PS-Core is *Escherichia coli* O-PS-Core, *Salmonella* sp. O-PS-Core, *Shigella* O-PS-Core, and other *Enterobacteriaceae* O-PS-Core, *Pseudomonas* sp. O-PS-Core (e.g., *P. aeruginosa* O-PS-Cores), *Moraxella* sp. O-PS-Core, *Helicobacter* O-PS-Core, *Stenotrophomonas* O-PS-Core, *Bdellovibrio* O-PS-Core, acetic acid bacteria O-PS-Core, *Legionella* O-PS-Core, *Wolbachia* O-PS-Core, cyanobacteria O-PS-Core, *Spirochaetes* O-PS-Core, green sulfur bacteria O-PS-Core, green non-sulfur bacteria O-PS-Core, *Neisseria* sp. O-PS-Core (e.g., *N. gonorrhoeae* O-PS-Core), *Meningitis* sp. O-PS-Core (e.g., *N. meningitides* O-PS-Core), *Moraxella* O-PS-Core (e.g., *M. catarrhalis* O-PS-Core), *Hemophilus* sp. O-PS-Core (e.g., *H. influenza* O-PS-Core), *Klebsiella* sp. O-PS-Core (e.g., *K. pneumonia* O-PS-Core), *Legionella* sp. O-PS-Core (e.g., *L. pneumophila* O-PS-Core), *Proteus mirabilis* O-PS-Core, *Enterobacter cloacae* O-PS-Core, *Serratia marcescens* O-PS-Core, *Helicobacter* sp. O-PS-Core (e.g., *H. pylori* O-PS-Core), and *Salmonella* sp. O-PS-Core (e.g., *S. enteritidis* O-PS-Core, *Salmonella typhi* O-PS-Core), *Acinetobacter baumannii* O-PS-Core, and/or *V. cholerae* O-PS-Core (e.g., *V. cholerae* Inaba O-PS-Core or *V. cholerae* Ogawa O-PS-Core).

In some embodiments, the methods disclosed herein can be used in or as part of a manufacturing process to produce a conjugate vaccine. Such a manufacturing process can include, for example: producing (e.g., via fermentation) and obtaining amine containing carrier protein disclosed herein; producing (e.g., via fermentation) and obtaining bacterial polysaccharide (e.g., O-PS-Core), e.g., using methods disclosed herein; squaric acid chemistry treatment of at least the polysaccharide to generate a squaric acid monoester derivative of the polysaccharide; reaction of the monoester with the carrier to thereby conjugate the polysaccharide directly to the carrier; removal of unconjugate/unreacted species; purification to remove any unwanted contaminants; finish and fill (concentrate to final strength, dialyze into appropriate solutions, sterilize, fill as liquid or lyophilize). It will be further appreciated that the present methods can be used to produce monovalent and multivalent conjugate vaccines. Methods for conjugating multivalent vaccines, e.g., using squaric acid chemistry and synthetic linker equipped polysaccharides, are reported in the art (Bongat et al., Glycoconjugate J., 27: 69-77, 2010).

The methods herein can include producing or manufacturing currently approved conjugate vaccines wherein the polysaccharide component of the approved conjugate vaccine includes one or at least one free amine. Various examples of conjugate vaccines are currently approved, marketed, and are routinely administered in the U.S. and Europe. Examples include *Haemophilus influenzae* type b conjugate vaccines (PedvaxHIB, ActHIB, Hiberix, Comvax), Tetanus Toxoid Conjugate (Pentacel), seven-valent pneumococcal conjugate vaccine, Pneumococcal 13-valent Conjugate Vaccine (Prevnar 13), and Menigoccocal conjugates (Menveo and Menactra). Other FDA-approved conjugate vaccines can be viewed on the FDA's website (see, e.g., World Wide Web address fda.gov). Accordingly, herein are methods for producing or manufacturing one or more of *Haemophilus influenzae* type b conjugate vaccines (Pedvax-HIB, ActHIB, Hiberix, Comvax), Tetanus Toxoid Conjugate (Pentacel), seven-valent pneumococcal conjugate vaccine, Pneumococcal 13-valent Conjugate Vaccine (Prevnar 13), and Menigoccocal conjugates (Menveo and Menactra), e.g., using the methods disclosed herein.

The methods herein can also include further processing any directly conjugated vaccines to comply with the requirements set forth by, or that are approved for use by, the FDA or the WHO. See, e.g., Document WHO/BS/06.2041—Final, which includes guidelines adopted by WHO at the 57th meeting of the WHO Expert Committee on Biological Standardization, Oct. 23-27, 2006. For example, such methods can include, but are not limited to controlling bacterial purity (e.g., for polysaccharide and carrier expression), e.g., by examining individual cultures for microbial contamination prior to isolation of polysaccharide and/or carrier from the bacteria; controlling polysaccharide by testing for identity and purity of the polysaccharide; evaluation of moisture content; evaluation of polysaccharide content; evaluation of protein impurity in purified polysaccharide (in some instances, protein impurities should be less than 1% w/w of the polysaccharide, e.g., where protein levels are assessed by the method of Lowry et al. (J Biol Chem 193:265-275, 1951) using bovine serum albumin as a reference); evaluation of nucleic acid impurity (levels of contaminating nucleic acid should be less than 1% w/w by ultraviolet spectroscopy); evaluation of endotoxin content; evaluation of O-acetyl content; evaluation of consistency of molecular size distribution; control of carrier protein by testing for identity and purity of the carrier protein; evaluating the completion of conjugation and removing unconjugated species; removal of residual conjugation reagent; evaluation of the protein content of the conjugate vaccine; evaluation of the polysaccharide to carrier protein ratio; assessment of sterility; and/or assessment of toxicity. Guidelines regarding various parameters relevant for the above methods are published by the National Regulatory Authority (NRA).

Methods can also include formulating directly conjugated compounds generated using the methods disclosed herein for administration to a subject, e.g., as vaccines.

Pharmaceutical Compositions/Vaccines

The disclosure includes compositions that include one or more polysaccharides that include one or at least one accessible amine groups (e.g., as described herein) coupled directly to and an amine containing carrier (e.g., a protein), e.g., as described herein. In other words, directly conjugated compounds generated using the methods disclosed herein can be formulated as pharmaceutical compositions. Such pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Pharmaceutical compositions are typically formulated to be compatible with their intended route of administration. Examples of routes of administration include systemic and local routes of administration. Exemplary routes include, but are not limited to, parenteral, e.g., intravenous, intradermal, subcutaneous, oral (e.g., inhalation), transdermal (topical), and transmucosal, administration. Methods of formulating suitable pharmaceutical compositions for each of these routes of administration are known in the art, see, e.g., the books in the series Drugs and the Pharmaceutical Sciences: a Series of Textbooks and Monographs (Dekker, N.Y.). Pharmaceutical compositions can be included in a container, pack, or dispenser together with instructions for administration.

Compositions that include conjugate vaccines can include additional components tailored for a vaccine. In other words, directly conjugated compounds generated using the methods disclosed herein can be formulated for use as vaccines, e.g., for vaccination or immunization of a subject, and/or for sale, import into the U.S., and/or export from the U.S. Additional components tailored for vaccines can include adjuvants, preservatives, and additives. Exemplary adjuvants include agents that increase the immune response of a subject immunized with a vaccine to the vaccine, without promoting a specific immunologic response against itself. Adjuvants can include any substance that acts to accelerate, prolong, or enhance antigen-specific immune responses when used in combination with specific vaccine antigens. Specific examples can include aluminum gels, aluminum salts, squalene, acylated and deacylated saponins (see, e.g., U.S. Pat. No. 7,858,098), oil-based adjuvants, virosomes, aluminum hydroxide, QS-21, TITERMAX™ (CytRx Corp., Norcross Ga.), Freund's complete adjuvant, Freund's incomplete adjuvant, interleukin-2, thymosin, and the like. Preservatives can be included to limit or prevent microbial growth or contamination in a vaccine (e.g., a packaged vaccine). Exemplary preservatives can include, but are not limited to, Thimerosal, Benzethonium chloride (Phemerol), Phenol, 2-phenoxyethanol. Exemplary additives can include formaldehyde, human serum albumin, gelatin, antibiotics, and yeast proteins.

Effective Amounts

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

For vaccines, effective amounts include a dose that promotes antibody production in an immunized subject. Antibody production can be assessed using an antibody titer assays (e.g., as disclosed herein). For example, vibriocidal antibody titers induced by cholera vaccines are regarded as being correlated with therapeutic utility, at least for vaccines that have passed regulatory review: vibriocidal titer is the only serologic assay required by the FDA for licensure of new cholera vaccine lots (Robbins et al., Dev. Biol. Stand., 95:161-167, 1998). Antigen-specific effector and memory responses also correlate with protection.

In some instances, a vaccine composition can contain an effective, immunogenic amount of conjugate vaccine. An effective amount of conjugate vaccine conjugate per unit dose is sufficient to induce an immune response to the organism or cell from which the polysaccharide was obtained or derived. Although effective amounts can depend, among other things, on the species of subject inoculated, the body weight of the subject and the chosen inoculation regimen, effective amounts can be readily determined. In some instances, compositions can include conjugate vaccine in concentrations of, for example, about 1 micrograms to about 100 milligrams per inoculation (dose), about 3 micrograms to about 100 micrograms per dose, about 5 micrograms to about 50 micrograms, or about 5 micrograms to about 25 micrograms per dose.

An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments. For example, effective amounts can be administered at least once. In order to increase the antibody level, a second or booster (e.g., third, fourth, or more) dose may be administered, e.g., approximately 1, 2, 3, 4, 5, 6, 7, 8, 9, 10 weeks, or more after the initial injection. Subsequent doses may be administered as indicated. The use of an immunoadjuvant may increase the responses magnitude and duration. Immunization could be parenteral transcutanous, or oral, or could part of a prime boost protocol, including orally priming with oral cholera vaccine, followed by parenteral or cutenous boosting of a cholera conjugate vaccine.

Methods of Treatment

Conjugate compositions generated using the methods disclosed herein can be administered to a subject to stimulate antibody production in the subject. In some embodiments, the antibodies produced can be immunoreactive against, or can be specifically to an antigen or epitope of, one or more of *Escherichia coli, Salmonella* sp., *Shigella*, and other *Enterobacteriaceae, Pseudomonas* sp. (e.g., *P. aeruginosa*), *Moraxella* sp., *Helicobacter, Stenotrophomonas, Bdellovibrio*, acetic acid bacteria, *Legionella, Wolbachia*), cyanobacteria, *Spirochaetes*, green sulfur and green non-sulfur bacteria, *Neisseria* sp. (e.g., *N. gonorrhoeae, N. meningitidis*), *Meningitis* sp., and *Moraxella* (e.g., *M. catarrhalis*), *Hemophilus* sp. (e.g., *H. influenza*), *Klebsiella* sp. (e.g., *K. pneumonia*), *Legionella* sp. (e.g., *L. pneumophila*), *Proteus mirabilis, Enterobacter cloacae, Serratia marcescens, Helicobacter* sp. (e.g., *H. pylori*), and *Salmonella* sp. (e.g., *S. enteritidis, Salmonella typhi*), and *Acinetobacter baumannii*). For example, the conjugate compositions can be administered to a subject to stimulate antibody production against LPS or O-PS-Core from one or more of the aforementioned bacteria. In some instances, the conjugate compositions can be administered to a subject in need thereof to stimulate antibody production against *V. cholerae* (e.g., serotypes Inaba and/or Ogawa). In some instances, antibodies produced can be bactericidal against one or more of the organisms disclosed herein. Administration to the subject can be performed prior to exposure of the subject to the one or more organisms and/or following exposure. Accordingly, the conjugate compositions can be used to immunize or vaccinate a subject. Such treatment can result in a lessening or reduction of bacterial infection or symptoms associated there with, whether permanent or temporary, lasting or transient that can be attributed to or associated with treatment by the compositions and methods of the present invention.

For example, in some embodiments, the methods include administering a therapeutically effective amount of a conjugate vaccine as described herein in which the O-PS-core antigen of *Vibrio cholerae* O1 is directly conjugated to a carrier protein, e.g., bovine serum albumin (FIG. 1C) or Tetanus Toxin heavy chain (TThc) (FIG. 1D), to a subject in need thereof, e.g., a subject who has been, may be, or is likely to be exposed to *Vibrio cholerae*. In some embodiments, the subject is a subject, e.g., a human child or adult, who lives in or will be traveling to a region in which cholera is common or endemic.

Subject Selection

The present disclosure includes selecting a subject for treatment, e.g., a subject at risk for exposure to certain pathogens (e.g., bacterial or viral pathogens) and/or a subject that has been exposed to certain pathogens (e.g., bacterial or viral pathogens). Subject selection can include diagnosis and/or referral by a physician or other qualified medical profession and self-referral by the subject to be treated.

The term “subject” is used throughout the specification to describe an animal, human (e.g., including infants, children, and/or adults) or non-human, to whom treatment according to the methods of the present invention is provided. Veterinary and non-veterinary applications are contemplated.

Treatment

Treatment can include administration of an effective amount of one or more of the conjugate compositions disclosed herein. Compositions can be administered by any means that results in an increased antibody production in the subject and/or in any lessening of bacterial infection or symptoms associated there with, whether permanent or temporary, lasting or transient that can be attributed to or associated with treatment by the compositions and methods of the present invention. Compositions can be administered systemically and/or locally. For example, compositions can be administered orally, transcutaneously, and/or by injection or inoculation. A treatment results in induction of an immune response to the PS, and thus to the pathogen from which the pathogen is derived. Thus, for example, administering a conjugate molecule as described herein comprising a PS from *V. cholerae* will result in induction of an anti-cholera immune response.

EXAMPLES

The invention is further described in the following examples, which do not limit the scope of the invention described in the claims.

The following Examples describe the production of conjugate vaccines in which the O-PS-core antigen of *Vibrio cholerae* O1—the major cause of cholera, a severe dehydrating diarrheal disease of humans—is directly conjugated to a carrier protein, e.g., bovine serum albumin (FIG. 1C) or Tetanus Toxin heavy chain (TThc) (FIG. 1D) using the methods disclosed herein. These directly conjugated vaccines are shown to be recognized by convalescent phase sera from patients recovering from cholera in Bangladesh. Further, anti-O-PS-core-protein responses correlate with plasma anti-lipopolysaccharide and vibriocidal responses, which are the primary markers of protection from cholera. The conjugate vaccines disclosed herein have potential as vaccines for cholera and other bacterial diseases.

Example 1

Isolation of LPS of *Vibrio cholerae* O1 and Preparation of the O-PS-Core Antigens LPS was obtained from *V. cholerae* O1, Ogawa (strain X-25049) or Inaba (strain 19479), by hot phenol/water extraction followed by enzymatic treatment (DNase, RNase and protease), and ultracentrifugation (100,000×g for 3 hours). The pellet containing LPS was dialyzed against distilled water and freeze-dried. The LPS [10 mg/mL in 1% (v/v) aqueous acetic acid] was heated at 105° C. for 3 hours. Each hydrolysate was separated into chloroform-soluble and water-soluble fractions by thorough mixing with an equal volume of chloroform, followed by low-speed centrifugation. The water-soluble fraction containing the degraded polysaccharide moiety was separated, washed three or more times with chloroform, and then freeze-dried. The degraded polysaccharide was further fractionated by size exclusion chromatography (Sephacryl S-200) using water as eluent, giving two major peaks. The first peak corresponding to the O-PS-core was isolated and freeze-dried. The crude O-PS-core products were further purified by ultrafiltration using centrifugal filter devices (3K Amicon Ultra, Millipore) and dialyzed against 10 mM aqueous ammonium carbonate (centrifugation at 4° C., 14,000×g, 8 times, ~35 minutes each time) to remove the low molecular mass material. The retentate was lyophilized to afford the O-PS-core antigens as white solids.

Figure 1A:
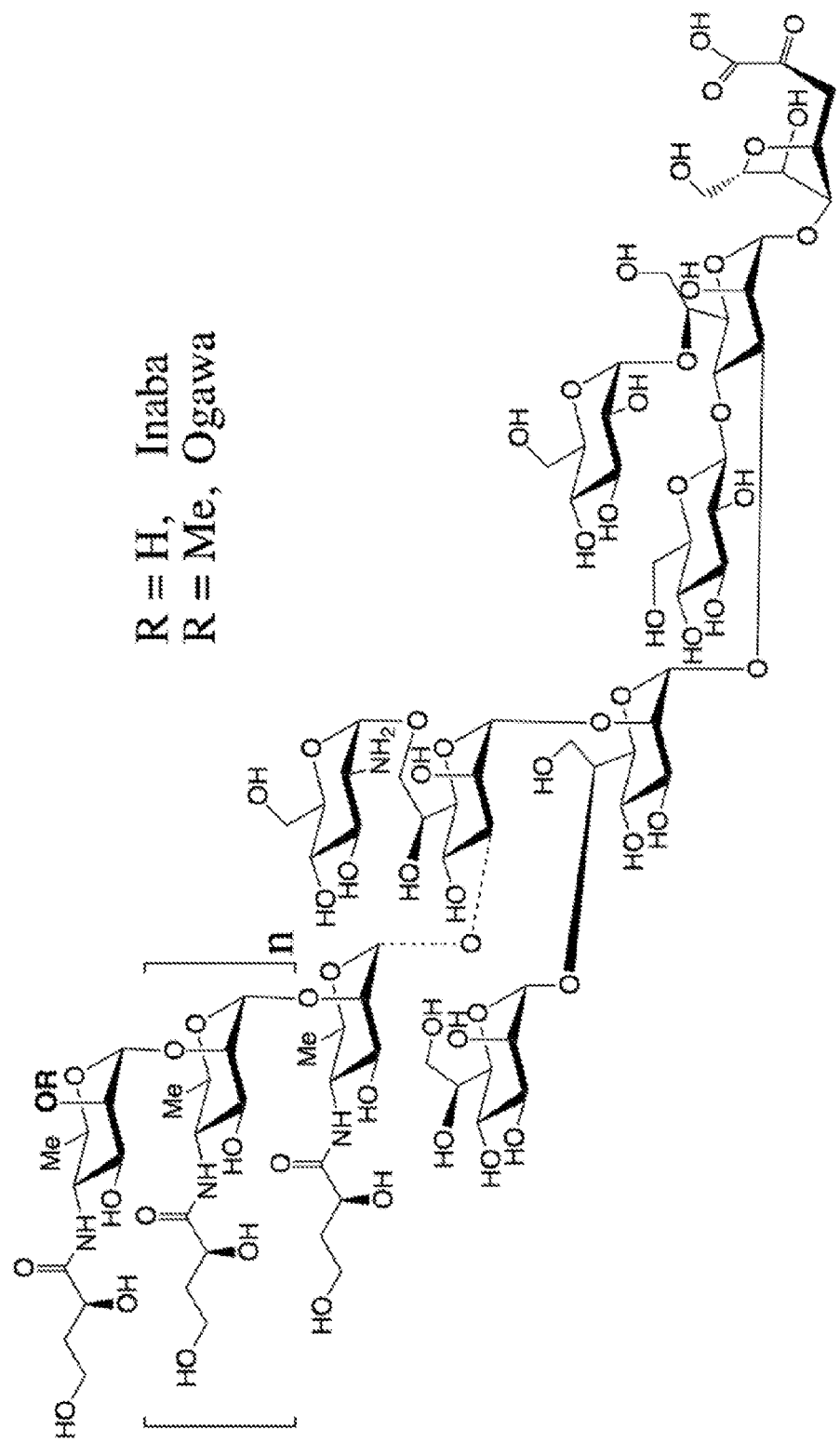
FIG. 1A shows a structure of bacterial O-PS-core antigen of *Vibrio cholerae* O1, serotype Inaba and Ogawa. The dotted bond indicates that the linkage of the O-PS to core has not been established.
Figure 1B:
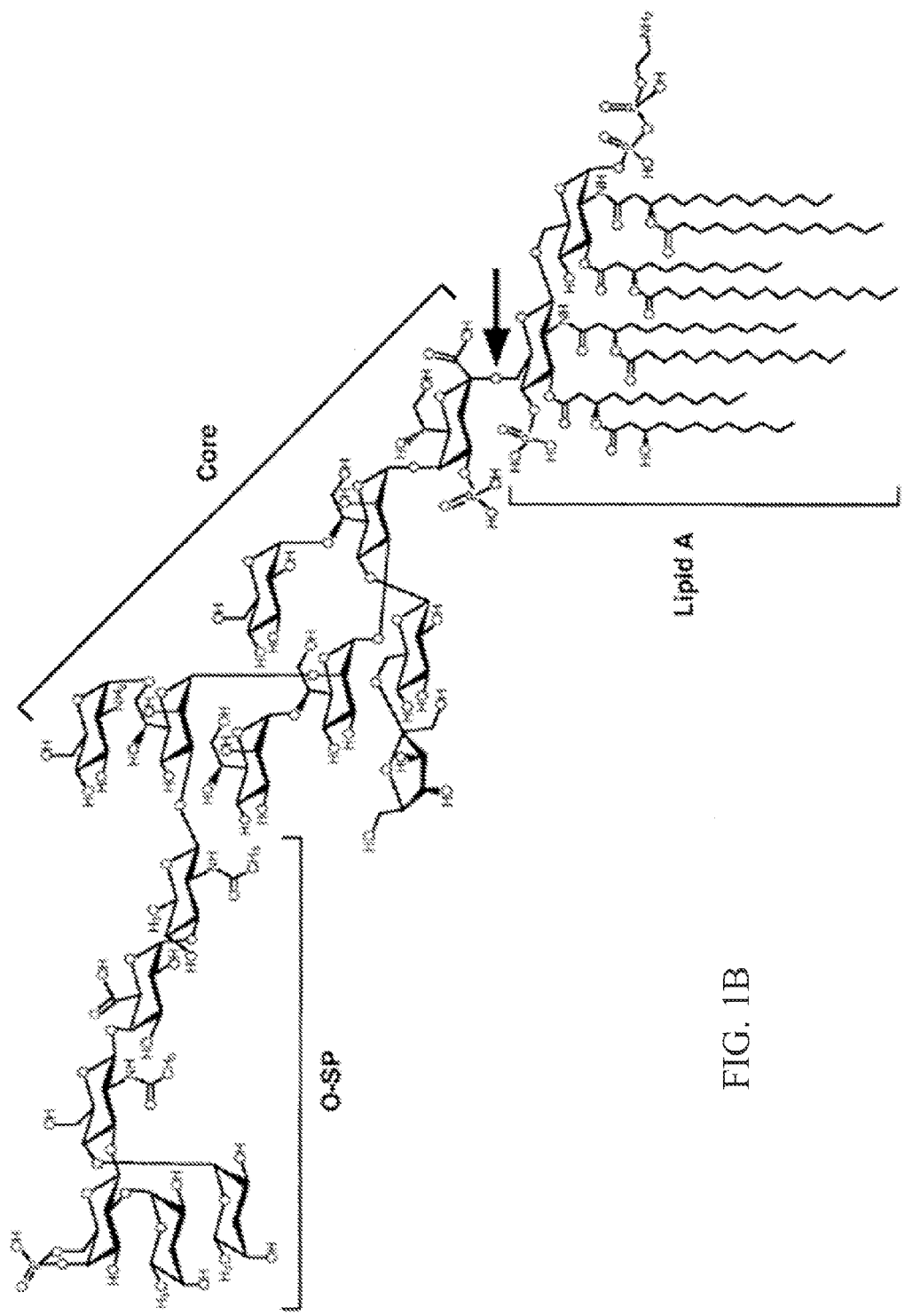
FIG. 1B shows a structure of a bacterial LPS, indicating the position at which acid hydrolysis releases the O-SP-core antigen.
Figure 1C:
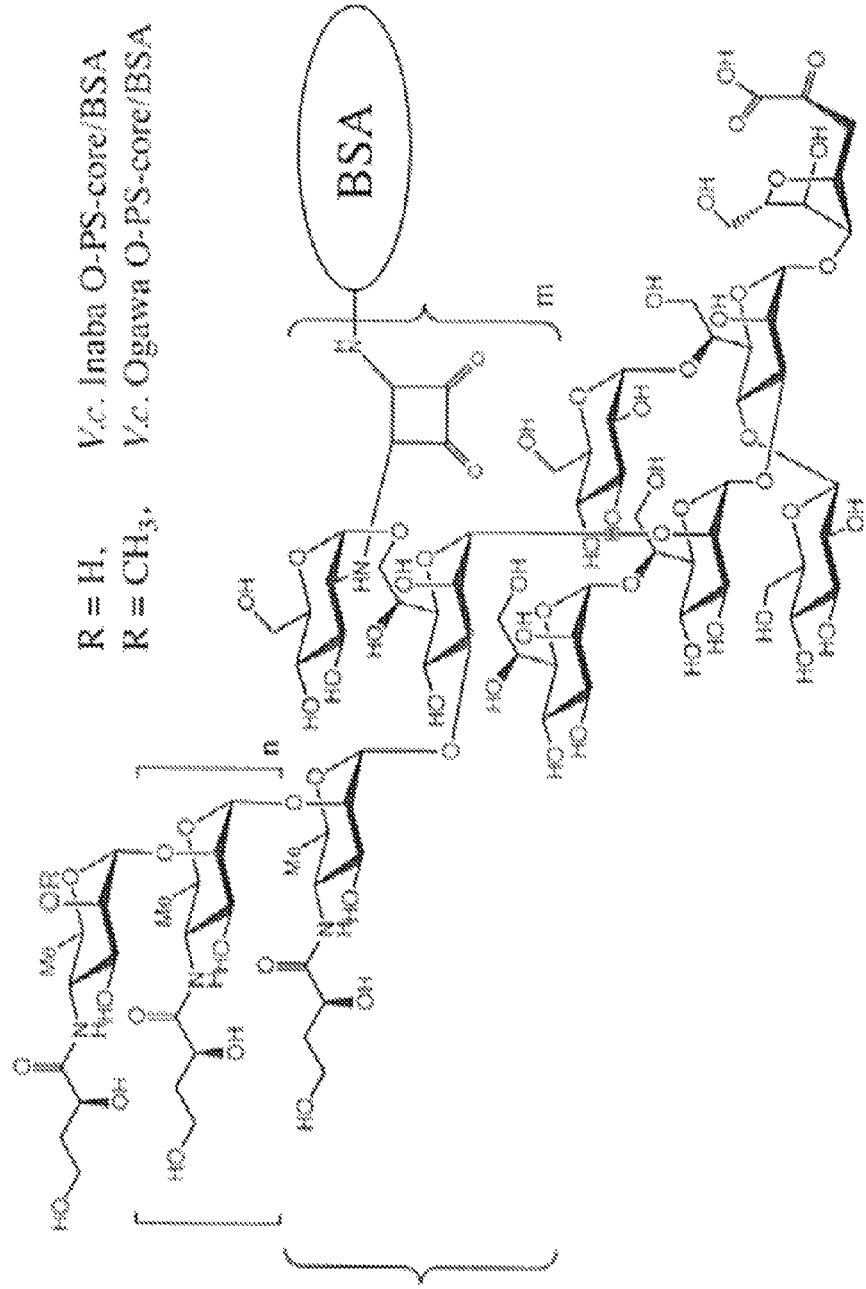
FIGS. 1C and 1D show structures of exemplary conjugate vaccines in which the O-PS-core antigen of *Vibrio cholerae* O1, serotype Ogawa, is directly conjugated to a carrier protein, e.g., bovine serum albumin (1C) or Tetanus Toxin heavy chain (TThc) (1D).
Figure 1D:
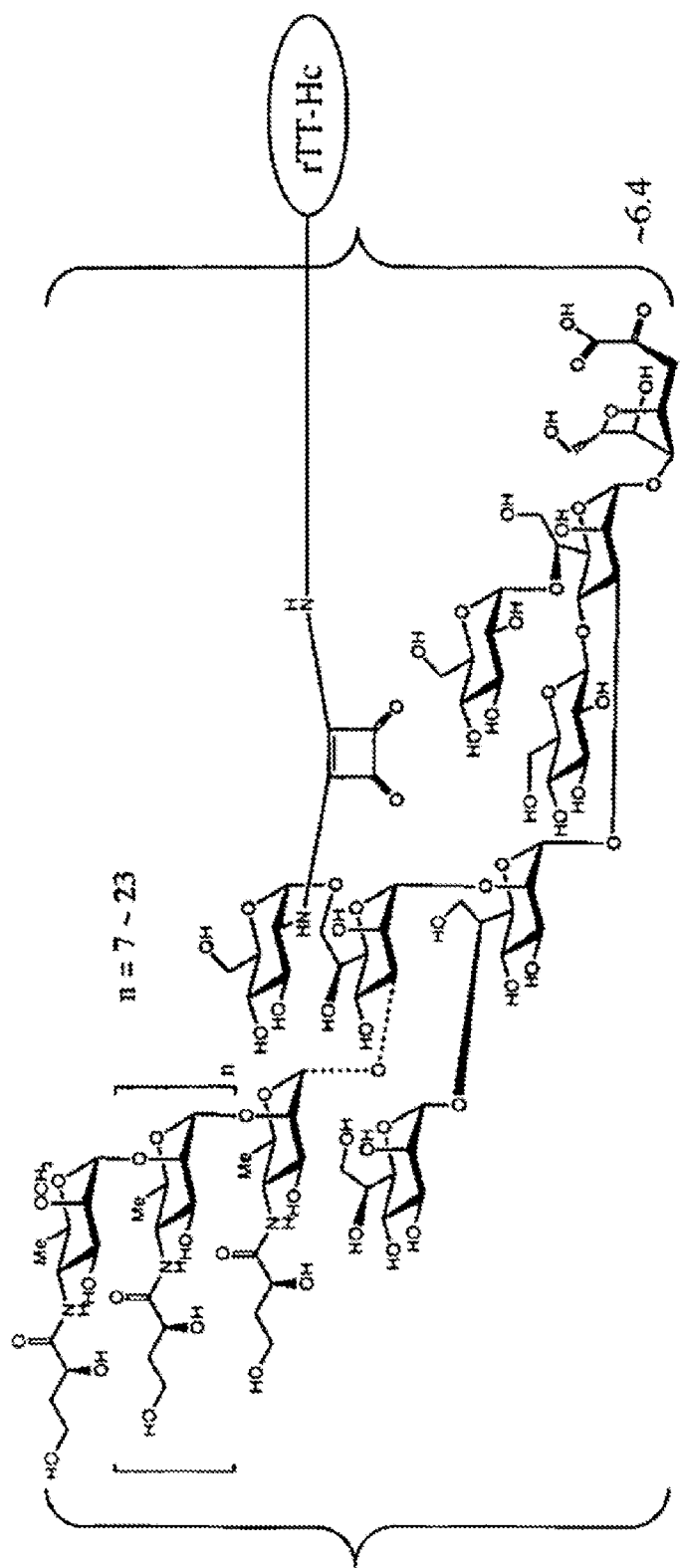

The structures of O-PSs of the two strains are very similar; they consist of a chain of (1→2)-α-linked moieties of 4-amino-4,6-dideoxy-α-D-mannopyranose (perosamine), the amino groups of which are acylated with 3-deoxy-L-glycero-tetronic acid. The O-PSs of the two strains differ in that the terminal, upstream perosamine moiety in the Ogawa strain carries a methoxy group at C-2 (FIG. 1A). $^{13}$C NMR spectra (150 MHz) of O-PS-core antigens were taken at ambient temperature for solutions in D$_2$O with a Bruker Avance 600 spectrometer equipped with a cryoprobe. Assignments of NMR signals could be confidently made by comparison with spectra of synthetic α-glycosides of hexasaccharide fragments of the respective O-PSs, since spectra of the O-PS-core and the hexasaccharides showed close similarity of chemical shifts of equivalent carbon atoms of the internal residues and of the terminal upstream residues.

Figure 2:
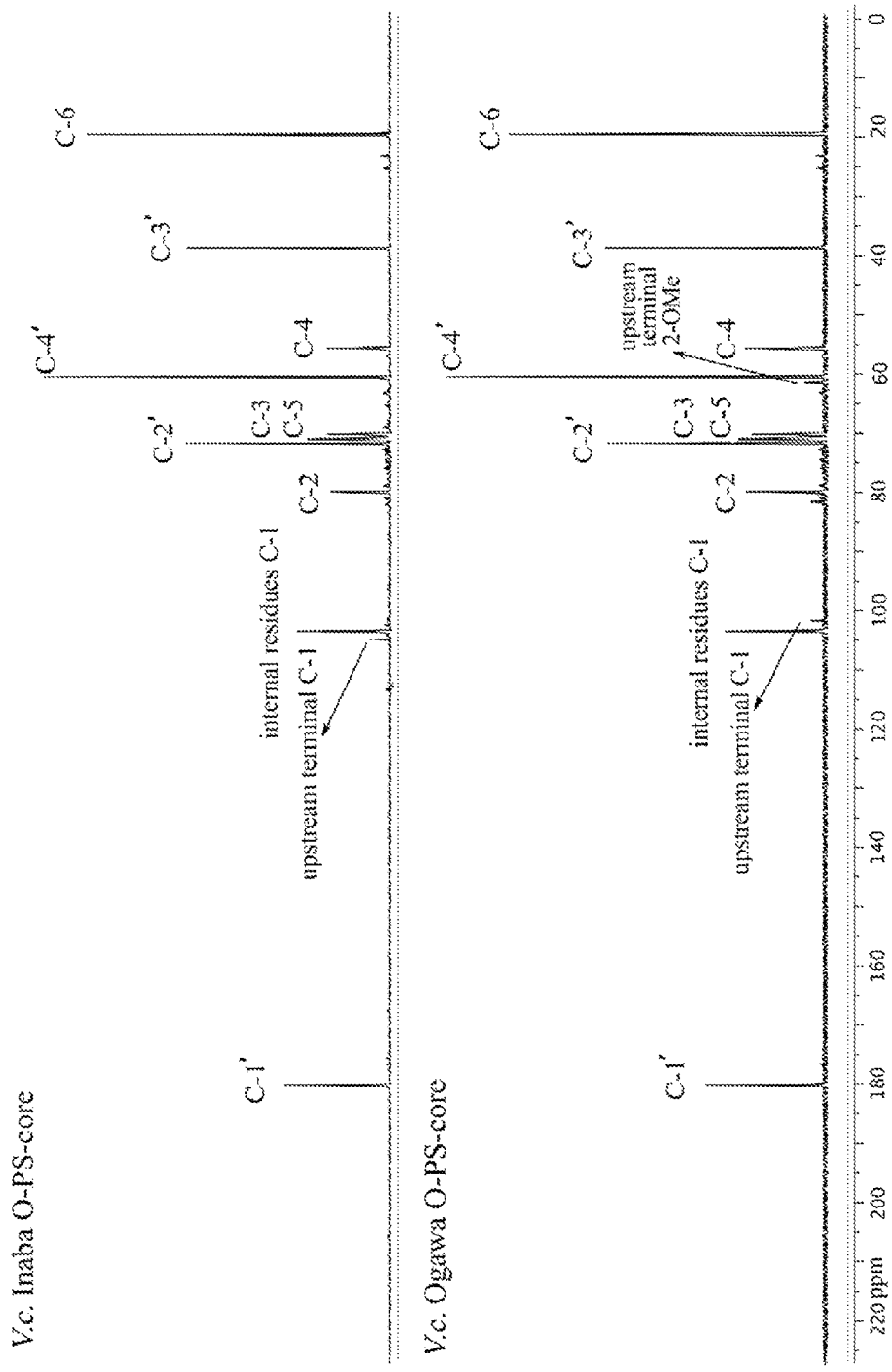
FIG. 2 shows $^{13}$C NMR spectra of the crude O-PS-core antigens of *V. cholerae*, serotype Inaba and Ogawa in $D_2O$.

The $^{13}$C NMR spectra (FIG. 2) of the antigens, where the signals of the O-PSs largely predominate, show all structurally significant peaks present in the spectra of the related, synthetic hexasaccharides.

Example 2

Preparation of Squarate Monoester Derivatives of the O-PS-Core Antigens

Vials equipped with Spin Vanes (Wheaton Science) were used as reaction vessels. Squaric acid dimethyl ester was purchased from Aldrich Chemical Company and recrystallized from methanol. 3,4-Dimethoxy-3-cyclobutene-1,2-dione (~0.5 mg) was added to a solution of O-PS-core antigen (0.80 mg and 0.92 mg for Inaba and Ogawa, respectively) in 7 phosphate buffer (0.05 M, 50 µL) contained in a 1 mL V-shaped reaction vessel, and the mixture was gently stirred at room temperature for 48 hours. The resulting solution was transferred into an Amicon Ultra (0.5 mL, 3K cutoff) centrifuge tube and dialyzed against pure water (centrifugation at 4° C., 14,000×g, 8 times, ~35 minutes each time). The retentate was lyophilized to afford the O-PS-core squarate monomethyl ester as white solid [0.75 mg (94%) and 0.86 mg (93%)] for Inaba and Ogawa, respectively.

Figure 3:
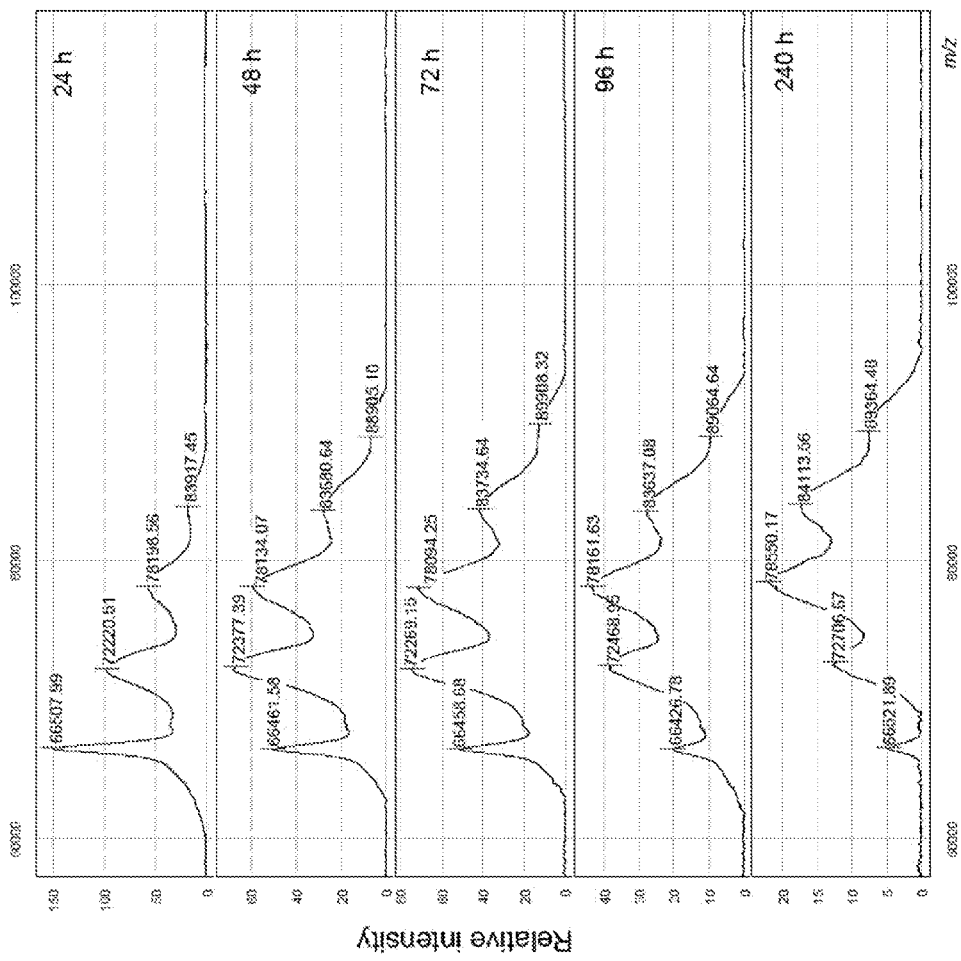
FIG. 3 shows monitoring of the conjugation of Inaba O-PS-core antigens to BSA.
Figure 4:
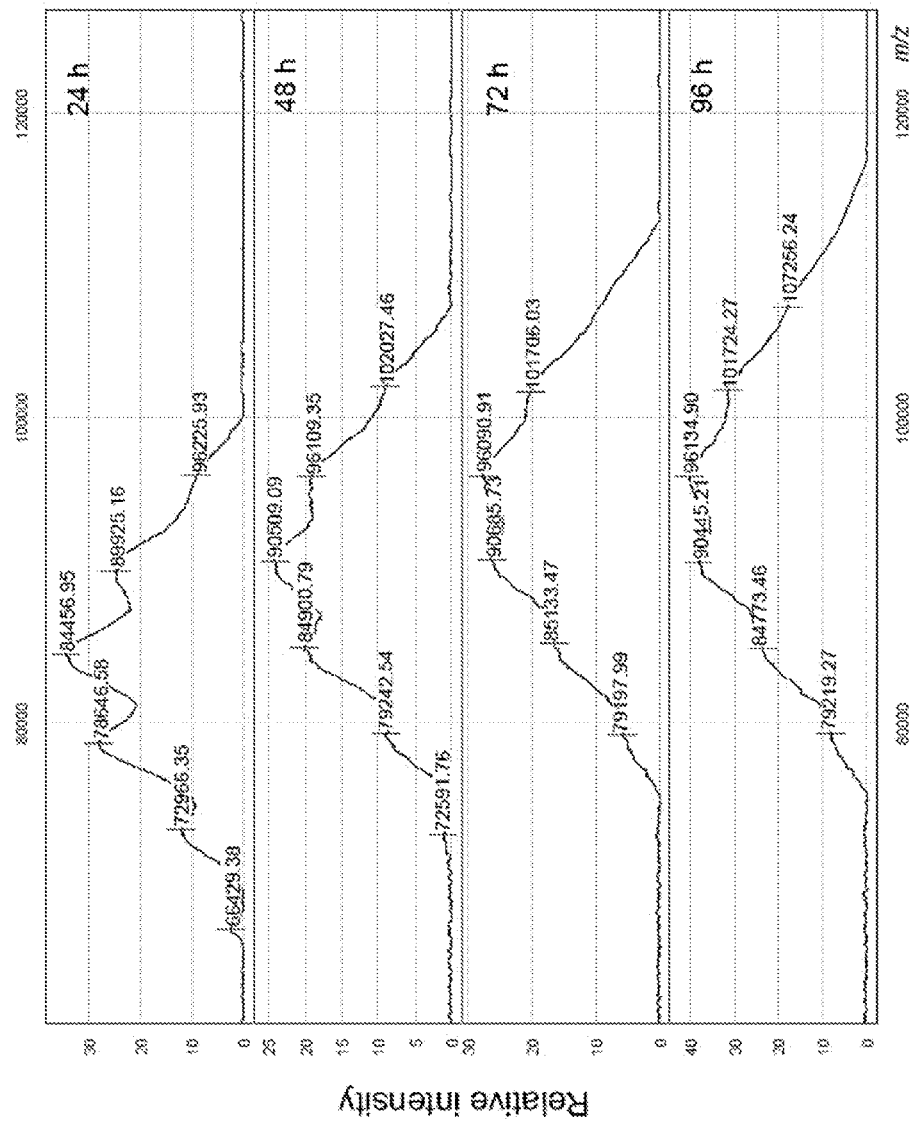
FIG. 4 shows monitoring of the conjugation of Ogawa O-PS-core antigens to BSA.

Successful formation of the corresponding monomethyl ester manifested itself when the material was treated with BSA at pH 9 resulting in smooth conjugate formation (FIGS. 3 and 4).

Example 3

Conjugation of the Inaba O-PS-Core Antigens to BSA

Conjugation of carbohydrates was monitored by the Bio-Rad Protein Chip SELDI system using NP-20 chip arrays. 3,5-Dimethoxy-4-hydroxycinnamic acid (sinapinic acid) was used as matrix. Knowing that the reaction rate of conjugation decreases with the size of oligosaccharides, and considering the actual reaction rates for a disaccharide, tetrasaccharide and a hexasaccharide (see, Hou, S.-j., Saksena, R., and Kováč, P., 2008. Preparation of glycoconjugates by dialkyl squarate chemistry revisited. Carbohydr. Res., 343, 196-210), the conjugation was carried out at an initial Inaba O-PS-core/BSA ratio of 1/1.2 (w/w), which corresponded to an approximate molar Inaba O-PS-core/

BSA ratio of 10.8/1. Bovine serum albumin (BSA) was purchased from Sigma (Cat. No. A-4503), and used as supplied.

BSA (0.9 mg) and Inaba O-PS-core antigen (0.75 mg) were weighed into a 1 mL V shape reaction vessel and 60 µL of 0.5 M pH 9 borate buffer was added (to form ~2.5 mM solution with respect to the antigen; antigen:carrier=10.8:1). A clear solution was formed. The mixture was stirred at room temperature and the reaction was monitored by SELDI-TOF MS at 24, 48, 72, 96, and 240 hours (FIG. 3), when the reaction was terminated by addition of 300 µL of 7 phosphate buffer. The solution was transferred into an Amicon Ultra (0.5 mL, 30 K cutoff) centrifuge tube and dialyzed (centrifugation at 4° C., 10,000×g, 8 times, 12 minutes) against 10 mM aqueous ammonium carbonate. After lyophilization, 0.80 mg (73%, based on BSA) of conjugate was obtained as a white solid. Based on the average MW of the hapten, the ratio of hapten:BSA was 2.8:1 (conjugation efficiency, 26%).

The conjugation was performed at an O-PS-core concentration of ~2.5 mM. When the conjugation process was terminated after 10 day, SELDI analysis of the purified conjugate after freeze drying showed that the average molecular mass of the conjugate obtained was 81,000 Da (molar ratio O-PS-core:BSA=~2.8). The conjugate still contained some (~5%) of the unchanged BSA (shown also in FIG. 3, 240 hours).

Example 4

Conjugation of the Ogawa O-PS-Core Antigens to BSA

To ensure that no BSA used at the onset of the conjugation would be left unconjugate, the reaction of the Ogawa O-PS-core antigen was set up at a higher initial O-PS-core:BSA ratio [~2:1 (w/w), which corresponded to an approximate initial molar Ogawa O-PS-core/BSA ratio of 21.5:1]. The protocol described above was followed with 0.86 mg of Ogawa antigen, 0.45 mg of BSA (antigen:carrier=21.5:1) and 30 µL of pH 9 borate buffer (~4.9 mM solution with respect to hapten).

Monitoring of the progress of the conjugation is shown in FIG. 4. As shown in FIG. 4, only a negligible amount of unchanged BSA was present in the conjugation mixture after 24 hours of the reaction time. After 96 hours, when the conjugation was terminated, the conjugate was isolated, and MS analysis by SELDI showed the average molecular mass of the conjugate obtained to be ~95,000 Da (molar ratio O-PS-core:BSA=~4.8). After freeze-drying, 0.54 mg (84%, based on BSA) of conjugate was obtained as a white solid. Based on the average MW of the hapten, the ratio of hapten:BSA was 4.8:1 (conjugation efficiency, 23%).

Example 5

Assessing LPS, O-PS-Core-BSA and BSA-Specific Antibody Responses in Plasma of Patients with Cholera, as Well as Vibriocidal Responses To assess the immunoreactivity of the conjugates and their potential use as cholera vaccines, anti-O-PS-core-BSA antibody levels in the blood of patients with cholera in Bangladesh, were measured and compared to anti-LPS and vibriocidal responses, the latter two being primary predictors of protection against cholera (Ramamurthy et al., Lancet 31:703-4, 1993; Mosley et al., Bull. World Health Organ. 38:777-785, 1968; Glass et al., J Infect Dis 151:236-242, 2008; and Harris et al., PLoS Negl. Trop. Dis. 2, e221, 2008).

Acute and convalescent phase blood was obtained through fully IRB-approved protocols from twenty individuals with *V. cholerae* O1 stool-culture-confirmed cholera (Ogawa=10; Inaba=10) admitted to the hospital of the International Centre for Diarrhoeal Diseases Research, in Dhaka Bangladesh (ICDDR, B). For this study, blood samples obtained on days 2 and 7 after onset of illness, were used for antigen-specific and vibriocidal assays. The vibriocidal antibody titer and antigen-specific IgG antibody responses were measured using the homologous serotype of *V. cholerae* O1 LPS, or O-PS-core-BSA, Ogawa or Inaba.

Anti-LPS, O-PS-core-BSA and BSA IgG responses in plasma were quantified using standard enzyme-linked immunosorbent assay (ELISA) protocols. To assess anti-LPS IgG responses, ELISA plates were coated with the homologous serotype of *V. cholerae* O1 LPS (2.5 µg/mL) in PBS. To assess anti-O-PS-core-BSA or anti-BSA IgG responses, ELISA plates were coated with O-PS-core/BSA (1 µg/mL) or BSA (5 µg/mL) in carbonate buffer pH 9.6, respectively. 100 µL/well of plasma (diluted 1:50 in 0.1% BSA in phosphate-buffered saline—Tween) was added to each well, and the presence of antigen-specific antibodies was detected using horseradish peroxidase-conjugate anti-human IgG antibody. After 1.5 hour incubation at 37° C., the plates were developed with a 0.55 mg/mL solution of 2,2'-azino-bis(3-ethylbenzthiazoline-6-sulphonic acid (ABTS; Sigma) with 0.03% $H_2O_2$ (Sigma), and the optical density at 405 nm with a Vmax microplate kinetic reader (Molecular Devices Corp., Sunnyvale, Calif.), was determined. Plates were read for 5 min at 14 s intervals, and the maximum slope for an optical density change of 0.2 U was reported as millioptical density units per minute (mOD/min). ELISA units were normalized by calculating the ratio of the optical density of the test sample to that of a standard of pooled convalescent-phase plasma from patients recovered from cholera. Vibriocidal responses were assessed as previously described, using guinea pig complement and the homologous serotype of *V. cholerae* O1 Ogawa (X-25049) or Inaba (19479) as the target organism (Qadri et al., Infect Immun 65:3571-6, 1997). The vibriocidal titer was defined as the reciprocal of the highest serum dilution resulting in greater than 50% reduction of the optical density associated with *V. cholerae* growth compared to that of the positive control wells without plasma (Qadri et al., Clin Diagn Lab Immunol 2:685-88, 1995). The magnitude of acute was compared to convalescent phase responses, and significance was tested using Wilcoxon Signed Rank test, and used linear regression for correlation analysis between vibriocidal antibody and antigen-specific antibody responses. All reported P values were two-tailed, with a cutoff of $P<0.05$ considered a threshold for statistical significance.

Figure 5:
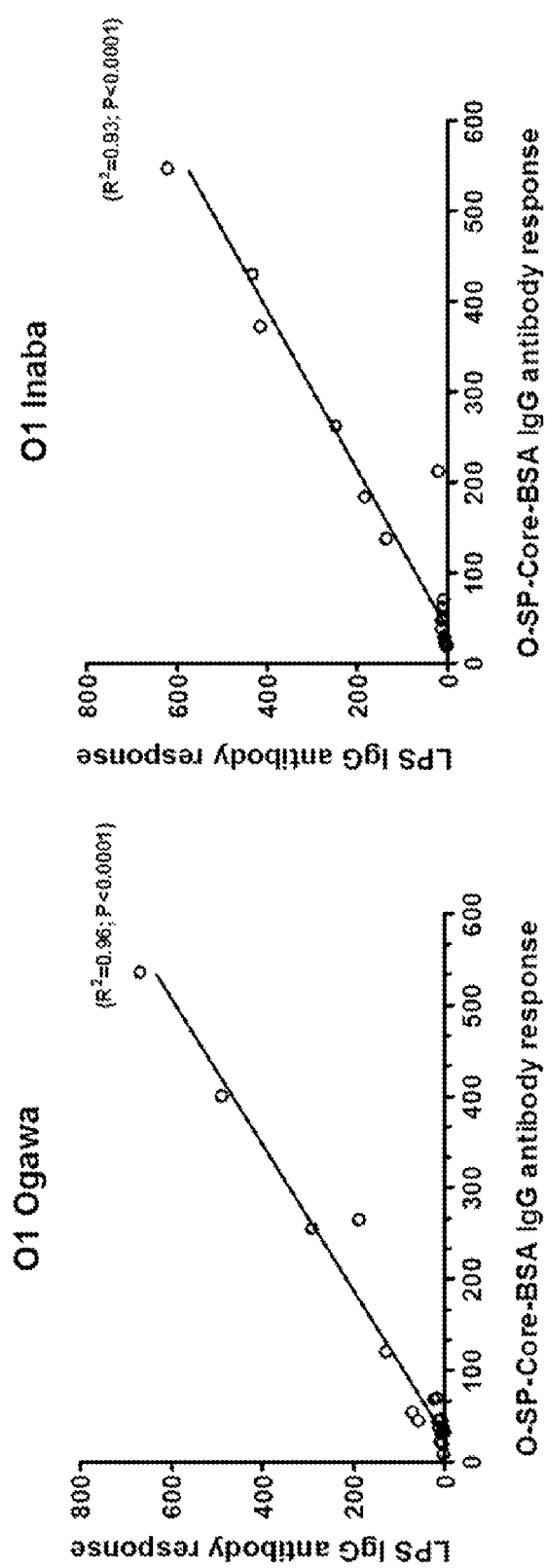
FIG. 5 shows correlation between anti-*V. cholerae* O1 LPS IgG antibody responses and corresponding O-SP-core-BSA IgG antibody responses. Lines designate linear correlations between the responses.

There was excellent correlation of the immunoreactivity of the O-PS-core-BSA conjugates and the homologous anti-LPS responses in convalescent phase blood of humans recovering from cholera in Bangladesh (Ogawa, $R^2=0.96$, $P<0.001$; Inaba, $R^2=0.93$, $P<0.001$; FIG. 5).

Figure 6:
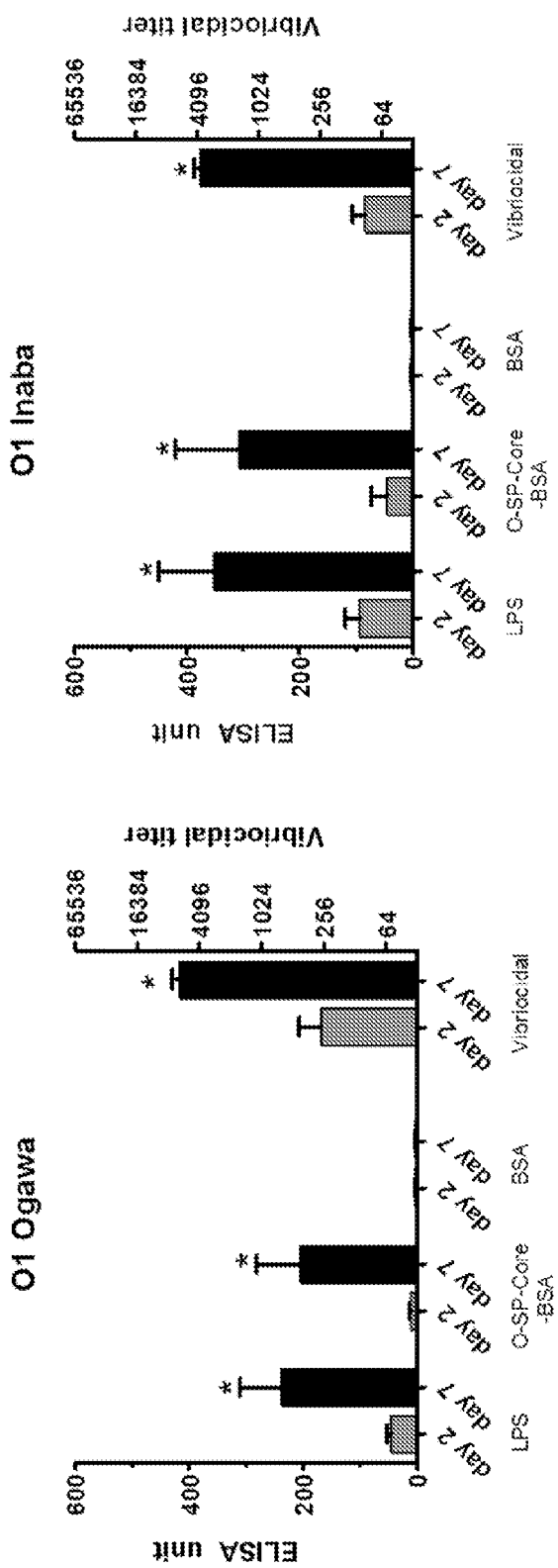
FIG. 6 shows normalized mean of antigen-specific IgG and vibriocidal antibody responses in plasma (with standard errors of the means [SEM]). Plasma IgG and vibriocidal responses are shown on the left and right (log 2) axes, respectively. An asterisk denotes a statistically significant difference (P<0.05) from the baseline (day 2) titer.

There was also significant and antigen-specific increases in anti-O-PS-core-BSA responses in convalescent compared to acute phase blood for both the Ogawa and Inaba constructs ($P<0.05$; FIG. 6).

Figure 7:
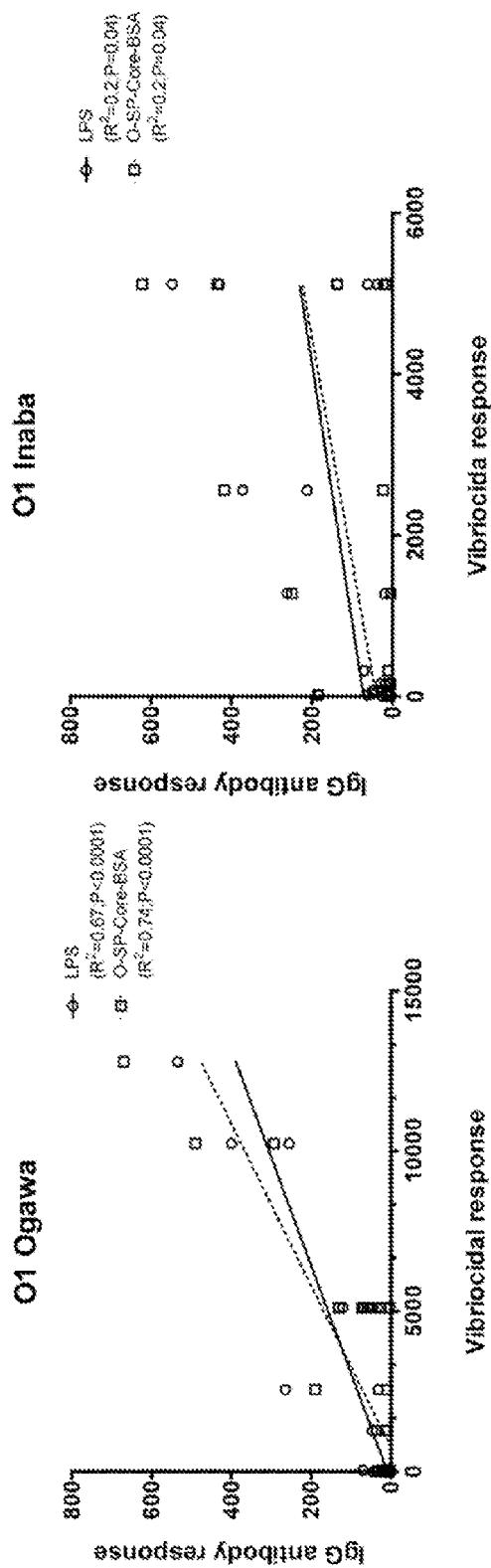
FIG. 7 shows correlation between vibriocidal antibody responses and the corresponding LPS or O-SP-core-BSA IgG antibody responses. Lines designate linear correlations between the responses.
Figure 8:
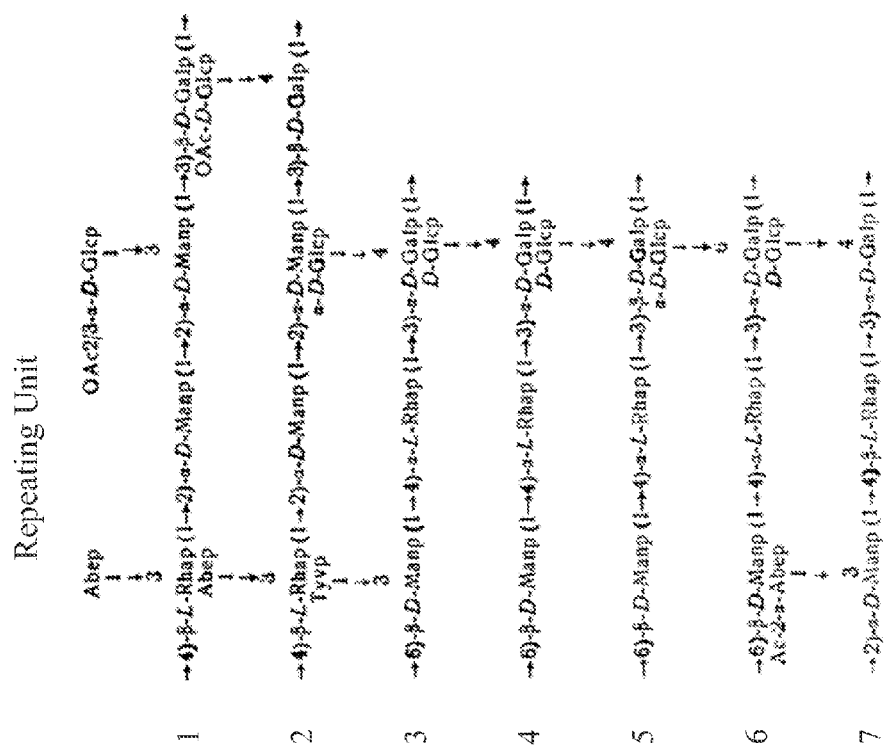
FIG. 8 shows structures of the O-Specific Polysaccharides of *Salmonella* sp. 1=*S. newport*; 2=*S. kentucky*; 3=*S. strasbourg*; 4=*S. muenster*; 5=*S. newington*; 6=*S. seftenberg*; 7=*S. typhimurium*; Abe=3,6-dideoxy-D-xylohexose (abequose); Tyv=3,6-dideoxy-D-arabinohexose (tyvelose); p=pyranose.
Figure 9:
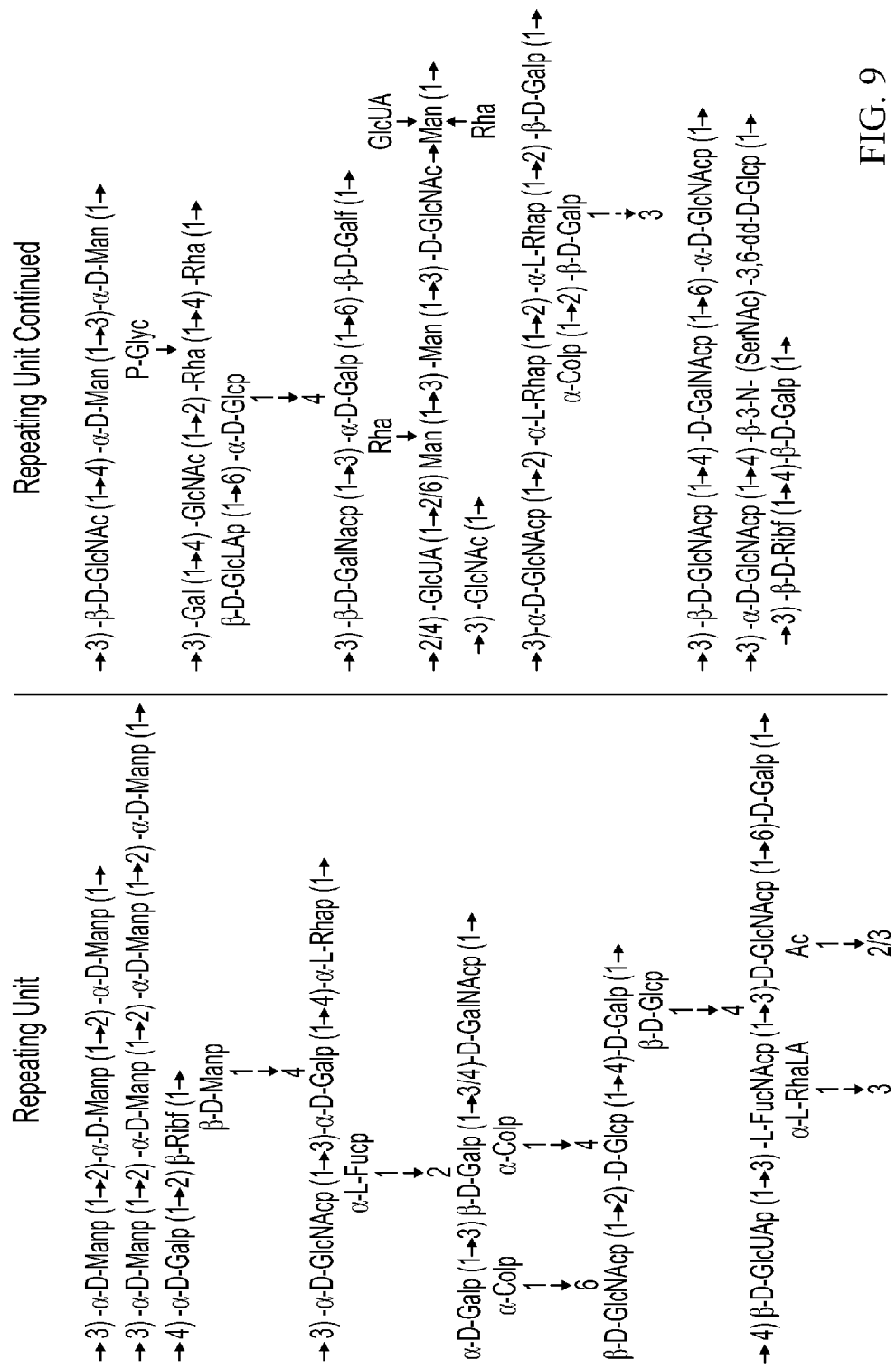
FIG. 9 shows structures of the O-Specific Polysaccharides of *Eschericia coli*. Col=colitose (3,6-dideoxy-L-xylohexose); Rib=ribose; D-GalNAc=N-acetyl-D-galactosamine; D-GlcNAc=N-acetyl-D-glucosamine; L-FucNAc=N-acetyl-L-fucosamine; P-Glyc=glyceryl phosphate; D-Glc-UA=glucuronic acid; D-GlcLA=glucolactylic acid (4-O—(R)-1'-carboxyethyl-D-glucose); 3-N-(SerNAc)-3,6-dd-D-Glc=3[(N-acetylseryl)amino]-3,6-diceoxy-D-g-glucose; f=furanose.
Figure 10:
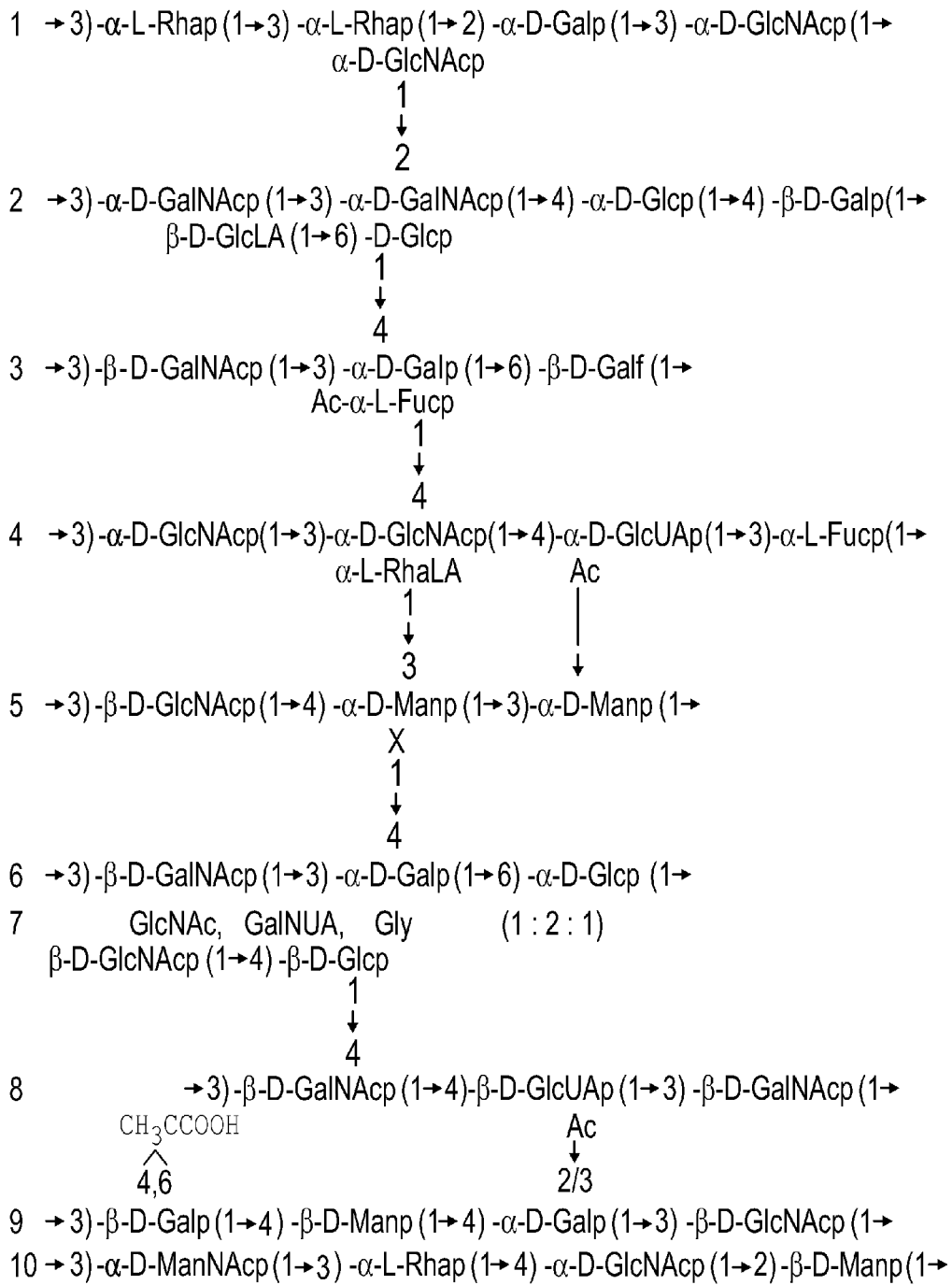
FIG. 10 shows structures of the O-Specific Polysaccharides of *Shigella dysenteriae*. L-RhaLA=rhamnolactylic acid (3-O—[(R)-1'-carboxyethyl]-L-rhamnose).
Figure 11:
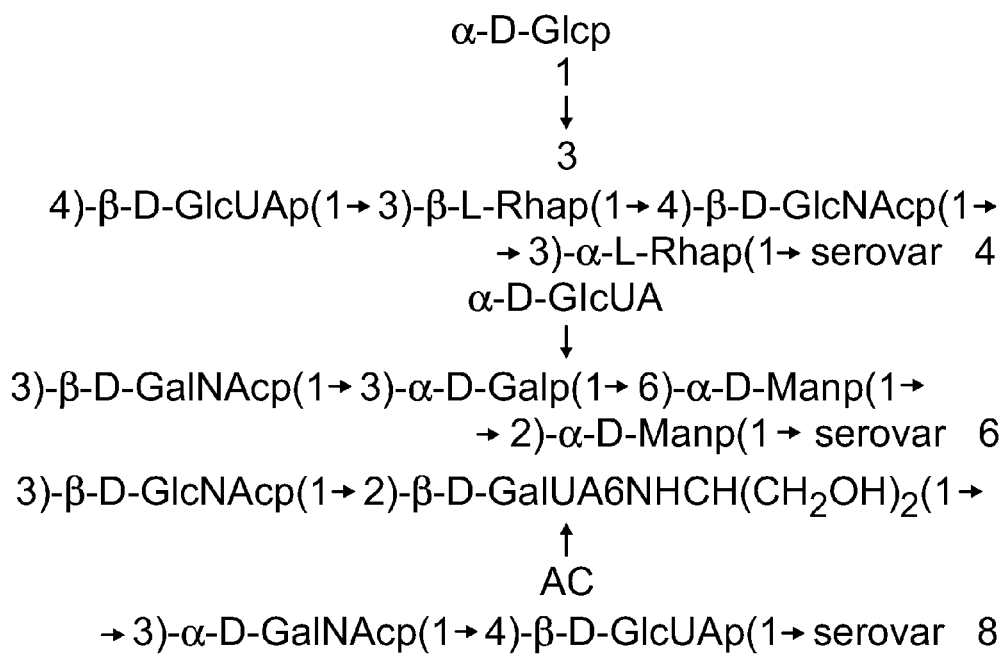
FIG. 11 shows structures of the O-Specific Polysaccharides of *Shigella boydii*.
Figure 13:
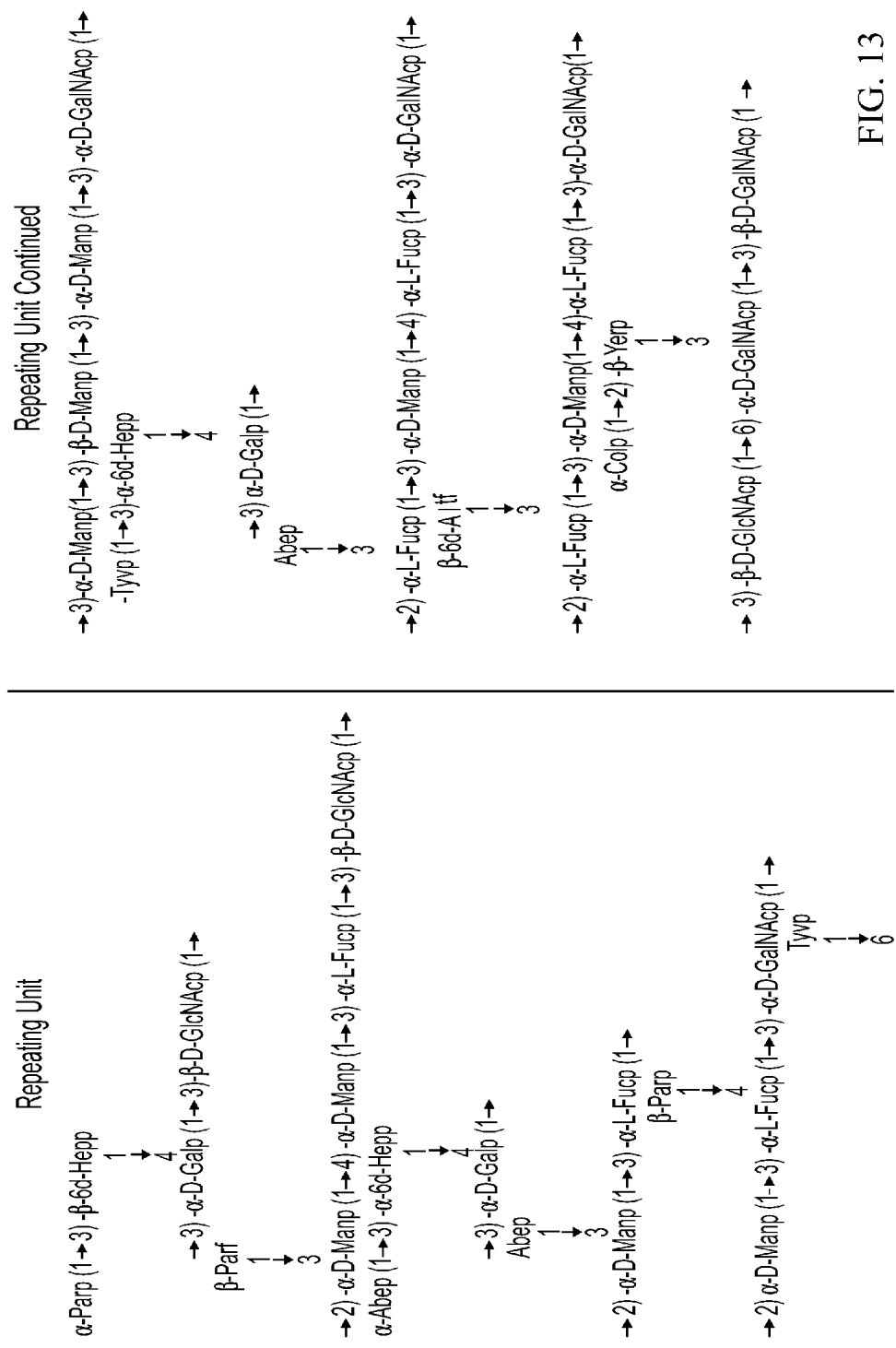
FIG. 13 shows structures of the O-Specific Polysaccharides of *Yersinia pseudotuberculosis*. Yer=yersiniose (3,6-dideoxy-4-C-(hydroxyethyl)-D-xylohexose); Par=paratose; 6d-Hep=6-deoxyheptose; 6d-Alt=6-deoxyaltrose.
Figure 15:
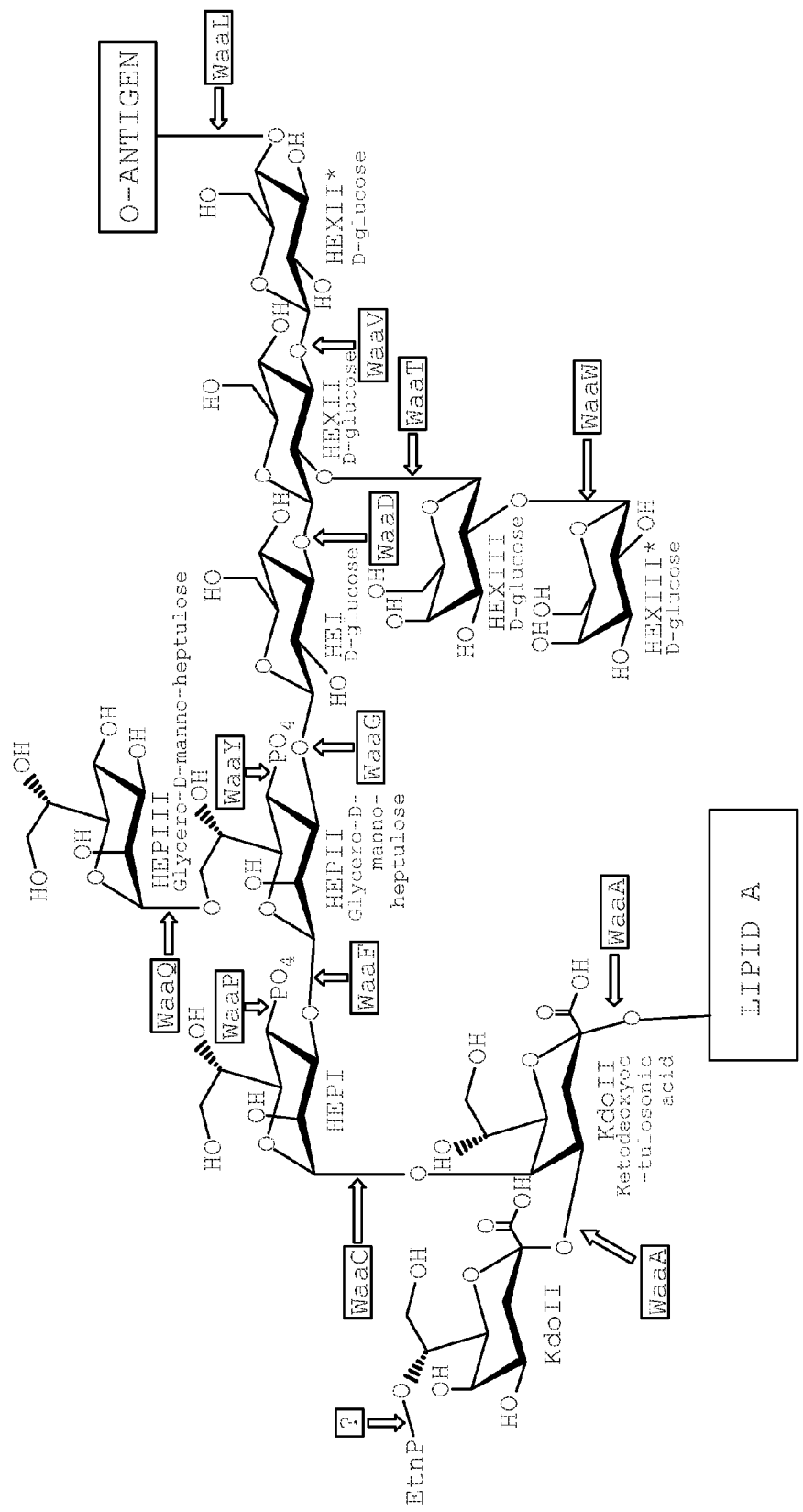
FIG. 15 shows structures of the core oligosaccharide of *E. coli*.
Figure 16:
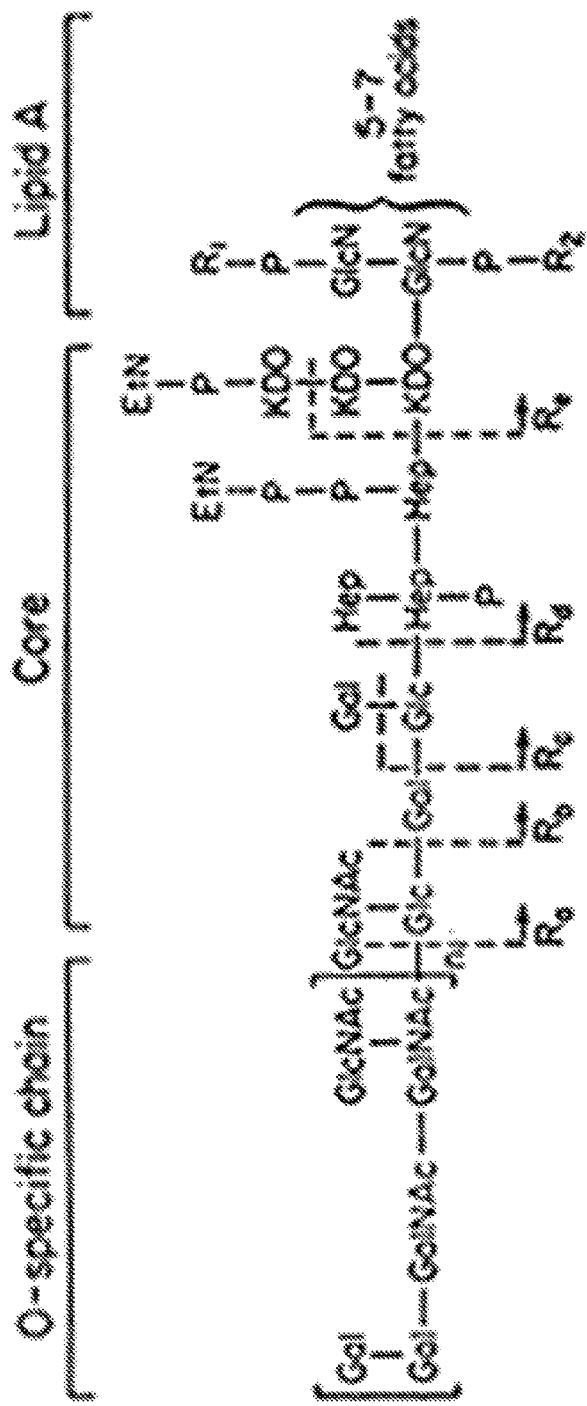
FIG. 16 shows a general structure of *Salmonella* LPS. Glc=glucose; GlcNac=N-acetyl-glucosamine; Gal=galactose; Hep=heptose; P=phosphate; Etn=ethanolamine; R1, and R2=phoshoethanolamine or aminoarabinose. Ra to Re indicate incomplete forms of LPS.
Figure 17:
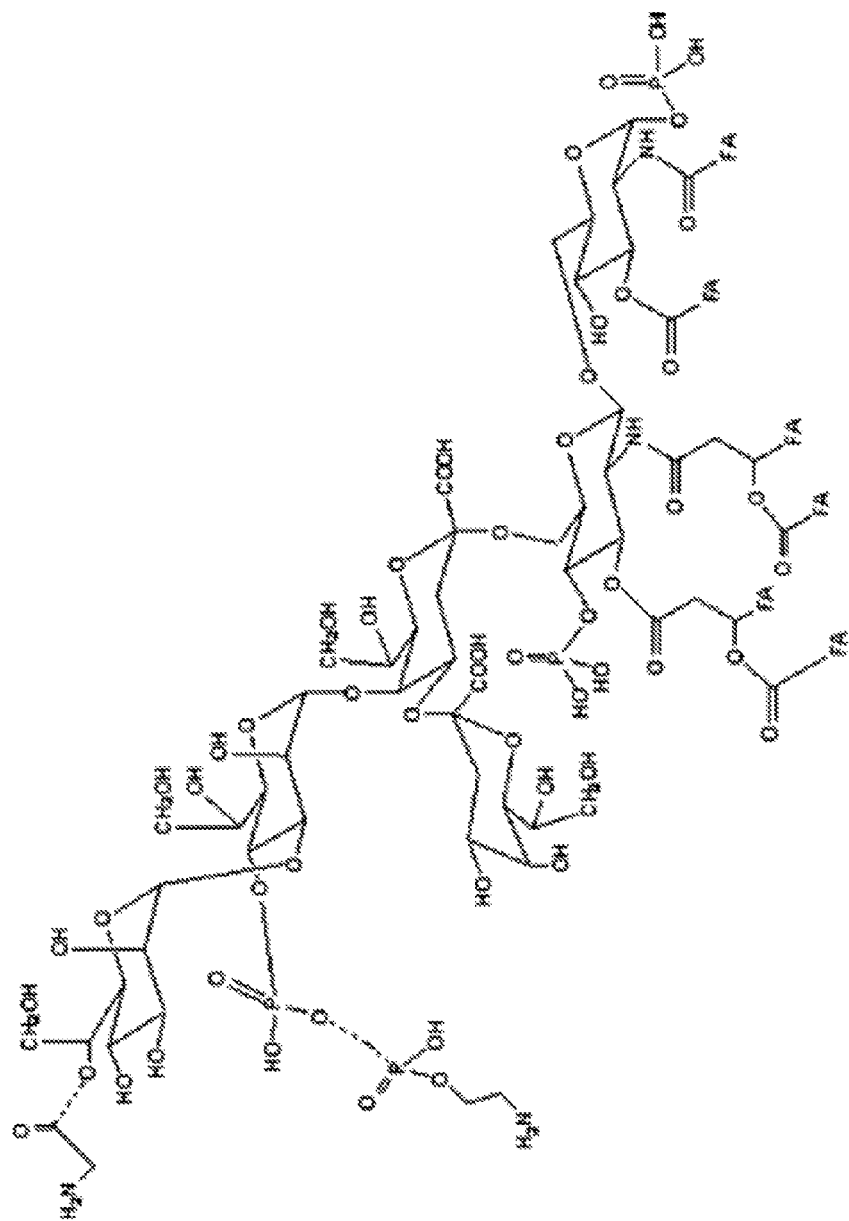
FIG. 17 shows a structure of LPS of a *Salmonella flexneri* M90T serotype 5 ΔgalU mutant.
Figure 18A:
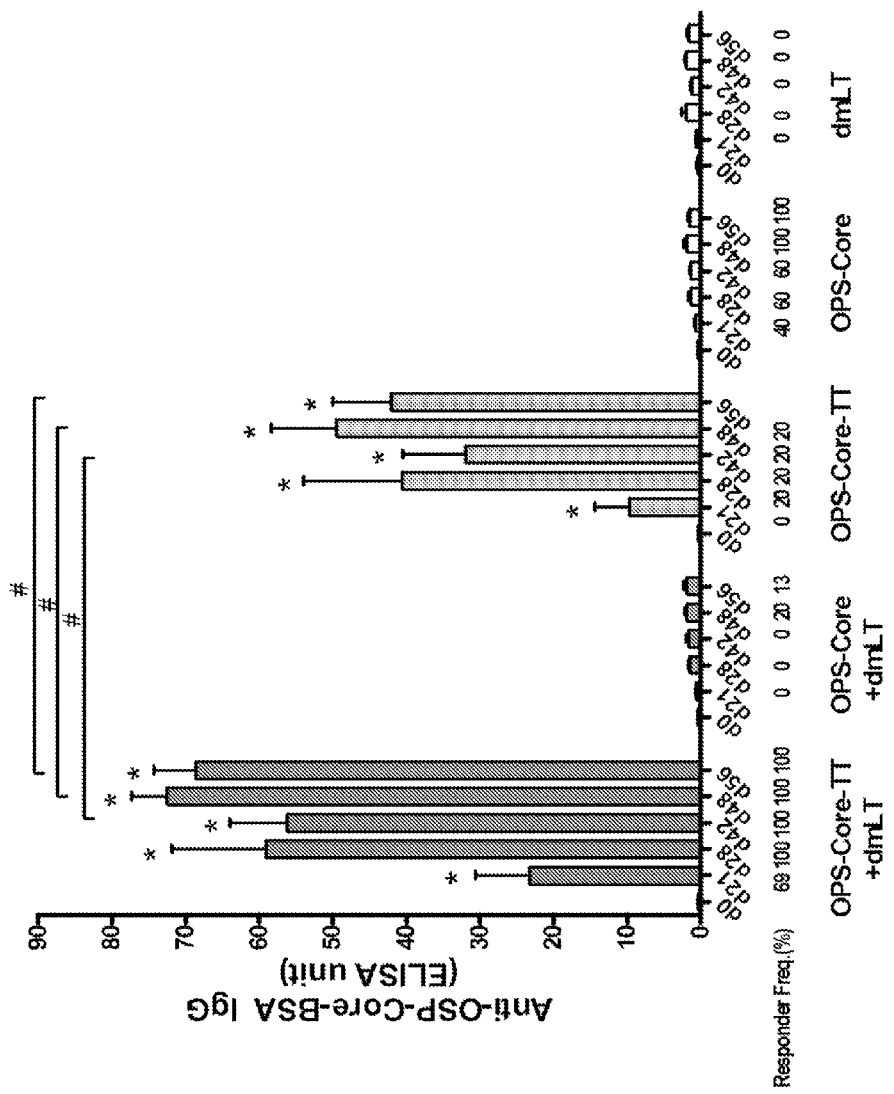
FIGS. 18A-D are each bar graphs showing serum anti-OSP-BSA and anti-LPS antibody responses in mice immunized intramuscularly (mean±SEM). An asterisk denotes a statistically significant difference (P<0.05) from the baseline (day 0) titer. Responder frequencies are also listed. #, statistically significant difference among the vaccine cohorts (P<0.05).
Figure 18B:
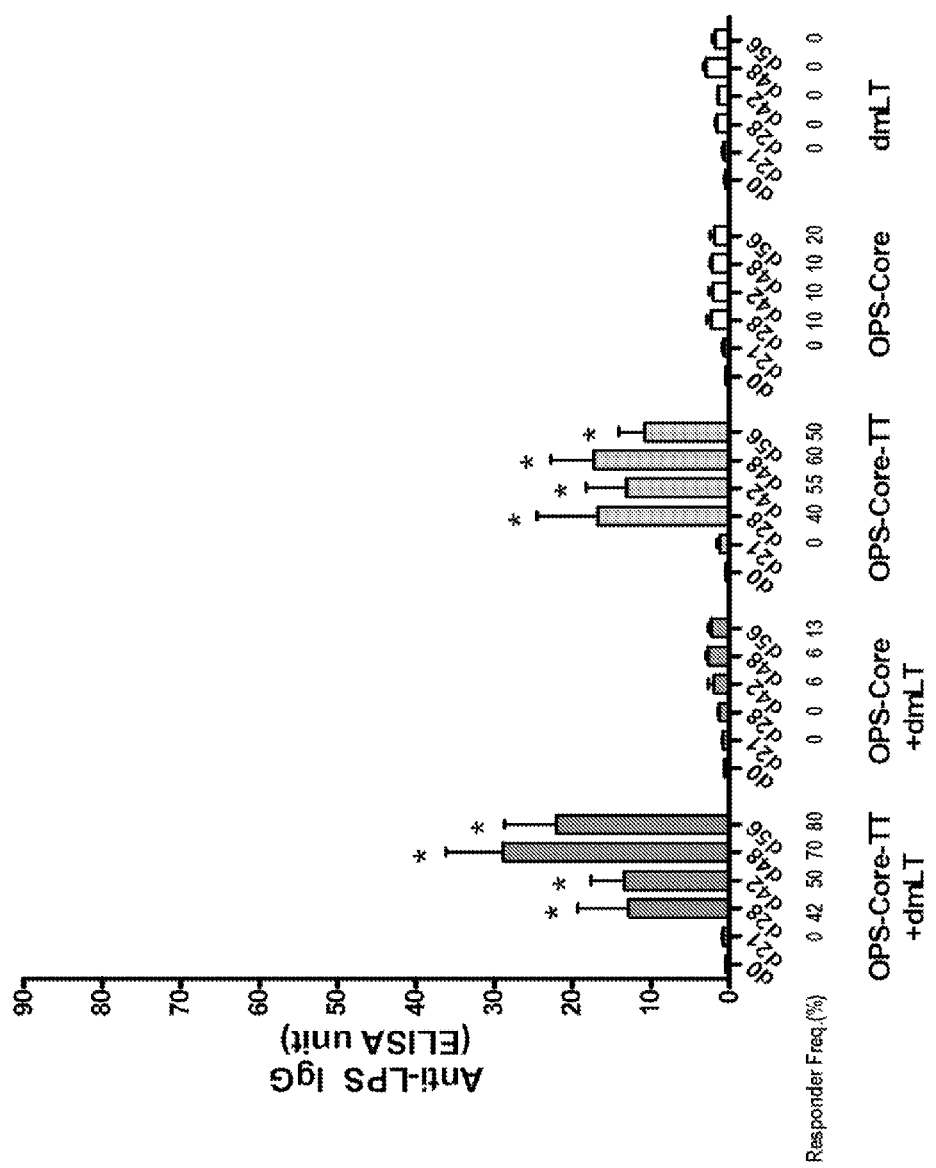
Figure 18C:
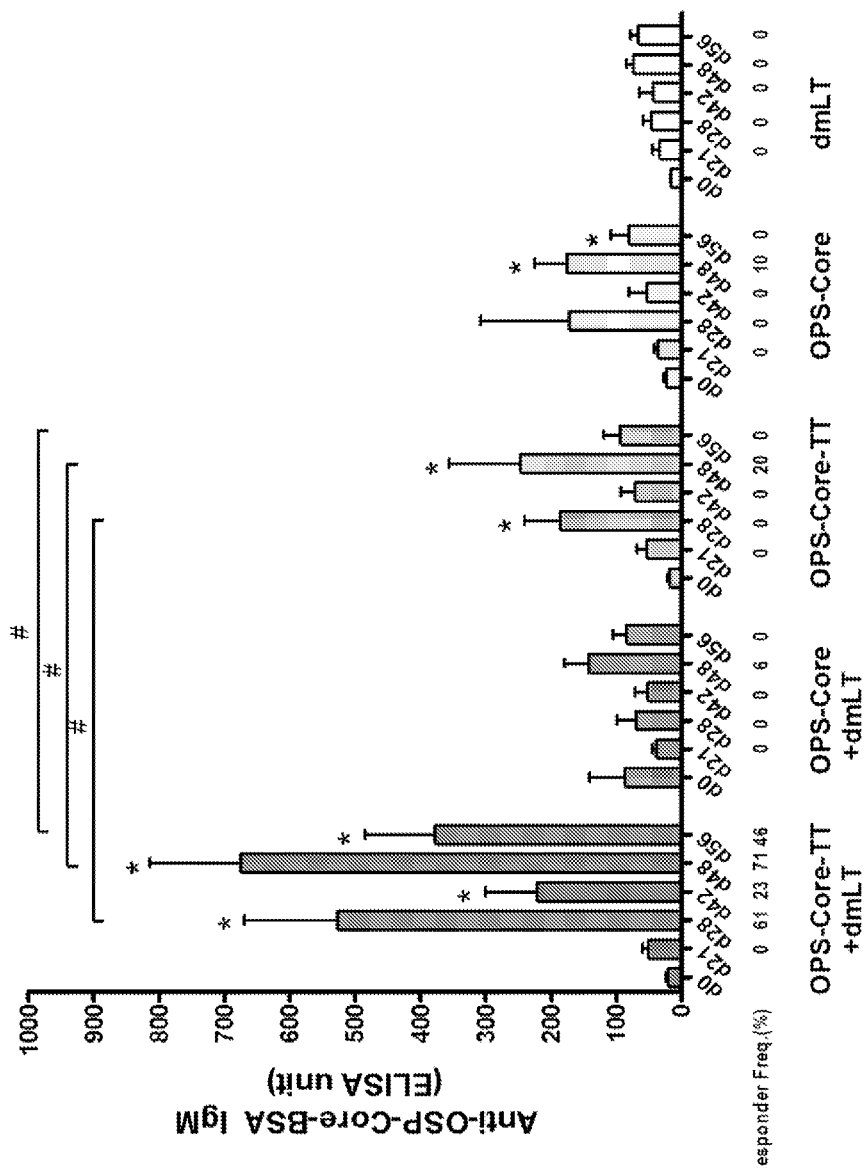
Figure 18D:
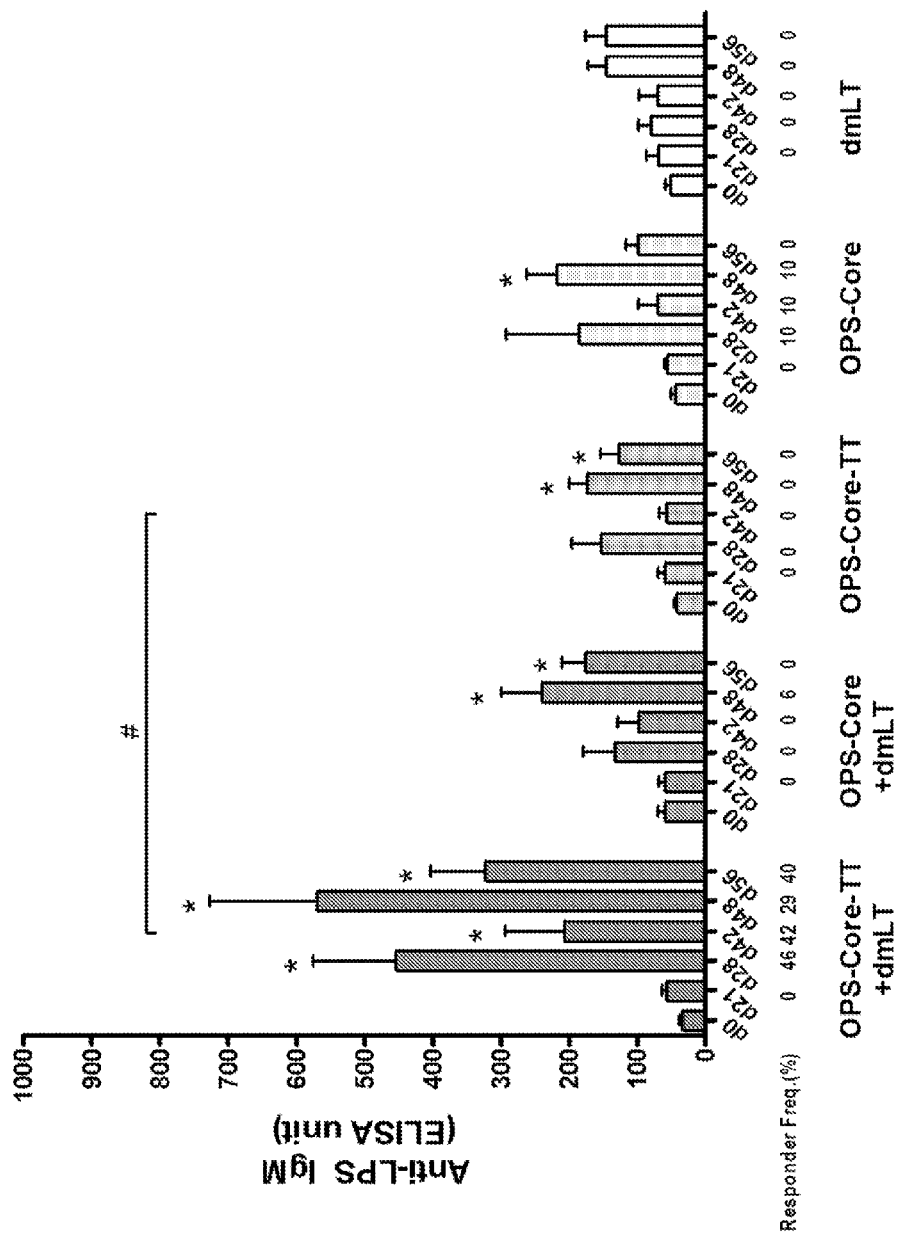
Figure 19:
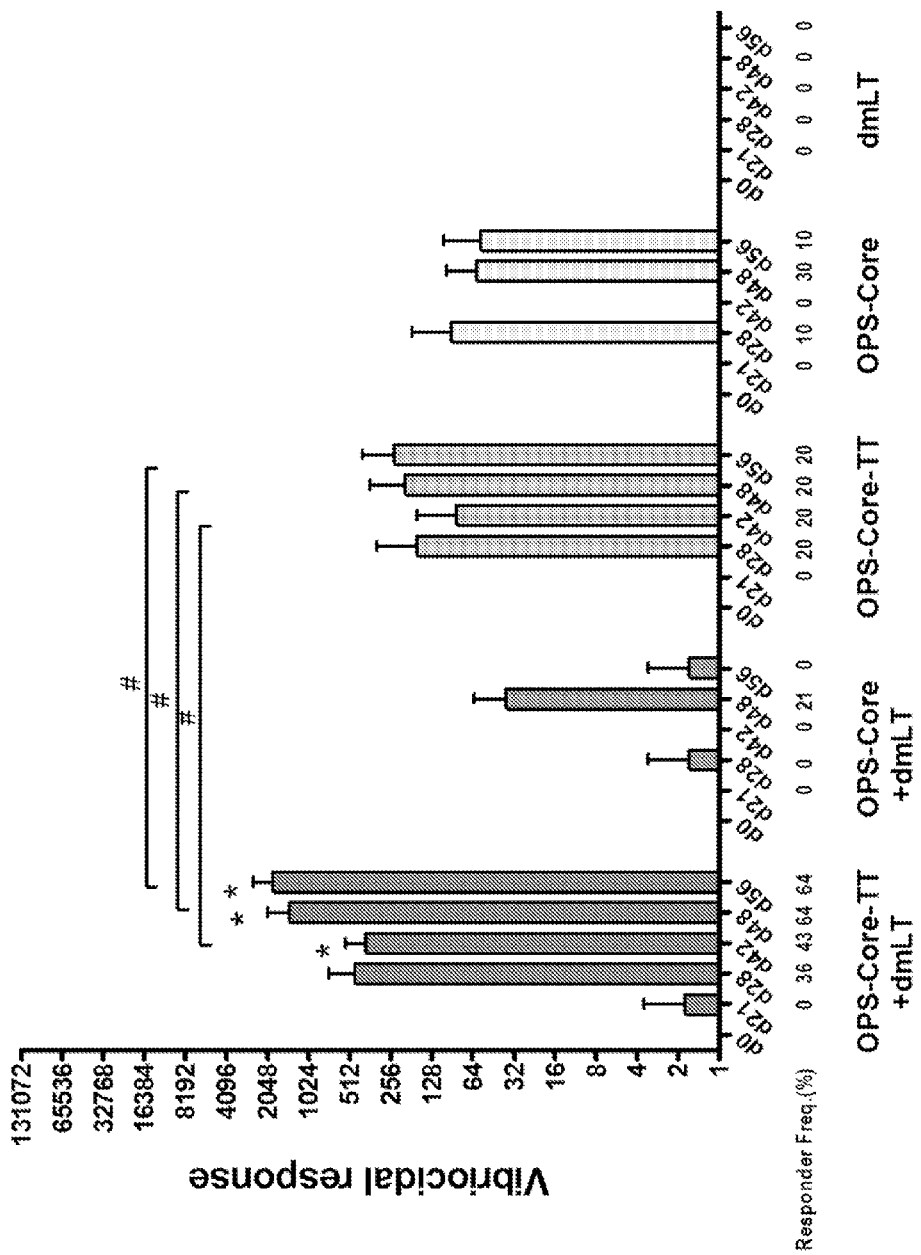
FIG. 19 is a bar graph showing vibriocidal antibody responses in immunized mice serum (mean±SEM, log 2). An asterisk denotes a statistically significant difference (P<0.05) from the baseline (day 0) titer. Responder frequencies are also listed. #, statistically significant difference among the vaccine cohorts (P<0.05).

Importantly, these responses correlated with the vibriocidal response (Ogawa, $R^2=0.74$, $P<0.001$; Inaba, $R^2=0.2$, $P<0.04$; FIG. 7), and these correlation curves mirrored those of the LPS to vibriocidal relationship.

Example 6

Preparation of an O-Specific Polysaccharide (OSP)-Core V. Cholerae O1 Cholera:Tetanus Toxin Heavy Chain Conjugate Vaccine The following examples describe the development of a cholera conjugate vaccine comprising *V. cholerae* O1 Ogawa OSP-core cholera conjugate vaccine coupled to a tetanus toxoid heavy chain fragment (OSP-TThc), and experiments evaluating its efficacy in mice in the presence and absence of an immunoadjuvant. The immunoadjuvant used was dmLT, a non-toxigenic immunoadjuvant derived from heat labile toxin of *E. coli* (Norton et al., Clin Vaccine Immunol 2011; 18(4):546-51).

*V. cholerae* O1 El Tor Ogawa strain X25049 was used to prepare LPS for immunogen preparation and immunological assays, and wild type classical *V. cholerae* O1 classical Ogawa strain O395 was used in vibriocidal assays. 0-specific polysaccharide (O-PS-core) antigen derived from *V. cholerae* O1 Ogawa LPS was conjugated to tetanus toxoid (rTT-Hc) by applying squaric acid chemistry without the use of a linker (FIG. 1D), as described above. Briefly, to produce the conjugate, 3,4-Dimethoxy-3-cyclobutene-1,2-dione was added to a solution of O-PS-core antigen. The resulting solution was dialyzed against pure water and was lyophilized to afford the O-PS-core squarate monomethyl ester.

Recombinant Tetanus Toxin heavy chain (TThc) was obtained as previously described (Bongat et al., Glycoconjugate J., 27: 69-77, 2010). Briefly, an expression plasmid pWVTetHC was constructed by amplification of the receptor-binding domain of tetanus toxin gene using the forward primer TetHCSAP1 fwd (GGTGGTTGCTCTTCCAACATGGGATCCTCAAAAAATCTGGATTGTTGGGTT (SEQ ID NO:4)) and the reverse primer, TetHCPst1 rev (GGTGGTCTGCAGTTCATTAATCATTTGTCCATCCTTCATC (SEQ ID NO:5)). The HC fragment (underlined portion of SEQ ID NO:1 as shown in FIG. 21) was amplified from DNA isolated from the *Clostridium tetani* Massachusetts C2 strain as template. The gel purified PCR fragment was digested with Sap1 and Pst1 and ligated into the Sap1 and Pst1 sites of the intein expression vector pTYB11 (New England Biolabs). This yields a protein, after cleavage of the intein, with the sequence MGS at the amino terminus of TetHC fragment (Fairweather et al., J. Bacteriol. 165, 21-27 (1986)), as shown in FIG. 23. The resulting insert was sequenced to confirm the absence of errors due to PCR; the sequence is shown in FIG. 22.

The pWVTetHC expression vector encodes an amino terminal chimer of tetanus HC fragment intein and chitin binding domain. The HC product was purified in high yield by cleavage of the protein and retained only 1 additional amino acid belonging to the tag.

*E. coli* BL21 (DE3) Star cells were transformed with pWVTetHC on LB ampicillin plates. The transformants were resuspended in 5 ml LB ampicillin (100 μg/ml) and the suspension used to inoculate 1.5 liter of LB ampicillin (100 μg/ml). The culture was shaken at 25° C., 120-170 rpm until the absorbance at 600 nm reached 0.6. The culture was induced by adjusting concentration of IPTG solution to 1 mM solution and shaking the solution overnight at 25° C. The cells were harvested, resuspended in 100 ml column buffer (20 mM HEPES, 500 mM NaCl, pH 7.8) containing two Complete EDTA-free protease inhibitor tablets (Roche). The cells were lysed in a French Pressure cell and centrifuged for 1 hour at 27,000 g and 4° C. Nucleic acids in the lysate supernatant were digested with 2 mg DNAse and 1.5 mg RNAase for 1 hour at 2-8° C.

The lysate supernatant was loaded onto a chitin column equilibrated in column buffer. The column was Washed until all unbound protein detected by absorbance at 280 nm was eluted. To cleave the intein tag, slightly less than 1 column volume of 50 mM DTT in column buffer was introduced, and the column was capped and the mixture was stored at 16° C. for 24-40 hours. The protein was then eluted with column buffer and precipitated from solution by adjusting to 90% saturated ammonium sulfate.

Gel filtration was then performed as follows. The ammonium sulfate precipitate was dissolved in 1-2 ml of 20 mM ammonium acetate and further purified on a Sephacryl S-200 column (280 ml bed volume). The major peak fractions were pooled and lyophilized. The lyophilized protein was stored dry at −20° C.

rTT-Hc and the methyl squarate derivative of the O-PS-core antigen and borate buffer was mixed and the reaction was monitored by SELDI-TOFMS. The reaction was terminated by addition of phosphate buffer and the solution was dialyzed and lyophilized to generate OSP-core-TT conjugate vaccine. Using similar method OSP-core-BSA was also produced for use as a coating antigen in ELISAs to measure immune response.

Example 7

Immunological Evaluation of an O-Specific Polysaccharide (OSP)-Core *V. cholerae* O1 Cholera:Tetanus Toxin Heavy Chain Conjugate Vaccine Cohorts of 10-15 Swiss Webster female mice were immunized intramuscularly with OSP-TT or OSP (10 μg sugar per mice) only, with or without dmLT (5 μg), a non-toxigenic immunoadjuvant derived from heat labile toxin of *E. coli* (Norton et al., Clin Vaccine Immunol 2011; 18:546-51). Mice were immunized on days 0, 21, and 42. Blood samples were collected via tail bleeds on days 0, 21, 28, 42, 49, and 56. Samples were collected, processed, aliquoted, and stored as previously described (Rollenhagen et al., Vaccine 27:4917-2, 2009). The use of animals complied fully with relevant governmental and institutional requirements, guidelines, and policies.

Detection of specific antibodies in serum was performed as follows. Anti-LPS and O-PS-BSA IgG, IgM and IgA responses were quantified in serum using standard enzyme-linked immunosorbent assay (ELISA) protocols (Rollenhagen et al., Vaccine 27:4917-2, 2009). ELISA units were normalized by calculating the ratio of the optical density of the test sample to that of a standard of pooled sera from mice vaccinated with cholera vaccine from a previous study.

The vibriocidal assay was performed as previously described (Crean et al., Infection Immunity 68:977-81, 2000; Butterton et al., Infection Immunity 64:4373-7, 1996). The vibriocidal titer was calculated as the dilution of serum causing 50% reduction in optical density compared with that of wells containing no serum (Ryan et al., Infection Immunity 65:3118-25, 1997; Ryan et al., Infection Immunity 65:2941-9, 1997).

Data from different test groups were compared using Mann Whitney U tests. Within each group, comparisons of data from different time points to baseline data (day 0) were carried out using Wilcoxon Signed Ranks tests. $P<0.05$ was considered a threshold for statistical significance. Statistical analyses were performed using GraphPad Prism 5.

Following the first injection, significant anti-OSP serum IgG antibody responses were detected in mice receiving OSP-TT with or without adjuvant. However, higher magnitude and response rate (P<0.01) was observed in the cohort receiving the conjugate with the adjuvant (Response rate after two doses: 100%) (FIGS. 18A-D). After subsequent doses the antibody level was sustained up to day 56. No anti-OSP IgG responses were detected at any time in animals receiving un-conjugated OSP only, with or without immunoadjuvant, and in animals receiving immunoadjuvant alone. Mice receiving OSP-TT with or without immunoadjuvant, and in mice receiving OSP alone also elicited anti-OSP IgM responses. IgM responses were only detected following a minimum of two immunizations and response frequency and the magnitude were highest in animals receiving OSP-TT with the adjuvant. No significant IgA anti-OSP antibody was detected in any group.

Significant serum anti-LPS IgG responses were developed following a second immunization in the mice receiving the conjugate with or without adjuvant. Anti-LPS IgM responses were detected in all vaccine cohorts except in mice receiving immunoadjuvant alone. Anti-LPS IgA responses were not detected in any group.

Low level vibriocidal responses (magnitude and response frequency) were detected in animals receiving unconjugated OSP only with or without adjuvant. Mice receiving the cholera conjugate OSP-TT vaccine developed a mean reciprocal vibriocidal titer of 128 whereas mice receiving OSP-TT with adjuvant developed a mean reciprocal vibriocidal titer of 2048 conferring the adjuvant effect. The immunoadjuvant alone did not elicit any response.

Evaluation of memory responses was performed using a memory B cell assay as follows. Splenocytes were cultured in 96-well flat bottom plates (Nunc, Nalgene International) supplemented with 8×10$^5$ irradiated spleen feeder cells per well (1200 rad) derived from naive mice. Concavalin A (ConA) supplemented master mix cocktail (20 ng/ml PMA, 2.5 μg/ml ConA, 1 mg/ml R595 LPS, Sigma, St. Louis, Mo.) was added to the wells for stimulation and RPMI alone was added to the control wells. Cells were cultured for 6 days at 37° C., 6% $CO_2$ and 100% humidity. The cells were then transferred to 96-well U-bottom plates (Nunc, Nalgene International) and washed with RPMI complete media. Cell pellet was suspended in 100 ul of RPMI complete media and transferred to nitrocellulose bottomed 96-well plates (Millipore, Bedford, Mass.) previously coated with anti-mouse IgG, IgA (Southern Biotech, Birmingham, Ala.), OSP-core: BSA, CT, LPS and KLH and ELISPOT assay was performed.

The results, shown in Table 1, demonstrate that Parenteral immunization with the cholera conjugate vaccine (OSP-core:TTHc) induces anti-OSP memory B cell responses.

TABLE 1

|   | aOSP-core-BSA | aLPS | aCtxB | aKLH |
|---|---|---|---|---|
| 1. OSP-core-TT + dmLT | 7/11 (64.6%) | 0/11 (0%) | 2/10 (20%) | 0/11 (0%) |
| 2. OSP-core + dmLT | 2/11 (18.2%) | 0/11 (0%) | 0/9 (0%) | 0/11 (0%) |
| 3. OSP-Core-TT | 2/9 (22.2%) | 0/9 (0%) | 1/7 (14%) | 0/9 (0%) |
| 4. OSP-core | 1/9 (11.1%) | 0/9 (0%) | 0/7 (0%) | 0/9 (0%) |
| 5. dmLT | 0/8 (0%) | 0/8 (0%) | 0/7 (0%) | 0/8 (0%) |

Figure 20:
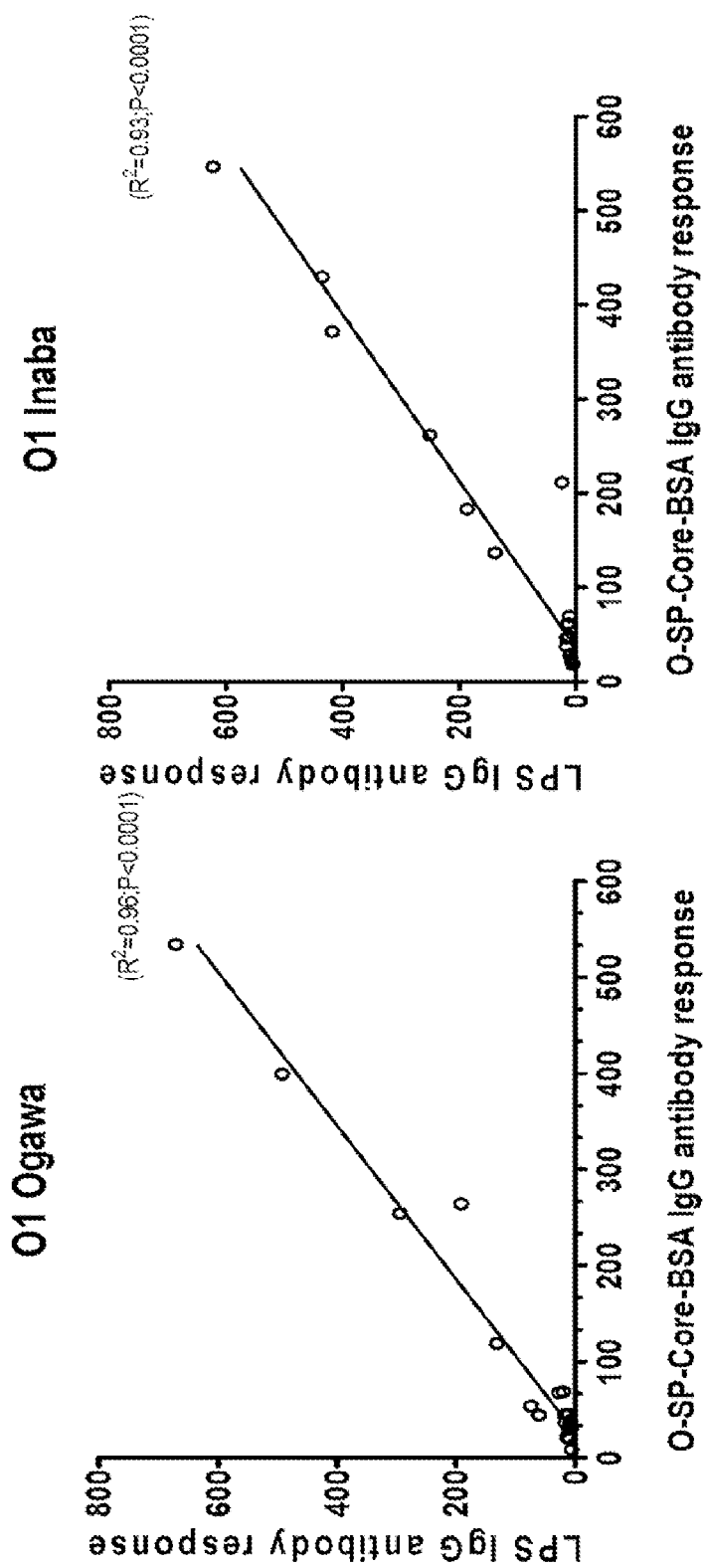
FIG. 20 is a pair of line graphs showing the correlation between anti-*V. cholerae* O1 LPS IgG antibody responses and corresponding OSP-Core-BSA IgG antibody responses. Lines designate the linear correlations between the responses (n=10 in each group).

Furthermore, as shown in FIG. 20 convalescent phase serum from humans recovering from cholera has high level anti-OSP reactivity.

To assess anti-O-PS-core-BSA or anti-BSA IgG responses, blood was used from 10 patients with cholera, collected during the acute phase of illness, and during convalescence. ELISA plates were coated with O-PS-core/BSA (1 μg/mL) or BSA (5 μg/mL) in carbonate buffer pH 9.6, respectively. To each well, 100 μL/well of plasma (diluted 1:50 in 0.1% BSA in phosphate-buffered saline—Tween) was added, and the presence of antigen-specific antibodies detected using horseradish peroxidase-conjugated anti-human IgG antibody. After 1.5 hours incubation at 37° C., the plates were developed with a 0.55 mg/mL solution of 2,2'-azino-bis(3-ethylbenzthiazoline-6-sulphonic acid (ABTS; Sigma) with 0.03% $H_2O_2$ (Sigma), and the optical density at 405 nm was determined with a Vmax microplate kinetic reader (Molecular Devices Corp., Sunnyvale, Calif.). Plates were read for 5 minutes at 14 second intervals, and the maximum slope for an optical density change of 0.2 U was reported as millioptical density units per minute (mOD/min). ELISA units were normalized by calculating the ratio of the optical density of the test sample to that of a standard of pooled convalescent-phase plasma from patients recovered from cholera. Vibriocidal responses were assessed using guinea pig complement and the homologous serotype of V. cholerae O1 Ogawa (X-25049) or Inaba (19479) as the target organism. The vibriocidal titer was defined as the reciprocal of the highest serum dilution resulting in great than 50% reduction of the optical density associated with V. cholerae growth compared to that of the positive control wells without plasma. The magnitude of acute to convalescent phase responses was compared, and significance was tested using Wilcoxon Signed Rank test; linear regression was used for correlation analysis between vibriocidal antibody and antigen-specific antibody responses. All reported P values were two-tailed, with a cutoff of P<0.05 considered a threshold for statistical significance. As shown in FIG. 20, convalescent phase serum from humans recovering from cholera had a high level of anti-OSP reactivity.

This study showed that the cholera conjugate vaccine OSP-TT in the presence of immunoadjuvant can induce O-antigen specific IgG antibody responses in mice after a single dose. The vaccine also elicited vibriocidal antibody responses, anti-LPS antibodies, and anti-OSP memory B cell responses. Development of a cholera conjugate vaccine that induces long term protective immunity is significant.

Example 8

Comparison of Immune Responses to the O-Specific Polysaccharide and Lipopolysaccharide of V. cholerae O1 in Bangladeshi Adult Patients with Cholera Study participants were selected from patients admitted to the International Centre for Diarrhoeal Disease Research, Bangladesh (icddr,b) with severe acute watery diarrhea and with stool cultures positive for V. cholerae O1 or O139. Patients were all adults, 18 years of age or older. Table 2 describes basic demographic information of the patients.

Stored plasma specimens from patients infected with V. cholerae O1 Ogawa (n=17), Inaba (n=15) and O139 (n=15) were analyzed. Samples collected at days 2, 7, 30, 90, 180, 270, and 360 post onset of disease were analyzed for LPS, OSP and vibriocidal antibody responses. In addition, nine patients with *V. cholerae* O1 Ogawa infection were enrolled from September 2011-January 2012 to assess mucosal antibody-secreting cell (ASC) responses to Ogawa OSP, Ogawa-LPS, and cholera toxin B subunit (CtxB) in fresh cells recovered from blood on days 2, 7, and 30 post onset of cholera. Stored antibody-in-lymphocyte supernatant (ALS) samples obtained from days 2 and 7 after onset of disease from Ogawa (n=10) and Inaba (n=10) patients or healthy controls (n=10) were used to further characterize mucosal responses to Ogawa OSP and LPS (Jayasekera et al., J Infectious Diseases 198:1055-61, 2008). The Institutional Review Boards of the icddr,b and the Massachusetts General Hospital approved this study. All study participants gave informed written consent for study enrollment.

TABLE 2

Demographic and clinical characteristics of cholera patients and healthy controls

| Sample type | | No. of patients | Age years (median) |
|---|---|---|---|
| Plasma | Ogawa[1] | 17 | 29 |
| | Inaba[1] | 15 | 30 |
| | O139[2] | 15 | 35 |
| Stool extract | Ogawa[3] | 14 | 29 |
| | Inaba[3] | 14 | 29 |
| ALS | Ogawa[4] | 10 | 33 |
| | Inaba[4] | 10 | 36 |
| | Healthy[5] | 10 | 33 |
| ASC | Ogawa[3] | 9 | 32 |

[1]Specimens were analyzed on day 2 and on follow up days 7, 30, 90, 180, 270, 360);
[2]analyzed on day 2, 7, 21;
[3]analyzed on day 2, 7, 30;
[4]analyzed on day 2, 7; and
[5]analyzed on day 0 for specimens obtained from healthy controls.
ALS, antibody-in-lymphocyte supernatant assay.
ASC, antibody-secreting cell assay.

*V. cholerae* LPS, OSP, and CtxB

*V. cholerae* LPS, OSP-core, and OSPc:BSA conjugates were prepared as previously described (Xu et al., Bioconjug Chem 22:2179-85, 2011). Briefly, LPS was obtained from *V. cholerae* O1, Ogawa (strain X-25049) and Inaba (strain T19479) by hot phenol/water extraction followed by enzymatic treatment (DNase, RNase and protease), and ultracentrifugation (100,000 g for 3 hours) as previously described (Xu et al., Bioconjug Chem 22:2179-85, 2011). The samples were dialyzed against distilled water, freeze-dried, and stored for subsequent use. To define antigens within the LPS preparations to be used in immunological analyses, high resolution LC-MS/MS analysis was performed using an LTQ-Orbitrap XL mass spectrometer (Thermo Fisher Scientific) as previously described (Charles et al., PloS One 4:e6994, 2009). LC-MS/MS data analysis, protein identification and peak list generation were performed using the Proteome Discoverer (Thermo Fisher Scientific) algorithm incorporating the SEQUEST® search engine and Percolator™ (Kall et al., Nat Methods 4:923-5, 2007) as previously described (Lopez et al., J Proteome Res 10:133-42, 2011). MS/MS data were searched using 10 ppm mass accuracy on precursor m/z and a 0.5 Da window on fragment ions. Fully enzymatic tryptic searches with up to three missed cleavage sites were allowed. Oxidized methionines were searched as a variable modification and alkylated cysteines were searched as a fixed modification. *V. cholera* databases (N16961, 0395, and INDRE 9/11) were downloaded from EDMBL and supplemented with common contaminants. Peptides were filtered for each charge state to a false discovery rate (FDR) of 1%, and then grouped peptides into proteins using Occam's razor logic. To generate OSPc:BSA conjugates, a protocol previously described (Xu et al., Bioconjug Chem 22:2179-85, 2011) was used that includes acid hydrolysis, chloroform-based separation and recovery of hydro lysate, size exclusion chromatography, ultracentrifugation, and dialysis. The retentate was lyophilized to afford the OSP-core antigens as white solids, and analysis by $^{13}$C NMR. SELDI-TOF mass spectroscopy indicated that the average molecular mass of the Inaba and Ogawa OSP-core antigens were ~5100 and ~5900 Da, respectively. To facilitate binding to the plastic plates and membranes used in immunologic analyses, OSP-core was conjugated to bovine serum albumin to generate OSPc:BSA as previously described (Xu et al., Bioconjug Chem 22:2179-85, 2011). Briefly, OSP-core for conjugation was modified using squarate derivatization engaging the single amino group present in the core (Vinogradov et al., European Journal Biochemistry/FEBS 233:152-8, 1995), filtration, and dialysis (3000 Da cutoff). The retentate was lyophilized to afford the OSP core squarate monomethyl ester as a white solid. The lyophilate was dissolved in 0.5 M pH 9 borate buffer to yield ~2.5 mM (Inaba) or ~4.9 mM (Ogawa) solutions, with respect to OSP core; BSA was added in the amount to form OSP-core:carrier molar ratios of ca. 11:1 for Inaba and 22:1 for Ogawa. Conjugation was monitored by SELDI-TOF MS at 24, 48, 72, 96, and 240 hours, when the reaction was terminated by addition of 300 µL of pH 7 phosphate buffer. The solution was transferred to centrifugation filtration tubes (30,000 Da cut-off), dialyzed against 10 mM aqueous ammonium carbonate, and lyophilized. On the basis of the average MW of OSP core, the Inaba-core/BSA ratio of the final product was 2.8:1 and the Ogawa-core/BSA ratio was 4.8:1. To assess responses targeting CtxB, recombinant antigen supplied by A. M. Svennerholm, Gothenburg University, Sweden, was used.

Immune Responses in Stored Plasma and ALS Specimens of Study Participants

Anti-LPS and anti-OSP IgG, IgM, and IgA responses in plasma was quantified using an enzyme-linked immunosorbent assay (ELISA) protocol as previously described (Qadri et al., Clinical Diagnostic Laboratory Immunology 2:685-8; Qadri et al., Infect Immun 65:3571-6, 1997; and Xu et al., Bioconjug Chem 22:2179-85, 2011). Briefly, 96-well polystyrene plates (Nunc F) was coated with *V. cholerae* O1 Ogawa or Inaba LPS (2.5 µg/mL) (Qadri et al., Clinical Diagnostic Laboratory Immunology 6:812-8, 1999) dissolved in PBS, or Ogawa or Inaba OSPc:BSA (1 µg of the conjugated product/mL) dissolved in carbonate buffer (pH 9.6). To each well, 100 µL of plasma (diluted 1:40 in 0.1% BSA in phosphate-buffered saline—0.05% Tween) was added and antigen specific antibodies in the sample was detected using horseradish peroxidase-conjugated rabbit anti-human IgA, IgG and IgM as secondary antibodies (Jackson Immunoresearch, West Grove, Pa., 1:1000 dilution). Plates were developed with 1 mg/mL ortho-phenylene diamine (Sigma, St. Louis, Mo.) dissolved in 0.1 M sodium citrate buffer (pH 4.5), with 0.03% $H_2O2$ added, and the optical density at 450 nm was determined by reading the plates kinetically for 5 minutes at 14 second intervals (Jayasekera et J Infectious Diseases 198:1055-61, 2008). The maximum slope for an optical density change of 0.2 U was reported as milli optical density units per minute (mOD/min). The data was normalized to ELISA units by calculating the ratio of the optical density of the test sample to that of a standard of pooled convalescent-phase plasma from patients previously infected with cholera that was included on each plate.

ALS specimens were collected after 48 hours culture as previously described (36). ELISAs using ALS were performed according to the plasma ELISA protocol as outlined above. The ALS samples were diluted 1:2 in 0.1% BSA in phosphate-buffered saline-0.05% Tween, and responses were detected using horseradish peroxidase-conjugated rabbit anti-human IgA as secondary antibody (Jackson Immunoresearch, West Grove, Pa., 1:1000 dilution), with development as above.

Quantification of Circulating IgG, 101, and IgA Antibody-Secreting Cells (ASC) to OSP, LPS, and CtxB Ogawa OSP, Ogawa LPS, and CtxB-specific ASC responses were measured by enzyme-linked immunosorbent spot (ELISPOT) as previously described (Harris et al., Infect Immun 77:3850-6, 2009; Qadri et al., Infect Immun 65:3571-6, 1997; and Shamsuzzaman et al., Vaccine 27:1386-92, 2009). Briefly, nitrocellulose-bottomed plates (Millipore, Bedford, Mass.) were coated with Ogawa OSPc: BSA in carbonate buffer (pH 9.6) (10 µg of conjugate/mL), Ogawa LPS (25 µg/ml), affinity-purified goat anti-human Ig (5 µg/ml; Jackson Immunology Research, West Grove, Pa.), monosialotetrahexosylganglioside (GM1 ganglioside) (3 nM), or keyhole limpet hemocyanin (KLH) (2.5 µg/ml), and were incubated overnight at 4° C. (Qadri et al., Infect Immun 65:3571-6, 1997). Prior to blocking, CtxB (2.5 µg/ml) was added to the GM1-coated plates, and the plates were incubated for 1 hour at 37° C. All plates were then blocked for 2 hours at 37° C. prior to use, with RPMI 1640 containing 10% fetal bovine serum. PBMCs were harvested as previously described by centrifugation of diluted whole-blood samples on Ficoll-Isopaque (Pharmacia, Piscataway, N.J.) (Jayasekera et al., J Infectious Diseases 198:1055-61, 2008). A total of $6 \times 10^5$ PBMCs/well were added to the OSPc:BSA, LPS, and CtxB-coated plates, while $1 \times 10^5$ PBMCs/starting well were added to the total Ig-coated plates and serially diluted. After incubating the plates at 37° C. for 3 hours, plates were washed and IgG, IgM and IgA ASCs were detected using horseradish peroxidase-conjugated mouse anti-human IgA and IgM (Hybridoma Reagent Laboratory, Baltimore, Md.), and alkaline phosphatase-conjugated IgG (Southern Biotech, Birmingham, Ala.), both diluted 1:500. After overnight incubation at 4° C., IgG-conjugated plates were developed with 5-bromo-4-chloro-3-indolyl-phosphate-nitroblue tetrazolium. IgA and IgM-conjugated plates were developed with 3-amino-9-ethylcarbazole. ASC were independently quantified by two individuals using a stereomicroscope (Leica WILD M3Z). KLH (Pierce Biotechnology, Rockford, Ill.) coated plates were used as a negative control. The number of antigen-specific IgG, IgM, and IgA ASC were expressed per $10^6$ PBMCs.

Vibriocidal Assay and Vibriocidal Inhibition Assay with OSP and LPS

Vibriocidal antibody responses was assessed as previously described, using guinea pig complement and the homologous serotype of *V. cholerae* O1 Ogawa (X-25049) or Inaba (T19479) as the target organism (Alam et al., Clinical and Vaccine Immunology 18:844-50, 2011; Harris et al., Infect Immun 77:3850-6, 2009; Qadri et al., Clinical Diagnostic Laboratory Immunology 2:685-8, 1995; Qadri et al., Infect Immun 65:3571-6, 1997; and Xu et al., Bioconjug Chem 22:2179-85, 2011). The vibriocidal titer was defined as the reciprocal of the highest serum dilution resulting in >50% reduction of the optical density associated with *V. cholerae* growth compared to that of the positive control wells without plasma.

The vibriocidal inhibition assay was performed as previously described (Finkelstein, Journal Immunology 264-271, 1962; Gupta et al., Infect Immun 66:3095-9. 1998; and Kossaczka et al., Infect Immun 68:5037-43, 2000). In brief, after heat inactivation of day 7 plasma at 56° C. for 30 min, Ogawa OSPc:BSA and LPS at concentrations of 1, 10, and 100 µg/mL were mixed with diluted plasma (1:160) and incubated at 37° C. while gently shaking for 1 hour. The same concentrations of BSA and CtxB were also incubated with diluted plasma as controls, in addition to plasma without any antigen added. These samples were then used to assess the vibriocidal titer of the plasma using the standard vibriocidal assay protocol above (Alam et al., Clinical and Vaccine Immunology 18:844-50, 2011; Harris et al., Infect Immun 77:3850-6, 2009; Qadri et al., Clinical Diagnostic Laboratory Immunology 2:685-8, 1995; Qadri et al., Infect Immun 65:3571-6, 1997; and Xu et al., Bioconjug Chem 22:2179-85, 2011).

ELISAs for IgA Specific to Ogawa OSP and LPS in Fecal Extracts

An ELISA format was used to determine the total IgA content in fecal samples using pooled human Swedish milk with a known IgA concentration of 1 mg/ml as the standard, with affinity purified goat antibodies to the F(ab')2 fragment of human immunoglobulin as the capture antibody (Jackson ImmunoResearch Laboratories Inc., West Grove, Pa.), as previously described (Qadri et al., Clinical Diagnostic Laboratory Immunology 558 4:429-34, 1997; and Svennerholm et al., Journal Infectious Diseases 149:884-93, 1984); detection was with goat anti-human immunoglobulin specific to IgA, conjugated to horseradish peroxidase as the secondary antibody (Jackson Immunoresearch, West Grove, Pa., 1:3000 dilution). Anti-Ogawa OSP and LPS IgA responses in fecal extracts were detected using rabbit anti-human immunoglobulin specific to IgA conjugated to horseradish peroxidase as the secondary antibody (Jackson Immunoresearch, West Grove, Pa., 1:1000 dilution). Responses were measured kinetically and expressed as mAB per minute per microgram of total IgA in fecal extracts. Patients whose fecal IgA responses to Ogawa OSP and LPS at convalescence (day 7 and/or day 30) doubled in comparison to day 2 levels were considered responders.

Statistical Analyses

The magnitude of acute to convalescent phase responses was compared using the Wilcoxon Signed Rank test, and the Mann-Whitney U test was used to compare between the immune responses to OSPc:BSA, LPS, and healthy controls. All reported P values were two-tailed, with a cutoff of P<0.05 considered a threshold for statistical significance. Pearson's product moment correlation analysis was performed using SigmaStat 3.1 (Systat Software, San Jose, Calif.) for correlations between vibriocidal antibody and antigen-specific antibody responses.

Analysis of LPS and OSPc:BSA

MS analysis of the two *V. cholerae* LPS preparations disclosed a total of 610 proteins, including many extracellular and membrane proteins such as flagellin A, starvation lipoprotein Slp-like protein, a number of methyl accepting chemotaxis proteins (VC1248, VCA0906), and general secretion pathway proteins (EpsD, EpsI, EpsN). Of the 396 proteins with functional annotations in the J. Craig Venter Institute database, the most highly represented groups included hypothetical proteins, cellular processes and pathogenesis, and energy metabolism. SELDI analysis of Inaba OSPc:BSA after freeze-drying showed that the average molecular mass of the conjugate obtained was 81,000 Da (molar ratio OSP-core:BSA=~2.8). The conjugate still contained ~5% of the unchanged BSA (Xu et al., Bioconjug Chem 22:2179-85, 2011). SELDI analysis of Ogawa OSPc:

BSA after freeze-drying showed that the average molecular mass of the conjugate obtained was 95,000 Da (molar ratio OSP-core:BSA=~4.8); unconjugated BSA was not detected (Xu et al., Bioconjug Chem 22:2179-85, 2011).

Figure 24:
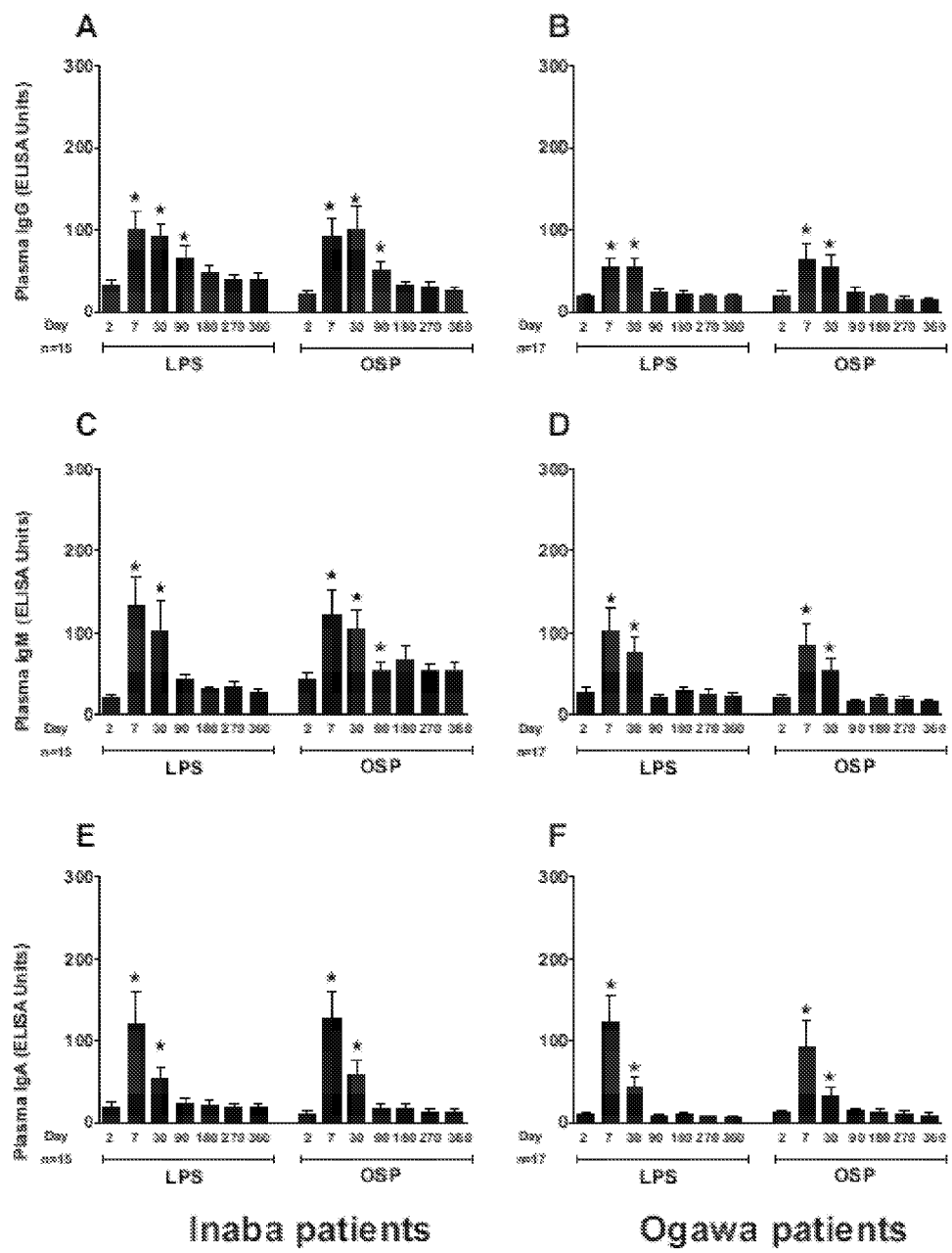
Figure 25:
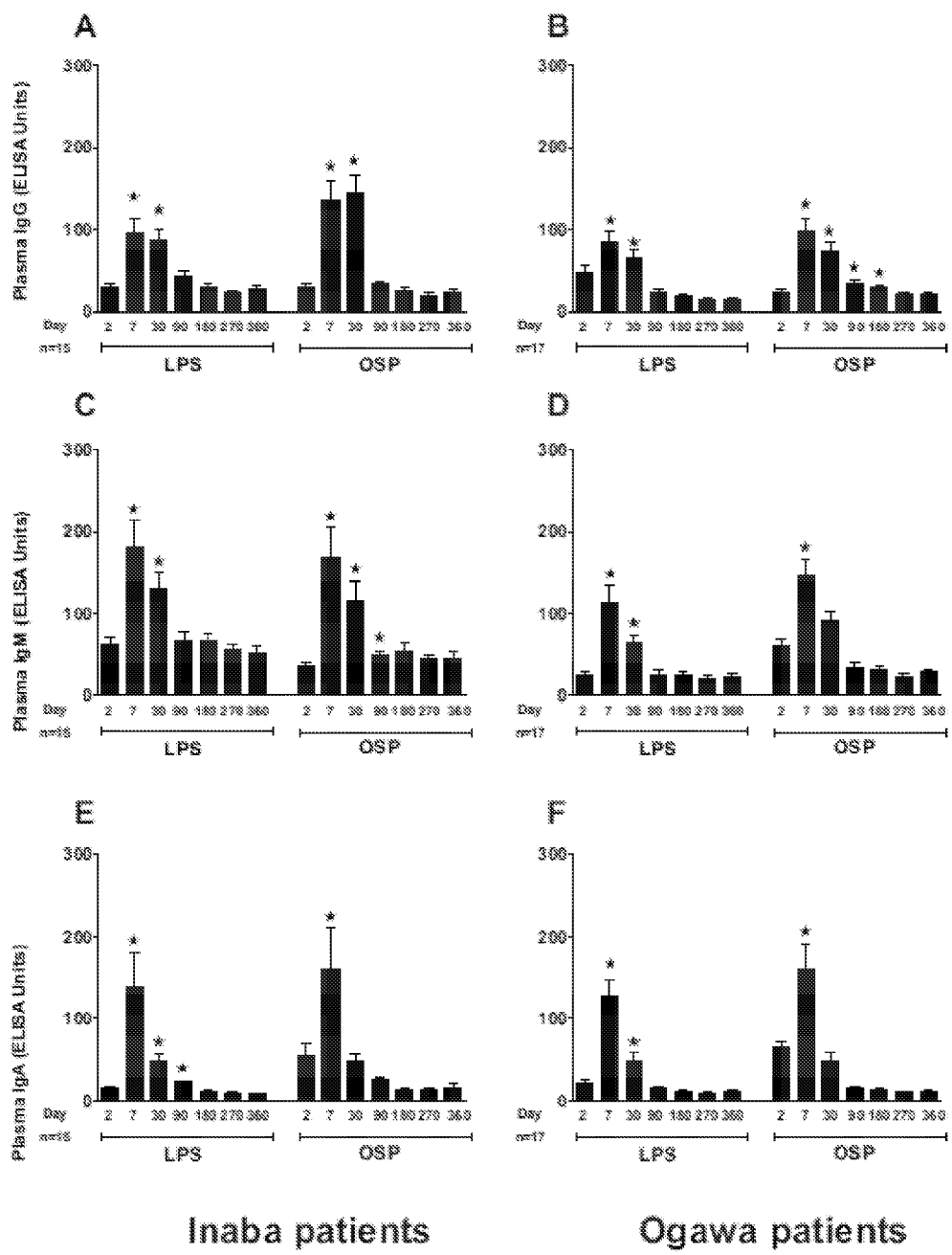

IgG, IgM, and IgA Responses to *V. cholerae* O1 Ogawa and Inaba OSP and LPS Antigens Prominent reactivity of convalescent phase sera from patients recovering from cholera was found using OSP-core:BSA, but not unconjugated OSP-core, presumably through improved binding of the polysaccharide-conjugate antigens to assay wells (Fattom et al., Infect Immun 61:1023-32, 1993). Plasma IgG, IgM, and IgA antibody responses were measured to Ogawa and Inaba OSPc:BSA and LPS antigens over a one year period post-infection in patients infected with *V. cholerae* O1 Ogawa and Inaba, and responses in O139 patients to Ogawa OSPc:BSA over a 21 day period. As described below, prominent responses were found targeting O1 OSP-core:BSA in patients recovering from O1 serogroup cholera, but such responses was not detected in patients recovering from O139 serogroup cholera, despite the fact that these serogroups share identical core oligosaccharides (Cox et al., Carbohydrate Research 290:43-58, 1996; Cox et al., Carbohydrate Research 290:59-65, 1996), suggesting that the measured responses were specific to the OSP component of the conjugates, and not to the core or protein components. Henceforth, the responses in immunologic assays using OSP-core:BSA are referred to as targeting OSP. Responses in Ogawa and Inaba patients was assessed to both the homologous and heterologous OSP and LPS O1 antigens. The IgG, IgM, and IgA antibody responses to Inaba OSP and LPS were similar among Ogawa and Inaba patient groups (FIG. 24). Both patient groups showed significantly elevated antibody responses to Inaba OSP and LPS at day 7 post-onset of disease compared to baseline. Correlations between antibody responses to Inaba OSP and LPS in Inaba infected patients over the one year follow up period were strong (IgG, R=0.86, IgM, 0.73, IgA, 0.91 $p<0.01$, respectively). Likewise, Ogawa and Inaba patients demonstrated similar antibody responses to Ogawa OSP and LPS (FIG. 25). Correlations between antibody responses to Ogawa OSP and LPS in Ogawa infected patients over the one year follow up period mirrored those seen in Inaba infected patients (IgG, R=0.60; IgM, 0.60; IgA, 0.92, $p<0.01$).

IgG, IgM, and IgA antibody responses in Inaba patients were cross reactive to the Ogawa OSP antigen when plasma specimens were tested (FIGS. 25A, C, E). Similarly, antibodies from Ogawa patients were cross reactive to the Inaba OSP antigen (FIGS. 24B, D, F). However, as mentioned above, cholera patients infected with *V. cholerae* O139 showed no responses to Ogawa OSPc:BSA or LPS.

Figure 26A:
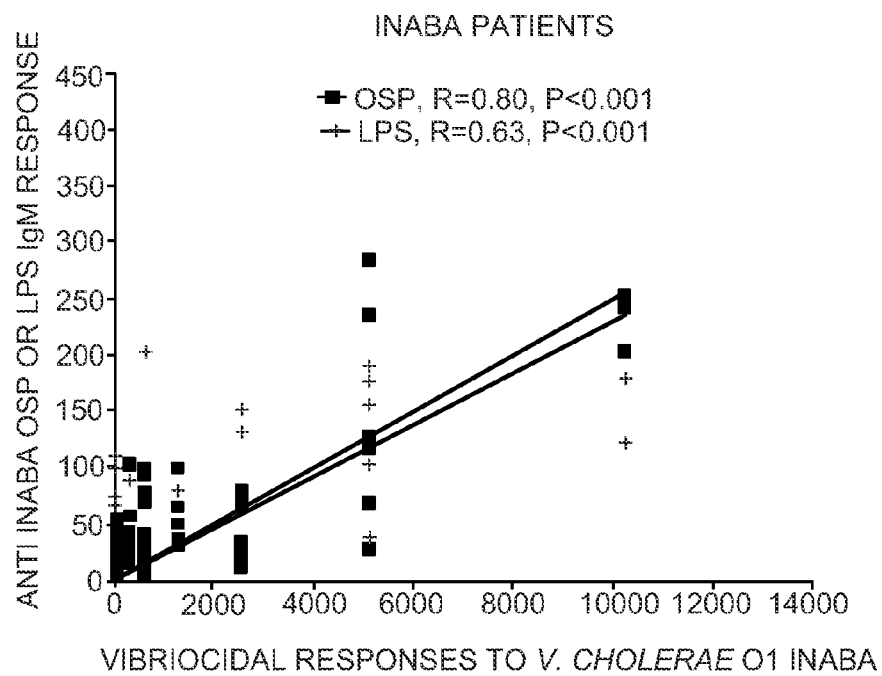
Figure 26B:
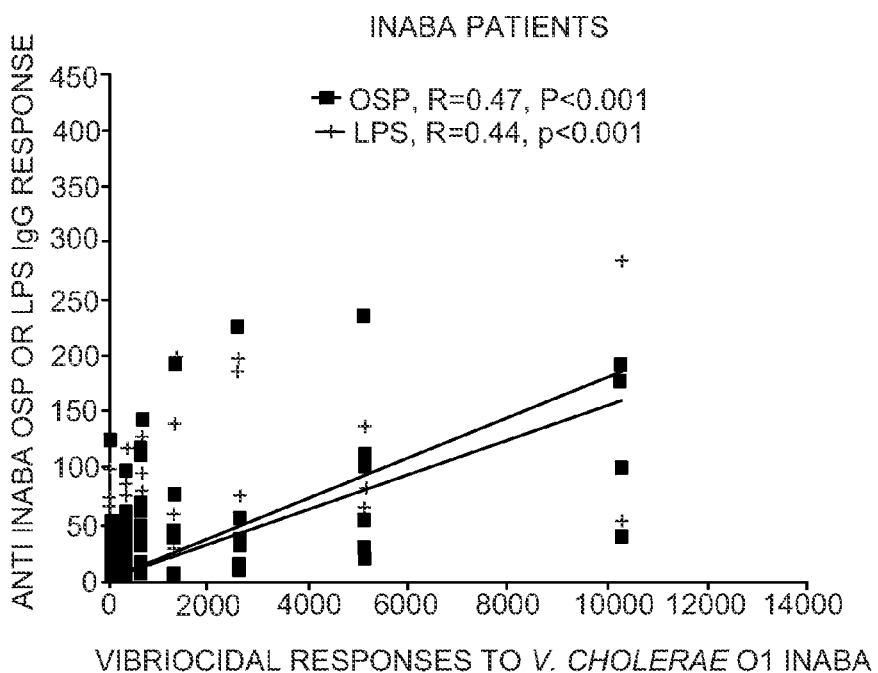
Figure 26C:
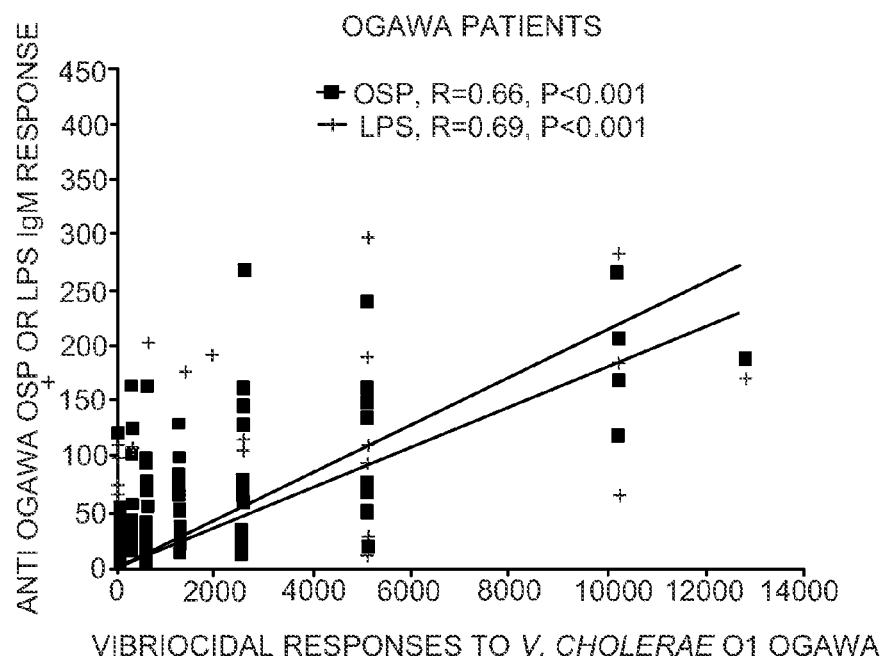
Figure 26D:
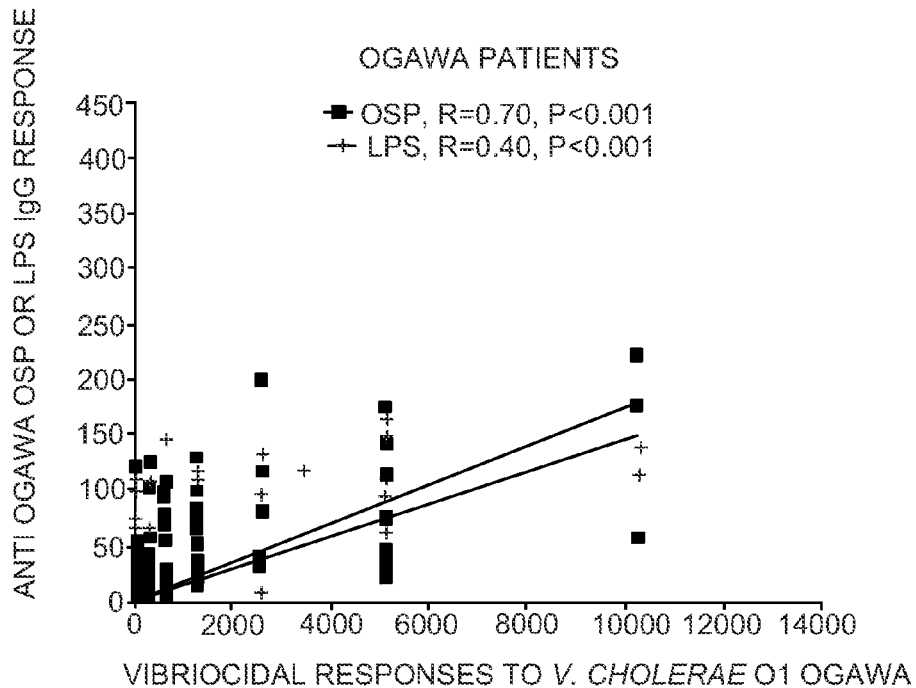

Comparison of Plasma Antibody Responses to OSP and LPS with Vibriocidal Antibody Responses Vibriocidal antibody responses in 15 Inaba patients were compared to plasma IgM and IgG responses to Inaba OSP and LPS (FIGS. 26A, B). The IgM responses to Inaba OSP and LPS were strongly correlated with vibriocidal responses (R=0.80, R=0.63, $p<0.001$, respectively) (FIG. 26A). Inaba OSP and LPS responses in the IgG isotype were less strongly correlated with vibriocidal responses (R=0.47, R=0.44, $p<0.001$, respectively) (FIG. 26B). Vibriocidal responses in 17 Ogawa patients were also compared to plasma IgM and IgG responses to Ogawa OSP and LPS (FIGS. 26C, D). IgM responses in these patients to Ogawa OSP and LPS correlated with vibriocidal responses (R=0.66, R=0.69, $p<0.001$, respectively) (FIG. 26C); IgG responses were similarly correlated (R=0.70 OSP, R=0.40 LPS, $p<0.001$) (FIG. 26D).

Mucosal Immune Responses to *V. cholerae* O1 Ogawa OSP and LPS Antigens

Antibody-secreting cell (ASC) and antibody-in-lymphocyte supernatant (ALS) responses are considered to be surrogate markers of mucosal immunity (Czerkinsky et al., Proc Natl Acad Sci USA 84:2449-53, 1987) and reflect transient circulation of mucosal lymphocytes in blood that are re-horning to mucosal surfaces as they mature; these responses peak on day 7 after mucosal stimulation (Qadri et al., Infect Immun 71:4808-14, 2003). IgG, IgM, and IgA ASC responses to Ogawa OSP, LPS, and CtxB were assessed in peripheral blood of nine *V. cholerae* O1 infected patients. ASC responses to both OSP and LPS were comparable (FIG. 27A). The responses of all three antibody isotypes to OSP and LPS peaked on day 7, and returned to baseline by day 30. IgA and IgG CtxB ASC responses were elevated at day 7; however, IgM ASC responses specific for CtxB were not seen.

Mucosal immune responses to Ogawa OSP and LPS were also assessed using stored ALS specimens from patients infected with O1 Ogawa and O1 Inaba *V. cholerae*. IgA responses targeting OSP and LPS in these ALS specimens were similar, with significant increases seen at 7 days post-infection compared to those from day 2 after illness onset, and compared to those seen in healthy controls (FIG. 27B).

Antigen specific responses on day 2, 7, and 30 post-infection in fecal extracts were further assessed by comparing anti-Ogawa OSP and LPS responses in patients infected with *V. cholerae* O1 Ogawa or Inaba. Eighty-six percent of Ogawa infected patients had a detectable IgA response to homologous LPS and 78% to homologous OSP by convalescence (day 7 or 30 post infection). For patients infected with O1 Inaba, 57% had detectable responses to Ogawa LPS and 50% to Ogawa OSP.

Vibriocidal Inhibition Assay Using OSP and LPS Antigens

Figure 28:
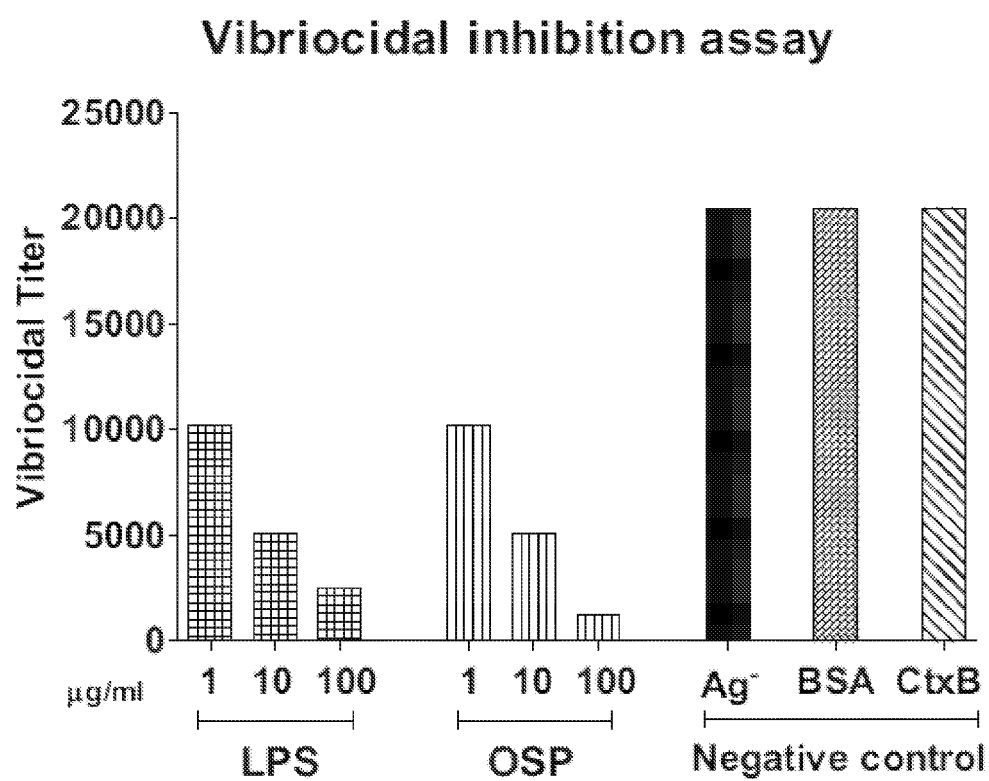

A vibriocidal inhibition assay was used to assess whether antibody contributing to the vibriocidal response was specific to OSP, using Ogawa OSPc:BSA antigen for absorption of plasma from Ogawa-infected patients. These results indicate that increasing concentrations of both Ogawa OSPc:BSA and Ogawa LPS inhibited the vibriocidal assay in a concentration dependent manner that was similar for the two antigens (FIG. 28). Pre-incubating patient serum with CtxB or the negative control antigen BSA had no effect on the vibriocidal assay.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A conjugate molecule comprising:

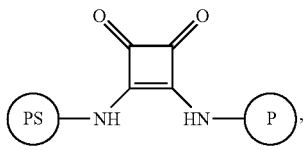

wherein P is a protein, PS is a polysaccharide from lipopolysaccharide comprising an O-polysaccharide (O-PS) and a core (O-PS-Core), and the conjugate molecule is prepared by a method comprising conjugation of the O-PS-Core directly to the alkyl squarate via a free amine inherently present in the O-PS-Core such that there are no intervening linkers between the P, squarate, and O-PS-Core.

2. The conjugate molecule of claim 1, wherein PS is a bacterial polysaccharide or an antigenic fragment thereof comprising an O-PS and an O-PS-Core, and P is a carrier protein.

3. The conjugate molecule of claim 1, wherein PS is a detoxified bacterial polysaccharide or a fragment thereof comprising an O-PS and an O-PS-Core.

4. The conjugate molecule of claim 1, wherein PS comprises one or more of *Escherichia coli* O-PS-Core, *Shigella* O-PS-Core, *Enterobacteriaceae* O-PS-Core, *Pseudomonas* sp. O-PS-Core, *P. aeruginosa* O-PS-Core, *Moraxella* sp. O-PS-Core, *Helicobacter* O-PS-Core, *Stenotrophomonas* O-PS-Core, *Bdellovibrio* O-PS-Core, acetic acid bacteria O-PS-Core, *Legionella* O-PS-Core, *Wolbachia* O-PS-Core, cyanobacteria O-PS-Core, *Spirochaetes* O-PS-Core, green sulfur bacteria O-PS-Core, green non-sulfur bacteria O-PS-Core, *Neisseria* sp. O-PS-Core, *N. gonorrhoeae* O-PS-Core, *Meningitis* sp. O-PS-Core, *N. meningitides* O-PS-Core, *Moraxella* O-PS-Core, *M. catarrhalis* O-PS-Core, *Hemophilus* sp. O-PS-Core, *H. influenza* O-PS-Core, *Klebsiella* sp. O-PS-Core, *K. pneumonia* O-PS-Core, *Legionella* sp. O-PS-Core, *L. pneumophila* O-PS-Core, *Proteus mirabilis* O-PS-Core, *Enterobacter cloacae* O-PS-Core, *Serratia marcescens* O-PS-Core, *Helicobacter* sp. O-PS-Core, *H. pylori* O-PS-Core, *Salmonella* sp. O-PS-Core, *S. enteritidis* O-PS-Core, *Salmonella typhi* O-PS-Core, *Acinetobacter baumannii* O-PS-Core, *V. cholera* O-PS-Core, *V. cholerae* Inaba O-PS-Core, *V. cholerae* Ogawa O-PS-Core, an antigenic fragment comprising an O-PS and an O-PS-Core of the one or more polysaccharides, or any combination thereof.

5. The conjugate molecule of claim 1, wherein PS is *V. cholerae* O-PS-Core or an antigenic fragment thereof comprising an O-PS and an O-PS-Core, *V. cholerae* Inaba O-PS-Core or an antigenic fragment thereof comprising an O-PS and an O-PS-Core, *V. cholerae* Ogawa O-PS-Core or an antigenic fragment thereof comprising an O-PS and an O-PS-Core, or any combination thereof.

6. A method of manufacturing the conjugate molecule of claim 1, the method comprising:
  (a) treating a polysaccharide from lipopolysaccharide comprising an O-polysaccharide (O-PS) and a core (O-PS-Core) having at least one accessible amine group with an alkyl squarate in the presence of a first buffer to manufacture a polysaccharide squarate monoester; and
  (b) treating the polysaccharide squarate monoester with the protein in the presence of a second buffer, to thereby manufacture the conjugate molecule wherein there are no intervening linkers between the P, squarate, and O-PS-Core.

7. The method of claim 6, wherein the first buffer comprises a buffer of about pH 7.0.

8. The method of claim 6, wherein the second buffer comprises a buffer of about pH 9.0.

9. The method of claim 6, wherein the first buffer comprises a phosphate buffer.

10. The method of claim 6, wherein the second buffer comprises a borate buffer.

11. The method of claim 6, wherein the alkyl squarate is selected from the group consisting of dimethyl squarate, diethyl squarate, dipropyl squarate, dibutyl squarate, and didecyl squarate.

12. The method of claim 6, wherein the alkyl squarate is dimethyl squarate.

13. The method of claim 6, wherein the molar ratio of polysaccharide to the alkyl squarate is between about 1:1 to about 50:1.

14. The method of claim 6, wherein the molar ratio of polysaccharide squarate monoester to the protein is between about 1:1 to about 50:1.

15. A conjugate molecule comprising:

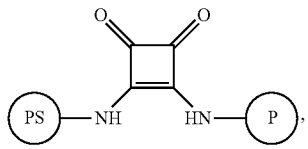

wherein P is tetanus toxin or a fragment thereof, PS is a *V. cholerae* O-PS-Core, and the conjugate molecule is prepared by a method comprising conjugation of the O-PS-Core directly to the alkyl squarate via a free amine inherently present in the O-PS-Core such that there are no intervening linkers between the P, squarate, and O-PS-Core.

16. The conjugate molecule of claim 15, wherein P comprises Tetanus Toxin C-fragment.

17. The conjugate molecule of claim 15, wherein PS comprises *V. cholerae* Inaba O-PS-Core, and/or *V. cholerae* Ogawa O-PS-Core.

18. The conjugate molecule of claim 15, wherein PS comprises *V. cholerae* O1 Ogawa O-PS-Core.

* * * * *

SEQUENCE LISTING

<160> NUMBER OF SEQ ID NOS: 5

<210> SEQ ID NO 1
<211> LENGTH: 4338
<212> TYPE: DNA
<213> ORGANISM: Clostridium tetani

<400> SEQUENCE: 1

```
ccttcatatg agtcgtcaag ctgtatataa aaataaggtt ttagcattaa aaaaattaga         60
acctatagta aataaattaa ttaatatata gttttttataa tttaattatg aataatattc        120
ttaagataaa aagtaaattt ttaaaaattt aaattttcag tttacaaaaa ataacctgat        180
tatgttatat gtaattgtaa aaaacatata aaaaatcaga aaaatttagg aggtatatta        240
ttaatggatt aaataataat ttttttaattt actttttgatt aataaatatt aaatgtttat      300
tttaattagg agatgatacg tatgccaata accataaata atttttagata tagtgatcct      360 gttaataatg atacaattat tatgatggag ccaccatact gtaagggtct agatatctat      420
tataaggctt tcaaaataac agatcgtatt tggatagtgc cggaaaggta tgaatttggg      480
acaaaacctg aagattttaa cccaccatct tcattaatag aaggtgcatc tgagtattac      540
gatccaaatt atttaaggac tgattctgat aaagatagat ttttacaaac catggtaaaa      600
ctgtttaaca gaattaaaaa caatgtagca ggtgaagcct tattagataa gataataaat      660
gccataccct accttggaaa ttcatattcc ttactagaca agtttgatac aaactctaat      720
tcagtatctt ttaattttatt agaacaagac cccagtggag caactacaaa atcagcaatg      780
ctgacaaatt taataatatt tggacctggg cctgttttaa ataaaaatga ggttagaggt      840
attgtattga gggtagataa taaaaattac ttcccatgta gagatggttt tggctcaata      900
atgcaaatgg cattttgccc agaatatgta cctacctttg ataatgtaat agaaaatatt      960
acgtcactca ctattggcaa aagcaaatat tttcaagatc cagcattact attaatgcac     1020
gaacttatac atgtactaca tggtttatac ggaatgcagg tatcaagcca tgaaattatt     1080
ccatccaaac aagaaattta tatgcagcat acatatccaa taagtgctga agaactattc     1140
acttttggcg acaggatgc taatcttata agtattgata taaaaaacga tttatatgaa     1200
aaaactttaa atgattataa agctatagct aacaaactta gtcaagtcac tagctgcaat     1260
gatcccaaca ttgatattga tagctacaaa caaatatatc aacaaaaata tcaattcgat     1320
aaagatagca atggacaata tattgtaaat gaggataaat ttcagatact atataatagc     1380
ataatgtatg gttttacaga gattgaattg ggaaaaaaat ttaatataaa aactagactt     1440
tcttatttta gtatgaatca tgaccctgta aaaattccaa atttattaga tgatacaatt     1500
tacaatgata cagaaggatt taatatagaa agcaaagatc tgaaatctga atataaagga     1560
caaaatatga gggtaaatac aaatgctttt agaaatgttg atggatcagg cctagttcca     1620
aaacttattg gcttatgtaa aaaaattata ccaccaacaa atataagaga aaatttatat     1680
aatagaactg catcattaac agatttagga ggagaattat gtataaaaat taaaaatgaa     1740
gatttaactt ttatagctga aaaaaatagc ttttcagaag aaccatttca agatgaaata     1800
gttagttata atacaaaaaa taaccattta aatttttaatt attcgctaga taaaattatt     1860
gtagattata atctacaaag taaaattaca ttacctaatg ataggacaac cccagttaca     1920
aaaggaattc catatgctcc agaatataaa agtaatgctg caagtacaat agaaatacat     1980
aatattgatg acaatacaat atatcaatat ttgtatgctc aaaaatctcc tacaactcta     2040
caaagaataa ctatgactaa ttctgttgat gacgcattaa taaattccac caaaatatat     2100
```

```
tcatattttc catctgtaat cagtaaagtt aaccaaggtg cacaaggaat tttattctta      2160
cagtgggtga gagatataat tgatgatttt accaatgaat cttcacaaaa aactactatt      2220
gataaaattt cagatgtatc cactattgtt ccttatatag gacccgcatt aaacattgta      2280
aaacaaggct atgagggaaa ctttataggc gctttagaaa ctaccggagt ggttttatta      2340
ttagaatata ttccagaaat tactttacca gtaattgcag ctttatctat agcagaaagt      2400
agcacacaaa aagaaaagat aataaaaaca atagataact ttttagaaaa aagatatgaa      2460
aaatggattg aagtatataa actagtaaaa gcaaatggt taggcacagt taatacgcaa       2520
ttccaaaaaa gaagttatca aatgtataga tctttagaat atcaagtaga tgcaataaaa      2580
aaaataatag actatgaata taaaatatat tcaggacctg ataaggaaca aattgccgac      2640
gaaattaata atctgaaaaa caaacttgaa gaaaaggcta ataaagcaat gataaacata      2700
aatatattta tgagggaaag ttctagatca tttttagtta atcaaatgat taacgaagct      2760
aaaaagcagt tattagagtt tgatactcaa agcaaaaata ttttaatgca gtatataaaa      2820
gcaaattcta aatttatagg tataactgaa ctaaaaaaat tagaatcaaa aataaacaaa      2880
gttttttcaa caccaattcc atttttcttat tctaaaaatc tggattgttg ggttgataat      2940
gaagaagata tagatgttat attaaaaaag agtacaattt taaatttaga tattaataat      3000
gatattatat cagatatatc tgggtttaat tcatctgtaa taacatatcc agatgctcaa      3060
ttggtgcccg gaataaatgg caaagcaata catttagtaa acaatgaatc ttctgaagtt      3120
atagtgcata aagctatgga tattgaatat aatgatatgt ttaataattt taccgttagc      3180
ttttggttga gggttcctaa agtatctgct agtcatttag aacaatatgg cacaaatgag      3240
tattcaataa ttagctctat gaaaaaacat agtctatcaa taggatctgg ttggagtgta      3300
tcacttaaag gtaataactt aatatggact ttaaaagatt ccgcgggaga agttagacaa      3360
ataactttta gggatttacc tgataaattt aatgcttatt tagcaaataa atgggttttt      3420
ataactatta ctaatgatag attatcttct gctaatttgt atataaatgg agtacttatg      3480
ggaagtgcag aaaattactg ggtttaggagct attagagagg ataataatat aacattaaaa      3540
ctagatagat gtaataataa taatcaatac gtttctattg ataaatttag gatattttgc      3600
aaagcattaa atccaaaaga gattgaaaaa ttatacacaa gttatttatc tataacccttt      3660 ttaagagact tctggggaaa ccctttacga tatgatacag aatattattt aataccagta      3720
gcttctagtt ctaaagatgt tcaattgaaa aatataacag attatatgta tttgacaaat      3780
gcgccatcgt atactaacgg aaaattgaat atatattata gaaggttata taatggacta      3840
aaatttatta taaaaagata tacacctaat aatgaaatag attcttttgt taaatcaggt      3900
gattttatta aattatatgt atcatataac aataatgagc acattgtagg ttatccgaaa      3960
gatggaaatg cctttaataa tcttgataga attctaagag taggttataa tgccccaggt      4020
atccctcttt ataaaaaaat ggaagcagta aaattgcgtg atttaaaaac ctattctgta      4080
caacttaaat tatatgatga taaaaatgca tctttaggac tagtaggtac ccataatggt      4140
caaataggca acgatccaaa taggatata ttaattgcaa gcaactggta ctttaatcat      4200 ttaaagata aaatttttagg atgtgattgg tactttgtac ctacagatga aggatggaca      4260
aatgattaaa cagattgata tgttcatgat tactctatat aaaaaattaa ataatataac      4320
aatctagcta tattattt                                                   4338
```

<210> SEQ ID NO 2

```
<211> LENGTH: 1368
<212> TYPE: DNA
<213> ORGANISM: Clostridium tetani

<400> SEQUENCE: 2
atgggatcct caaaaaatct ggattgttgg gttgataatg aagaagatat agatgttata      60
ttaaaaaga  gtacaatttt aaatttagat attaataatg atattatatc agatatatct     120
gggtttaatt catctgtaat aacatatcca gatgctcaat ggtgcccgg  aataaatggc     180
aaagcaatac atttagtaaa caatgaatct tctgaagtta tagtgcataa agctatggat     240
attgaatata atgatatgtt taataatttt accgttagct tttggttgag ggttcctaaa     300
gtatctgcta gtcatttaga acaatatggc acaaatgagt attcaataat tagctctatg     360
aaaaaacata gtctatcaat aggatctggt tggagtgtat cacttaaagg taataactta     420
atatggactt taaaagattc cgcgggagaa gttagacaaa taacttttag ggatttacct     480
gataaattta atgcttattt agcaaataaa tgggttttta taactattac taatgataga     540
ttatcttctg ctaatttgta tataaatgga gtacttatgg aagtgcaga  aattactggt     600
ttaggagcta ttagagagga taataatata acattaaaac tagatagatg taataataat     660
aatcaatacg tttctattga taaatttagg atattttgca aagcattaaa tccaaaagag     720
attgaaaaat tatacacaag ttatttatct ataaccttt  taagagactt ctggggaaac     780
cctttacgat atgatacaga atattattta ataccagtag cttctagttc taaagatgtt     840
caattgaaaa atataacaga ttatatgtat ttgacaaatg cgccatcgta tactaacgga     900
aaattgaata tatattatag aaggttatat aatggactaa aatttattat aaaaagatat     960
acacctaata atgaaataga ttctttttgtt aaatcaggtg attttattaa attatatgta    1020
tcatataaca ataatgagca cattgtaggt tatccgaaag atggaaatgc ctttaataat    1080
cttgatagaa ttctaagagt aggttataat gccccaggta tccctcttta taaaaaaatg    1140
gaagcagtaa aattgcgtga tttaaaaacc tattctgtac aacttaaatt atatgatgat    1200
aaaaatgcat ctttaggact agtaggtacc cataatggtc aaataggcaa cgatccaaat    1260
agggatatat taattgcaag caactggtac tttaatcatt taaagataaa attttagga     1320
tgtgattggt actttgtacc tacagatgaa ggatggacaa tgattaa               1368

<210> SEQ ID NO 3
<211> LENGTH: 455
<212> TYPE: PRT
<213> ORGANISM: Clostridium tetani

<400> SEQUENCE: 3

Met Gly Ser Ser Lys Asn Leu Asp Cys Trp Val Asp Asn Glu Glu Asp
  1               5                  10                  15

Ile Asp Val Ile Leu Lys Lys Ser Thr Ile Leu Asn Leu Asp Ile Asn
                 20                  25                  30

Asn Asp Ile Ile Ser Asp Ile Ser Gly Phe Asn Ser Ser Val Ile Thr
             35                  40                  45

Tyr Pro Asp Ala Gln Leu Val Pro Gly Ile Asn Gly Lys Ala Ile His
         50                  55                  60

Leu Val Asn Asn Glu Ser Ser Glu Val Ile Val His Lys Ala Met Asp
 65                  70                  75                  80

Ile Glu Tyr Asn Asp Met Phe Asn Asn Phe Thr Val Ser Phe Trp Leu
                 85                  90                  95

Arg Val Pro Lys Val Ser Ala Ser His Leu Glu Gln Tyr Gly Thr Asn
```

```
            100                 105                 110
Glu Tyr Ser Ile Ile Ser Ser Met Lys Lys His Ser Leu Ser Ile Gly
        115                 120                 125
Ser Gly Trp Ser Val Ser Leu Lys Gly Asn Asn Leu Ile Trp Thr Leu
    130                 135                 140
Lys Asp Ser Ala Gly Glu Val Arg Gln Ile Thr Phe Arg Asp Leu Pro
145                 150                 155                 160
Asp Lys Phe Asn Ala Tyr Leu Ala Asn Lys Trp Val Phe Ile Thr Ile
                165                 170                 175
Thr Asn Asp Arg Leu Ser Ser Ala Asn Leu Tyr Ile Asn Gly Val Leu
            180                 185                 190
Met Gly Ser Ala Glu Ile Thr Gly Leu Gly Ala Ile Arg Glu Asp Asn
        195                 200                 205
Asn Ile Thr Leu Lys Leu Asp Arg Cys Asn Asn Asn Gln Tyr Val
    210                 215                 220
Ser Ile Asp Lys Phe Arg Ile Phe Cys Lys Ala Leu Asn Pro Lys Glu
225                 230                 235                 240
Ile Glu Lys Leu Tyr Thr Ser Tyr Leu Ser Ile Thr Phe Leu Arg Asp
                245                 250                 255
Phe Trp Gly Asn Pro Leu Arg Tyr Asp Thr Glu Tyr Tyr Leu Ile Pro
            260                 265                 270
Val Ala Ser Ser Lys Asp Val Gln Leu Lys Asn Ile Thr Asp Tyr
        275                 280                 285
Met Tyr Leu Thr Asn Ala Pro Ser Tyr Thr Asn Gly Lys Leu Asn Ile
    290                 295                 300
Tyr Tyr Arg Arg Leu Tyr Asn Gly Leu Lys Phe Ile Ile Lys Arg Tyr
305                 310                 315                 320
Thr Pro Asn Asn Glu Ile Asp Ser Phe Val Lys Ser Gly Asp Phe Ile
                325                 330                 335
Lys Leu Tyr Val Ser Tyr Asn Asn Glu His Ile Val Gly Tyr Pro
            340                 345                 350
Lys Asp Gly Asn Ala Phe Asn Asn Leu Asp Arg Ile Leu Arg Val Gly
        355                 360                 365
Tyr Asn Ala Pro Gly Ile Pro Leu Tyr Lys Lys Met Glu Ala Val Lys
    370                 375                 380
Leu Arg Asp Leu Lys Thr Tyr Ser Val Gln Leu Lys Leu Tyr Asp Asp
385                 390                 395                 400
Lys Asn Ala Ser Leu Gly Leu Val Gly Thr His Asn Gly Gln Ile Gly
                405                 410                 415
Asn Asp Pro Asn Arg Asp Ile Leu Ile Ala Ser Asn Trp Tyr Phe Asn
            420                 425                 430
His Leu Lys Asp Lys Ile Leu Gly Cys Asp Trp Tyr Phe Val Pro Thr
        435                 440                 445
Asp Glu Gly Trp Thr Asn Asp
    450                 455

<210> SEQ ID NO 4
<211> LENGTH: 51
<212> TYPE: DNA
<213> ORGANISM: Artificial Sequence
<220> FEATURE:
<223> OTHER INFORMATION: laboratory-synthesized artificial primer

<400> SEQUENCE: 4
ggtggttgct cttccaacat gggatcctca aaaaatctgg attgttgggt t          51
```

```
<210> SEQ ID NO 5
<211> LENGTH: 40
<212> TYPE: DNA
<213> ORGANISM: Artificial Sequence
<220> FEATURE:
<223> OTHER INFORMATION: laboratory-synthesized artificial primer

<400> SEQUENCE: 5
ggtggtctgc agttcattaa tcatttgtcc atccttcatc                              40
```

UNITED STATES PATENT AND TRADEMARK OFFICE
CERTIFICATE OF CORRECTION

PATENT NO. : 9,616,139 B2
APPLICATION NO. : 14/128958
DATED : April 11, 2017
INVENTOR(S) : Edward T. Ryan et al.

Page 1 of 1

It is certified that error appears in the above-identified patent and that said Letters Patent is hereby corrected as shown below:

On the Title Page

Column 1 (Assignees), Line 5, delete "Washington, DC" and insert -- Rockville, MD --.

In the Specification

In Column 1, Lines 17-18 (approx.), delete "A1077883, U01 A1058935, U01 A1089721," and insert -- AI077883, U01 AI058935, U01 AI089721, --.

Signed and Sealed this
Fifteenth Day of August, 2017

Joseph Matal
*Performing the Functions and Duties of the*
*Under Secretary of Commerce for Intellectual Property and*
*Director of the United States Patent and Trademark Office*